United States Patent
Danilkovitch et al.

(10) Patent No.: US 10,603,174 B2
(45) Date of Patent: Mar. 31, 2020

(54) COMPOSITIONS COMPRISING MENISCAL TISSUES AND USES THEREOF

(71) Applicant: Osiris Therapeutics, Inc., Columbia, MD (US)

(72) Inventors: Alla Danilkovitch, Columbia, MD (US); Jinqiang Kuang, Woodstock, MD (US); Steven Michael Sinclair, Ellicott City, MD (US)

(73) Assignee: Osiris Therapeutics, Inc., Columbia, MD (US)

( * ) Notice: Subject to any disclaimer, the term of this patent is extended or adjusted under 35 U.S.C. 154(b) by 0 days.

(21) Appl. No.: 15/079,867

(22) Filed: Mar. 24, 2016

(65) Prior Publication Data

US 2016/0310280 A1    Oct. 27, 2016

Related U.S. Application Data

(60) Provisional application No. 62/137,654, filed on Mar. 24, 2015.

(51) Int. Cl.
*A61F 2/30* (2006.01)
*A61L 27/54* (2006.01)
(Continued)

(52) U.S. Cl.
CPC ........ *A61F 2/30756* (2013.01); *A61F 2/3872* (2013.01); *A61L 27/3604* (2013.01);
(Continued)

(58) Field of Classification Search
CPC .............. A61F 2/30756; A61F 2/30807; A61F 2/3872; A61F 2250/00; A61F 2310/00371;
(Continued)

(56) References Cited

U.S. PATENT DOCUMENTS

| 1,770,665 A | 7/1930 | Anderson |
| 3,974,526 A | 8/1976 | Dardik et al. |

(Continued)

FOREIGN PATENT DOCUMENTS

| EP | 0522139 A1 | 1/1993 |
| WO | WO-91/06213 A1 | 5/1991 |

(Continued)

OTHER PUBLICATIONS

Cook et al., A novel bioabsorbable conduit augments healing of avascular meniscal tears in a dog model. The American Journal of Sports Medicine, vol. 35, No. 11 (2007) pp. 1877-1887.*

(Continued)

*Primary Examiner* — Kara D Johnson
(74) *Attorney, Agent, or Firm* — Norton Rose Fulbright US LLP

(57) ABSTRACT

Disclosed are compositions comprising a meniscal tissue. For example, disclosed are compositions comprising a meniscal tissue, wherein the meniscal tissue comprises one or more engineered channels. Disclosed are compositions comprising a meniscal tissue comprising viable cells native to the meniscal tissue and devitalized blood vessels. Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells. Also disclosed are methods of producing and using these compositions comprising meniscal tissue.

17 Claims, 21 Drawing Sheets

(51) Int. Cl.
*A61L 27/36* (2006.01)
*A61L 27/38* (2006.01)
*A61F 2/38* (2006.01)

(52) U.S. Cl.
CPC ....... *A61L 27/3612* (2013.01); *A61L 27/3654* (2013.01); *A61L 27/3852* (2013.01); *A61L 27/54* (2013.01); *A61F 2/3094* (2013.01); *A61F 2002/30006* (2013.01); *A61F 2002/30047* (2013.01); *A61F 2002/30807* (2013.01); *A61F 2250/00* (2013.01); *A61F 2310/00371* (2013.01); *A61L 2300/414* (2013.01)

(58) Field of Classification Search
CPC ............. A61L 27/3604; A61L 27/3612; A61L 27/3654; A61L 27/3852
See application file for complete search history.

(56) References Cited

U.S. PATENT DOCUMENTS

| | | | |
|---|---|---|---|
| 3,988,782 A | 11/1976 | Dardik et al. | |
| 4,239,492 A | 12/1980 | Holman et al. | |
| 4,240,794 A | 12/1980 | Holman et al. | |
| 4,487,567 A | 12/1984 | Possis et al. | |
| 4,599,226 A | 7/1986 | Fox, Jr. et al. | |
| 4,601,718 A | 7/1986 | Possis et al. | |
| 4,711,238 A | 12/1987 | Cunningham | |
| 4,729,139 A | 3/1988 | Nashef | |
| 4,786,287 A | 11/1988 | Nashef et al. | |
| 4,798,611 A | 1/1989 | Freeman, Jr. | |
| 4,894,063 A | 1/1990 | Nashef | |
| 4,909,979 A | 3/1990 | Possis et al. | |
| 4,990,131 A | 2/1991 | Dardik et al. | |
| 5,131,908 A | 7/1992 | Dardik et al. | |
| 5,171,660 A | 12/1992 | Carpenter et al. | |
| 5,558,875 A | 9/1996 | Wang | |
| 5,595,571 A | 1/1997 | Jaffe et al. | |
| 5,645,587 A | 7/1997 | Chanda et al. | |
| 5,676,098 A | 10/1997 | Cecur | |
| 5,676,698 A | 10/1997 | Janzen et al. | |
| 5,681,353 A | 10/1997 | Li et al. | |
| 5,843,180 A | 12/1998 | Jaffe et al. | |
| 5,843,181 A | 12/1998 | Jaffe et al. | |
| 5,922,024 A | 7/1999 | Janzen et al. | |
| 6,152,142 A | 11/2000 | Tseng | |
| 6,193,749 B1 | 2/2001 | Schroeder et al. | |
| 6,254,637 B1 | 7/2001 | Lee et al. | |
| 6,280,467 B1 | 8/2001 | Leonhardt | |
| 6,284,519 B1 | 9/2001 | Young et al. | |
| 6,302,909 B1 | 10/2001 | Ogle et al. | |
| 6,391,538 B1 | 5/2002 | Vyavahare et al. | |
| 6,468,314 B2 | 10/2002 | Schwartz et al. | |
| 6,506,398 B1 | 1/2003 | Tu et al. | |
| 6,699,252 B2 | 3/2004 | Farr, II et al. | |
| 7,129,035 B2 | 10/2006 | Goldstein et al. | |
| 7,175,965 B2 | 2/2007 | Kawamura | |
| 7,294,144 B1 | 11/2007 | Schneider | |
| 7,432,241 B1 | 10/2008 | Quijano et al. | |
| 7,824,671 B2 | 11/2010 | Binder et al. | |
| 7,927,414 B2 | 4/2011 | Yang et al. | |
| 7,993,681 B2 | 8/2011 | Roth | |
| 8,105,634 B2 | 1/2012 | Liu et al. | |
| 8,231,908 B2 | 7/2012 | Kinoshita et al. | |
| 8,323,701 B2 | 12/2012 | Daniel et al. | |
| 8,324,449 B2 | 12/2012 | McQuillan et al. | |
| 8,349,885 B2 | 1/2013 | Kim et al. | |
| 8,357,403 B2 | 1/2013 | Daniel et al. | |
| 8,372,437 B2 | 2/2013 | Daniel | |
| 8,372,438 B2 | 2/2013 | Daniel et al. | |
| 8,372,439 B2 | 2/2013 | Daniel et al. | |
| 8,409,626 B2 | 4/2013 | Daniel et al. | |
| 8,460,715 B2 | 6/2013 | Daniel | |
| 8,623,421 B2 | 1/2014 | Daniel | |
| 8,642,092 B2 | 2/2014 | Daniel et al. | |
| 8,663,625 B2 | 3/2014 | Stroock et al. | |
| 8,703,206 B2 | 4/2014 | Daniel et al. | |
| 8,703,207 B2 | 4/2014 | Daniel et al. | |
| 8,703,411 B2 | 4/2014 | Chang et al. | |
| 8,709,493 B2 | 4/2014 | Daniel et al. | |
| 8,709,494 B2 | 4/2014 | Daniel | |
| 8,790,923 B2 | 7/2014 | Ennis et al. | |
| 8,795,284 B2 | 8/2014 | Ribeiro et al. | |
| 8,834,928 B1 | 9/2014 | Truncale et al. | |
| 8,840,665 B2 | 9/2014 | Young et al. | |
| 8,904,664 B2 | 12/2014 | Pringle et al. | |
| 8,906,362 B2 * | 12/2014 | Ferguson | A61L 27/3604 424/423 |
| 8,932,643 B2 | 1/2015 | Daniel et al. | |
| 8,932,805 B1 | 1/2015 | Brahm | |
| 8,961,617 B2 | 2/2015 | Young | |
| 2006/0280768 A1 | 12/2006 | Hwang et al. | |
| 2008/0183291 A1 | 7/2008 | Scheller et al. | |
| 2013/0172999 A1 | 7/2013 | Kaplan et al. | |
| 2013/0304209 A1 | 11/2013 | Schmieding et al. | |

FOREIGN PATENT DOCUMENTS

| | | |
|---|---|---|
| WO | WO-92/12631 A1 | 8/1992 |
| WO | WO-92/20300 A1 | 11/1992 |
| WO | WO-2011/031642 A2 | 3/2011 |

OTHER PUBLICATIONS

Zhang et al., Repairs by trephination and suturing of longitudinal injuries in the avascular area of the meniscus in goats. The American Journal of Sports Medicine, vol. 23, No. 1 (1995) pp. 35-41.*

Jackson et al., Meniscal transplantation using fresh and cryopreserved allografts. The American Journal of Sports Medicine, vol. 20, No. 6 (1992) pp. 644-656.*

"Exogenous", The Free Dictionary: Medical Dictionary, 2019 [retrieved on May 17, 2019]. Retrieved from the Internet: <URL: https://medical-dictionary.thefreedictionary.com/exogenous>. (Year: 2019).*

Abrams GD, Frank RM, Gupta AK, Harris JD, McCormick FM, Cole BJ. Trends in meniscus repair and meniscectomy in the United States, 2005-2011. The American journal of sports medicine. 2013:0363546513495641.

Arnoczky SP, Warren RF. Microvasculature of the human meniscus. The American journal of sports medicine. 1982;10:90-5.

Baratz ME, Fu FH, Mengato R. Meniscal tears: The effect of meniscectomy and of repair on intraarticular contact areas and stress in the human knee A preliminary report. The American Journal of Sports Medicine. 1986;14:270-5.

Brindle T, Nyland J, Johnson DL "The Meniscus: Review of Basic Principles With Application to Surgery and Rehabilitation" J. of Athletic Training 2001, 36(2) 160-169.

Chang, et al., "Protein-releasing polymeric scaffolds induce fibrochondrocytic differentiation of endogenous cells for knee meniscus regeneration in sheep", www.ScienceTranslationalMedicine.org Dec. 10, 2014 vol. 6 Issue 266 (12 pages).

Cole BJ, Dennis MG, Lee SJ, Nho SJ, Kalsi RS, Hayden JK, et al. Prospective Evaluation of Allograft Meniscus Transplantation A Minimum 2-Year Follow-up. The American journal of sports medicine. 2006;34:919-27.

Elattar M, Dhollander A, Verdonk R, Almqvist KF, Verdonk P. Twenty-six years of meniscal allograft transplantation: is it still experimental? A meta-analysis of 44 trials. Knee Surgery, Sports Traumatology, Arthroscopy. 2011;19:147-57.

Fairbank T. Knee joint changes after meniscectomy. Journal of Bone & Joint Surgery, British Volume. 1948;30:664-70.

Fox AJ, Bedi A, Rodeo SA. The Basic Science of Human Knee Menisci Structure, Composition, and Function. Sports Health: A Multidisciplinary Approach. 2012;4:340-51.

Hergan D, Thut D, Sherman O, Day MS. Meniscal allograft transplantation. Arthroscopy: The Journal of Arthroscopic & Related Surgery. 2011;27:101-12.

(56) References Cited

OTHER PUBLICATIONS

Lee SR, Kim JG, Nam SW "The Tips and Pitfalls of Meniscus Allograft Transplantation" Knee Surg Relat Res 2012, 24(3) 137-145.
Makris EA, Hadidi P, Athanasiou KA. The knee meniscus: structure—function, pathophysiology, current repair techniques, and prospects for regeneration. Biomaterials. 2011;32:7411-31.
McCormick F, Harris JD, Abrams GD, Hussey KE, Wilson H, Frank R, et al. Survival and Reoperation Rates After Meniscal Allograft Transplantation Analysis of Failures for 172 Consecutive Transplants at a Minimum 2-Year Follow-up. The American journal of sports medicine. 2014;42:892-7.
McDermott I, Amis A. The consequences of meniscectomy. Journal of Bone & Joint Surgery, British Volume. 2006;88:1549-56.
Minehara, et al., "A new technique for seeding chondrocytes onto solventpreserved human meniscus using the chemokinetic effect of recombinant human bone morphogenetic protein-2", Cell Tissue Bank (2011) 12:199-207.
Mulder, "Meniscus Tissue Engineering" (2013) (147 pages).
Noyes FR, Barber-Westin SD, Rankin M. Meniscal transplantation in symptomatic patients less than fifty years old. The Journal of Bone & Joint Surgery. 2004;86:1392-404.
Pangborn, "Growth factors in tissue engineering the knee meniscus" Masters Thesis, Rice University, 2004, (97 pages).
Peterson, et al., "Collagenous fibril texture of the human knee joint menisci", Anat Embryol (1998) 197:317-324.
Rodkey WG, DeHaven KE, Montgomery WH, Baker CL, Beck CL, Hormel SE, et al. Comparison of the collagen meniscus implant with partial meniscectomy. The Journal of Bone & Joint Surgery. 2008;90:1413-26.
Roos H, Laurén M, Adalberth T, Roos EM, Jonsson K, Lohmander LS. Knee osteoarthritis after meniscectomy: prevalence of radiographic changes after twenty-one years, compared with matched controls. Arthritis & Rheumatism. 1998;41:687-93.
Stollsteimer GT, Shelton WR, Dukes A, Bomboy AL. Meniscal allograft transplantation: a 1-to 5-year follow-up of 22 patients. Arthroscopy: The Journal of Arthroscopic & Related Surgery. 2000;16:343-7.
Verdonk P, Beaufils P, Bellemans J, Djian P, Heinrichs E-L, Huysse W, et al. Successful treatment of painful irreparable partial meniscal defects with a polyurethane scaffold two-year safety and clinical outcomes. The American journal of sports medicine. 2012;40:844-53.
Verdonk PC, Verstraete KL, Almqvist KF, De Cuyper K, Veys EM, Verbruggen G, et al. Meniscal allograft transplantation: long-term clinical results with radiological and magnetic resonance imaging correlations. Knee Surgery, Sports Traumatology, Arthroscopy. 2006;14:694-706.
Zaffagnini S, Muccioli GMM, Lopomo N, Bruni D, Giordano G, Ravazzolo G, et al. Prospective Long-Term Outcomes of the Medial Collagen Meniscus Implant Versus Partial Medial Meniscectomy A Minimum 10-Year Follow-Up Study. The American journal of sports medicine. 2011;39:977-85.
Hwang, R., et al., Meniscus Regeneration Through a 3D-Printed Mesenchymal Stem Cell Graft, (2013) Retrieved on May 31, 2016 from the Internet: <URL:https://web.archive.org/web/20130401235219/http://jasonsilver.net/Meniscus%20Regeneration%20Through%20a%203DPrinted%20Mesenchymai%20Stem%20Ceii%20Graft.pdf>; p. 4, 2nd column.
Heatley, FW, The meniscus—can it be repaired? An experimental investigation in rabbits, Journal of Bone & Joint Surgery, British vol. 62.3 (1980): 397-402. Aug. 1980; especially p. 400.
International Search Report and Written Opinion dated Sep. 19, 2016 for Application No. PCT/US2016/024042, which was filed on Mar. 24, 2016 (Inventor—Danilkovitch; Applicant—Osiris Therapeutics, Inc.) (14 pages).

* cited by examiner

Irreparable Posterior Tear
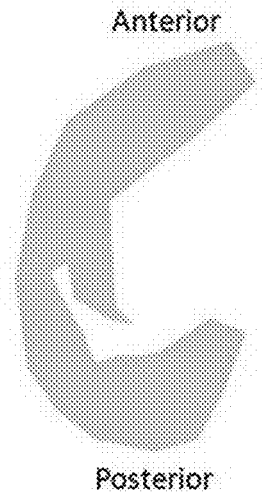
Estimate Defect Length
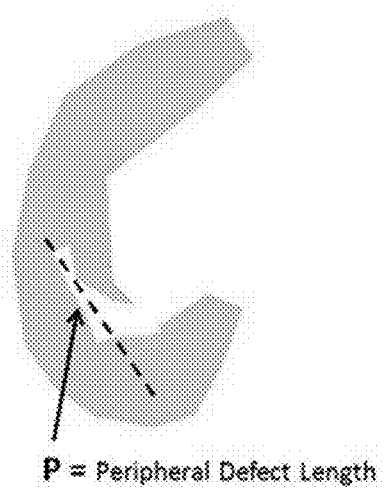
P = Peripheral Defect Length
FIG. 16     P ≤ 25 mm
Define Defect with Radial Cuts
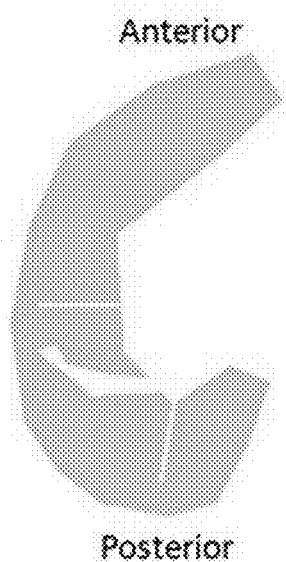
FIG. 17

Measure Defect Dimensions

Cut Meniscal tissue to size

COMPOSITIONS COMPRISING MENISCAL TISSUES AND USES THEREOF

CROSS-REFERENCE TO RELATED APPLICATIONS

This application claims benefit of U.S. Provisional Application No. 62/137,654, filed Mar. 24, 2015, which is hereby incorporated herein by reference in its entirety.

BACKGROUND

An estimated one million surgical procedures in the United States each year involve injuries of the meniscus. Meniscus tissue has proven to have poor healing characteristics, which has led to an increased demand for treatment options for meniscus repair and replacement. Damaged meniscal tissue results in increased pain and decreased knee function/mobility. Meniscectomy is the surgical procedure commonly used for removing all or part of a torn or degenerated meniscus. However, meniscectomy is known to alter the biomechanics of the knee and increase the risk of developing osteoarthritis and needing a total joint replacement in the long-term. A need exists for a biologic allograft for repairing meniscal damage that preserves key components of the native tissue, such as viable endogenous cells, growth factors, and extracellular matrix, and facilitates rapid and complete healing.

BRIEF SUMMARY

Disclosed are compositions comprising a meniscal tissue, wherein the meniscal tissue comprises one or more engineered channels.

Disclosed are compositions comprising a meniscal tissue, wherein the meniscal tissue comprises one or more engineered channels, wherein the meniscal tissue further comprises a red zone or an altered red zone. In some instances, the meniscal tissue further comprises a red-white zone, and a white zone. The meniscal tissue can also comprise an altered red-white zone.

Disclosed are compositions comprising a meniscal tissue, wherein the meniscal tissue comprises one or more engineered channels, wherein the meniscal tissue further comprises a red zone or an altered red zone, wherein the meniscal tissue has an inner edge and an opposed outer edge, and wherein the red zone or altered red zone has an outer surface that defines the outer edge of the meniscal tissue.

Disclosed are compositions comprising a meniscal tissue, wherein the meniscal tissue comprises one or more engineered channels, wherein the meniscal tissue further comprises a red zone or an altered red zone, a red-white zone, and a white zone, wherein the red zone or altered red zone, red-white zone, and white zone are in an orientation as present in native meniscal tissue. In the case of the altered red zone, the altered red zone is present in the orientation that a red zone is found in native meniscal tissue.

Disclosed are compositions comprising a meniscal tissue, wherein the meniscal tissue comprises one or more engineered channels, wherein the engineered channels are only present in the red zone or altered red zone. In some instances, the engineered channels are only present in the red zone and red-white zone or in the altered red zone and altered red-white zone.

Disclosed are compositions comprising a meniscal tissue, wherein the meniscal tissue comprises one or more engineered channels, wherein the meniscal tissue has an inner edge and an opposed outer edge, and wherein at least one engineered channel does not extend from the outer edge of the meniscal tissue to the inner edge of the meniscal tissue.

Disclosed are compositions comprising a meniscal tissue, wherein the meniscal tissue comprises one or more engineered channels, wherein at least one engineered channel does not extend completely through the red zone or altered red zone. Disclosed are compositions comprising a meniscal tissue, wherein the meniscal tissue comprises one or more engineered channels, wherein the meniscal tissue has an inner edge and an opposed outer edge, and wherein at least one engineered channel extends from the outer edge through only a portion of the altered red zone.

Disclosed are compositions comprising a meniscal tissue, wherein the meniscal tissue comprises one or more engineered channels, wherein the meniscal tissue has an inner edge and an opposed outer edge, wherein the inner edge is spaced from the outer edge in an inward direction, and wherein the engineered channels extend substantially in the inward direction.

Disclosed are compositions comprising a meniscal tissue, wherein the meniscal tissue comprises one or more engineered channels, wherein the meniscal tissue has an inner edge and an opposed outer edge, the outer edge having an exterior surface, wherein each engineered channel has a first end defined in the exterior surface of the outer edge of the meniscal tissue and an opposed second end defined within the red zone or altered red zone of the meniscal tissue, and wherein the first ends of the engineered channels are substantially evenly spaced about the exterior surface of the outer edge of the meniscal tissue.

Disclosed are compositions comprising a meniscal tissue, wherein the meniscal tissue comprises one or more engineered channels, wherein each engineered channel has a diameter ranging from about 0.05 mm to about 2 mm.

Disclosed are compositions comprising a meniscal tissue, wherein the meniscal tissue comprises one or more engineered channels, wherein each engineered channel has a longitudinal axis, and wherein each engineered channel has a consistent diameter throughout the entire longitudinal length of the engineered channels. In some instances, the diameter of an engineered channel can vary along the longitudinal length of the engineered channel.

Disclosed are compositions comprising a meniscal tissue, wherein the meniscal tissue comprises one or more engineered channels, wherein each engineered channel has a diameter, and wherein the diameter of at least one engineered channel is equal to the diameter of at least one other engineered channel. In some instances, the engineered channels can all have substantially the same diameter.

Disclosed are compositions comprising a meniscal tissue, wherein the meniscal tissue comprises one or more engineered channels, wherein each engineered channel has a longitudinal axis, and wherein each engineered channel has a longitudinal length ranging from about 0.1 mm to about 10 mm.

Disclosed are compositions comprising a meniscal tissue, wherein the meniscal tissue comprises one or more engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length.

Disclosed are compositions comprising a meniscal tissue, wherein the meniscal tissue comprises one or more engineered channels, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm.

Also disclosed are compositions comprising a meniscal tissue, wherein the meniscal tissue comprises one or more engineered channels, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm.

Disclosed are compositions comprising a meniscal tissue, wherein the meniscal tissue comprises one or more engineered channels, wherein the meniscal tissue comprises viable cells native to the meniscal tissue. In some instances, the meniscal tissue comprises at least 70% viable cells native to the meniscal tissue.

Disclosed are compositions comprising a meniscal tissue, wherein the meniscal tissue comprises one or more engineered channels, wherein the composition is not immunogenic.

Disclosed are compositions comprising a meniscal tissue, wherein the meniscal tissue comprises one or more engineered channels, wherein the meniscal tissue comprises one or more growth factors native to the meniscal tissue. The growth factors can be one or more of TGF-β1, TGF-b3, bFGF, PDGF-AB, PDGF-BB, IGF-1, HGF, BMP-7, EGF, CTGF, BMP-2, BMP-6, and VEGF.

Disclosed are compositions comprising a meniscal tissue, wherein the meniscal tissue comprises one or more engineered channels further comprising exogenous cells, growth factors, or proteins.

Disclosed are compositions comprising a meniscal tissue, wherein the meniscal tissue comprises one or more engineered channels, wherein the composition does not comprise fatty, immunogenic connective tissue. In some instances, the fatty, immunogenic connective tissue can be from the joint capsule.

Disclosed are compositions comprising a meniscal tissue, wherein the meniscal tissue comprises one or more engineered channels, wherein the meniscal tissue does not comprise hematopoietic cells.

Disclosed are compositions comprising a meniscal tissue, wherein the meniscal tissue comprises one or more engineered channels, wherein the meniscal tissue comprises all collagen layers of human meniscus. Also disclosed are compositions comprising a meniscal tissue, wherein the meniscal tissue comprises one or more engineered channels, wherein the meniscal tissue comprises at least one of the collagen layers of human meniscus.

Disclosed are compositions comprising a meniscal tissue, wherein the meniscal tissue comprises one or more engineered channels, wherein the meniscal tissue is cryopreserved. In some instances, the viability of the cells is substantially maintained for at least about 24 months when stored frozen.

Disclosed are compositions comprising a meniscal tissue, wherein the meniscal tissue comprises one or more engineered channels wherein the composition further comprises a cryopreservation solution.

Also disclosed are previously cryopreserved compositions comprising a meniscal tissue, wherein the meniscal tissue comprises one or more engineered channels.

Disclosed are compositions comprising a meniscal tissue, wherein the meniscal tissue comprises viable cells native to the meniscal tissue and devitalized blood vessels.

Disclosed are compositions comprising a meniscal tissue, wherein the meniscal tissue comprises viable cells native to the meniscal tissue and devitalized blood vessels, wherein the meniscal tissue further comprises an altered red zone. In some instances, the meniscal tissue further comprises a red-white zone, and a white zone. The meniscal tissue can also comprise an altered red-white zone.

Disclosed are compositions comprising a meniscal tissue, wherein the meniscal tissue comprises viable cells native to the meniscal tissue and devitalized blood vessels, wherein the meniscal tissue further comprises an altered red zone, wherein the meniscal tissue has an inner edge and an opposed outer edge, and wherein the altered red zone has an outer surface that defines the outer edge of the meniscal tissue.

Disclosed are compositions comprising a meniscal tissue, wherein the meniscal tissue comprises viable cells native to the meniscal tissue and devitalized blood vessels, wherein the meniscal tissue further comprises an altered red zone, a red-white zone, and a white zone, wherein the altered red zone, red-white zone, and white zone are in an orientation as present in native meniscal tissue.

Also disclosed are compositions comprising a meniscal tissue, wherein the meniscal tissue comprises greater than 30% viable non-immunogenic cells native to the meniscal tissue and less than 5% viable immunogenic cells.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises an altered red zone. In some instances, the meniscal tissue further comprises a red-white zone, and a white zone. The meniscal tissue can also comprise an altered red-white zone.

Disclosed are compositions comprising a meniscal, wherein the meniscal tissue comprises greater than 30% viable non-immunogenic cells native to the meniscal tissue and less than 5% viable immunogenic cells, wherein the meniscal tissue further comprises an altered red zone, wherein the meniscal tissue has an inner edge and an opposed outer edge, and wherein the altered red zone has an outer surface that defines the outer edge of the meniscal tissue.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises an altered red zone, a red-white zone, and a white zone, wherein the altered red zone, red-white zone, and white zone are in an orientation as present in native meniscal tissue.

Disclosed are compositions comprising a meniscal tissue, wherein the meniscal tissue comprises viable cells native to the meniscal tissue and devitalized blood vessels, wherein the meniscal tissue further comprises engineered channels.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, wherein the engineered channels are only present in the altered red zone. In some instances, the meniscal tissue further comprises and altered red-white zone, wherein the engineered channels are only present in the altered red zone and altered red-white zone.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, an altered red-white zone, and a white zone wherein the meniscal tissue has an inner edge and an opposed outer edge, and wherein at least one engineered channel does not extend from the outer edge of the meniscal tissue to the inner edge of the meniscal tissue.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, altered red-white zone, and white zone, wherein at least one engineered channel does not extend completely through the altered red zone. Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, wherein the meniscal tissue has an inner edge and an opposed outer edge, and wherein at least one engineered channel extends from the outer edge through only a portion of the altered red zone.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue has an inner edge and an opposed outer edge, wherein the inner edge is spaced from the outer edge in an inward direction, and wherein the engineered channels extend substantially in the inward direction.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, wherein the meniscal tissue has an inner edge and an opposed outer edge, the outer edge having an exterior surface, wherein each engineered channel has a first end defined in the exterior surface of the outer edge of the meniscal tissue and an opposed second end defined within the altered red zone of the meniscal tissue, and wherein the first ends of the engineered channels are substantially evenly spaced about the exterior surface of the outer edge of the meniscal tissue.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a diameter ranging from about 0.05 mm to about 2 mm.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a longitudinal axis, and wherein each engineered channel has a consistent diameter throughout the entire longitudinal length of the engineered channel.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a diameter, and wherein the diameter of at least one engineered channel is equal to the diameter of at least one other engineered channel. In some instances, the engineered channels can all have substantially the same diameter.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a longitudinal axis, and wherein each engineered channel has a longitudinal length ranging from about 0.1 mm to about 10 mm.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length.

Also disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, wherein the engineered channels are only present in the altered red zone. In some instances, the meniscal tissue further comprises and altered red-white zone, wherein the engineered channels are only present in the altered red zone and altered red-white zone.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, an altered red-white zone, and a white zone wherein the meniscal tissue has an inner edge and an opposed outer edge, and wherein at least one engineered channel does not extend from the outer edge of the meniscal tissue to the inner edge of the meniscal tissue.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, altered red-white zone, and white zone, wherein at least one engineered channel does not extend completely through the altered red zone. Disclosed are compositions comprising a meniscal tissue comprising greater than 30% viable non-immunogenic cells native to the meniscal tissue and less than 5% viable immunogenic cells, wherein the meniscal tissue further comprises engineered channels, wherein the meniscal tissue further comprises an altered red zone, wherein the meniscal tissue has an inner edge and an opposed outer edge, and wherein at least one engineered channel extends from the outer edge through only a portion of the altered red zone.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue has an inner edge and an opposed outer edge, wherein the inner edge is spaced from the outer edge in an inward direction, and wherein the engineered channels extend substantially in the inward direction.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, wherein the meniscal tissue has an inner edge and an opposed outer edge, the outer edge having an exterior surface, wherein each engineered channel has a first end defined in the exterior surface of the outer edge of the meniscal tissue and an opposed second end defined within the altered red zone of the meniscal tissue, and wherein the first ends of the engineered channels are substantially evenly spaced about the exterior surface of the outer edge of the meniscal tissue.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a diameter ranging from about 0.05 mm to about 2 mm.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a longitudinal axis, and wherein each engineered channel has a consistent diameter throughout the entire longitudinal length of the engineered channel.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a diameter, and wherein the diameter of at least one engineered channel is equal to the diameter of at least one other engineered channel. In some instances, the engineered channels can all have substantially the same diameter.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a longitudinal axis, and wherein each engineered channel has a longitudinal length ranging from about 0.1 mm to about 10 mm.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a longitudinal axis and a longitudinal length, and wherein the longitudinal length of at least one engineered channel is substantially equal to the longitudinal length of at least one other engineered channel.

Disclosed are compositions comprising a meniscal tissue, wherein the meniscal tissue comprises viable cells native to the meniscal tissue and devitalized blood vessels, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm.

Disclosed are compositions comprising a meniscal tissue, wherein the meniscal tissue comprises viable cells native to the meniscal tissue and devitalized blood vessels, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm.

Also disclosed are compositions comprising a meniscal tissue, wherein the meniscal tissue comprises greater than 30% viable non-immunogenic cells native to the meniscal tissue and less than 5% viable immunogenic cells, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm.

Disclosed are compositions comprising a meniscal tissue, wherein the meniscal tissue comprises viable cells native to the meniscal tissue and devitalized blood vessels. In some instances, the meniscal tissue comprises at least 70% viable cells native to the meniscal tissue.

Disclosed are compositions comprising a meniscal tissue, wherein the meniscal tissue comprises viable cells native to the meniscal tissue and devitalized blood vessels, wherein the composition is not immunogenic.

Disclosed are compositions comprising a meniscal tissue, wherein the meniscal tissue comprises viable cells native to the meniscal tissue and devitalized blood vessels, wherein the meniscal tissue comprises growth factors native to the meniscal tissue. The growth factors can be one or more of TGF-β1, TGF-b3, bFGF, PDGF-AB, PDGF-BB, IGF-1, HGF, BMP-7, EGF, CTGF, BMP-2, BMP-6, and VEGF.

Disclosed are compositions comprising a meniscal tissue, wherein the meniscal tissue comprises viable cells native to the meniscal tissue and devitalized blood vessels further comprising exogenous cells, growth factors, or proteins.

Disclosed are compositions comprising a meniscal tissue, wherein the meniscal tissue comprises viable cells native to the meniscal tissue and devitalized blood vessels, wherein the composition does not comprise fatty, immunogenic connective tissue. In some instances, the fatty, immunogenic connective tissue can be from the joint capsule.

Disclosed are compositions comprising a meniscal tissue, wherein the meniscal tissue comprises viable cells native to the meniscal tissue and devitalized blood vessels, wherein the meniscal tissue does not comprise hematopoietic cells.

Disclosed are compositions comprising a meniscal tissue, wherein the meniscal tissue comprises viable cells native to the meniscal tissue and devitalized blood vessels, wherein the meniscal tissue comprises all collagen layers of human meniscus. Also disclosed are compositions comprising a meniscal tissue, wherein the meniscal tissue comprises viable cells native to the meniscal tissue and devitalized blood vessels, wherein the meniscal tissue comprises at least one of the collagen layers of human meniscus.

Also disclosed are compositions comprising a meniscal tissue, wherein the meniscal tissue comprises greater than 30% viable non-immunogenic cells native to the meniscal tissue and less than 5% viable immunogenic cells. In some instances, the meniscal tissue comprises at least 70% viable cells native to the meniscal tissue.

Disclosed are compositions comprising a meniscal tissue, wherein the meniscal tissue comprises greater than 30% viable non-immunogenic cells native to the meniscal tissue and less than 5% viable immunogenic cells, wherein the composition is not immunogenic.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue comprises growth factors native to the meniscal tissue. The growth factors can be one or more of TGF-β, TGF-b3, bFGF, PDGF-AB, PDGF-BB, IGF-1, HGF, BMP-7, EGF, CTGF, BMP-2, BMP-6, and VEGF.

Disclosed are compositions comprising a meniscal tissue, wherein the meniscal tissue comprises greater than 30% viable non-immunogenic cells native to the meniscal tissue and less than 5% viable immunogenic cells further comprising exogenous cells, growth factors, or proteins.

Disclosed are compositions comprising a meniscal tissue, wherein the meniscal tissue comprises greater than 30% viable non-immunogenic cells native to the meniscal tissue and less than 5% viable immunogenic cells, wherein the composition does not comprise fatty, immunogenic connective tissue. In some instances, the fatty, immunogenic connective tissue can be from the joint capsule.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue does not comprise hematopoietic cells.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue comprises all collagen layers of human meniscus. Also disclosed are compositions comprising a meniscal tissue, wherein the meniscal tissue comprises greater than 30% viable non-immunogenic cells native to the meniscal tissue and less than 5% viable immunogenic cells, wherein the meniscal tissue comprises at least one of the collagen layers of human meniscus.

Disclosed are compositions comprising a meniscal tissue, wherein the meniscal tissue comprises viable cells native to the meniscal tissue and devitalized blood vessels, wherein the meniscal tissue is cryopreserved. In some instances, the viability of the cells is substantially maintained for at least about 24 months when stored frozen Disclosed are compositions comprising a meniscal tissue, wherein the meniscal tissue comprises viable cells native to the meniscal tissue and devitalized blood vessels further comprising a cryopreservation solution.

Also disclosed are previously cryopreserved compositions comprising a meniscal tissue, wherein the meniscal tissue comprises viable cells native to the meniscal tissue and devitalized blood vessels as described herein.

Also disclosed are compositions comprising a meniscal tissue, wherein the meniscal tissue comprises greater than 30% viable non-immunogenic cells native to the meniscal tissue and less than 5% viable immunogenic cells, wherein the meniscal tissue is cryopreserved. In some instances, the viability of the cells is substantially maintained for at least about 24 months when stored frozen Disclosed are compositions comprising a meniscal tissue, wherein the meniscal tissue comprises greater than 30% viable non-immunogenic cells native to the meniscal tissue and less than 5% viable immunogenic cells further comprising a cryopreservation solution.

Also disclosed are previously cryopreserved compositions comprising a meniscal tissue, wherein the meniscal tissue comprises greater than 30% viable non-immunogenic cells native to the meniscal tissue and less than 5% viable immunogenic cells as described herein.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more or all types of functional immunogenic cells.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises an altered red zone. The meniscal tissue can also comprise an altered red-white zone.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises an altered red zone, wherein the meniscal tissue has an inner edge and an opposed outer edge, and wherein the altered red zone has an outer surface that defines the outer edge of the meniscal tissue.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises an altered red zone, an altered red-white zone, and a white zone, wherein the altered red zone, altered red-white zone, and white zone are in an orientation as present in native meniscal tissue.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, wherein the engineered channels are only present in the altered red zone. In some instances, the meniscal tissue further comprises and altered red-white zone, wherein the engineered channels are only present in the altered red zone and altered red-white zone.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, an altered red-white zone, and a white zone wherein the meniscal tissue has an inner edge and an opposed outer edge, and wherein at least one engineered channel does not extend from the outer edge of the meniscal tissue to the inner edge of the meniscal tissue. For example, the outer edge of the meniscal tissue can be the edge containing the altered red zone while the inner edge can be the edge containing the white zone.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, altered red-white zone, and white zone, wherein at least one engineered channel does not extend completely through the altered red zone. Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, wherein the meniscal tissue has an inner edge and an opposed outer edge, and wherein at least one engineered channel extends from the outer edge through only a portion of the altered red zone.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue has an inner edge and an opposed outer edge, wherein the inner edge is spaced from the outer edge in an inward direction, and wherein the engineered channels extend substantially in the inward direction.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, wherein the meniscal tissue has an inner edge and an opposed outer edge, the outer edge having an exterior surface, wherein each engineered channel has a first end defined in the exterior surface of the outer edge of the meniscal tissue and an opposed second end defined within the altered red zone of the meniscal tissue, and wherein the first ends of the engineered channels are substantially evenly spaced about the exterior surface of the outer edge of the meniscal tissue.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a diameter ranging from about 0.05 mm to about 2 mm.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a longitudinal axis, and wherein each engineered channel has a consistent diameter throughout the entire longitudinal length of the engineered channel.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a diameter, and wherein the diameter of at least one engineered channel is equal to the diameter of at least one other engineered channel. In some instances, the engineered channels can all have substantially the same diameter.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a longitudinal axis, and wherein each engineered channel has a longitudinal length ranging from about 0.1 mm to about 10 mm.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue has an inner edge and an opposed outer edge, wherein the outer edge has a first end and an opposed second end, and wherein a first line extending from the first end of the outer edge to the second end of the outer edge has a length ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells. In some instances, the meniscal tissue comprises at least 70% viable cells native to the meniscal tissue.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the composition is not immunogenic.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue comprises growth factors native to the meniscal tissue. The growth factors can be one or more of TGF-$\beta$1, TGF-b3, bFGF, PDGF-AB, PDGF-BB, IGF-1, HGF, BMP-7, EGF, CTGF, BMP-2, BMP-6, and VEGF.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells further comprising exogenous cells, growth factors, or proteins.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the composition does not comprise fatty, immunogenic connective tissue. In some instances, the fatty, immunogenic connective tissue can be from the joint capsule.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue does not comprise hematopoietic cells.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue comprises all collagen layers of human meniscus. Also disclosed are compositions comprising a meniscal tissue, wherein the meniscal tissue comprises viable cells native to the meniscal tissue and devitalized blood vessels, wherein the meniscal tissue comprises at least one of the collagen layers of human meniscus.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the previously cryopreserved meniscal tissue is stored for an extended period of time prior to subsequent thawing. In some instances, the extended period of time is from about 1 day to at least 24 months.

Disclosed are methods of producing the disclosed compositions comprising forming engineered channels in a meniscal tissue isolated from a subject. For example, disclosed are methods of producing compositions comprising a meniscal tissue, comprising forming engineered channels in a meniscal tissue isolated from a subject. Also disclosed are methods of producing compositions comprising a meniscal tissue comprising viable cells native to the meniscal tissue and devitalized blood vessels, comprising forming engineered channels in a meniscal tissue isolated from a subject. Also disclosed are methods of producing compositions comprising a meniscal tissue comprising greater than 30% viable non-immunogenic cells native to the meniscal tissue and less than 5% viable immunogenic cells, wherein the meniscal tissue further comprises engineered channels, comprising forming engineered channels in a meniscal tissue isolated from a subject.

Disclosed are methods of repairing at least one meniscal defect in a meniscus of a subject comprising replacing the meniscal defect with any one of the disclosed compositions. For example, disclosed are methods of repairing at least one meniscal defect in a meniscus of a subject comprising replacing the meniscal defect with compositions comprising a meniscal tissue, wherein the meniscal tissue comprises one or more engineered channels. Disclosed are methods of repairing at least one meniscal defect in a meniscus of a subject comprising replacing the meniscal defect with compositions comprising a meniscal tissue comprising viable cells native to the meniscal tissue and devitalized blood vessels. Disclosed are methods of repairing at least one meniscal defect in a meniscus of a subject comprising replacing the meniscal defect with compositions comprising a meniscal tissue comprising greater than 30% viable non-immunogenic cells native to the meniscal tissue and less than 5% viable immunogenic cells. Disclosed are methods of repairing at least one meniscal defect in a meniscus of a subject comprising replacing the meniscal defect with compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells.

Replacing the at least one meniscal defect can comprise removing the at least one meniscal defect by cutting or shaving the meniscus around the at least one meniscal defect to define a receiving space, and inserting the composition into the receiving space.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space, wherein the meniscus has an inner edge and an opposed outer edge, the inner edge and the outer edge having respective exterior surfaces, wherein the step of removing the at least one meniscal defect comprises making a first incision on a first side of the at least one meniscal defect, wherein the first incision extends from the exterior surface of the inner edge to a first selected position spaced from the outer edge of the meniscus; and making a second incision on a second side of the at least one meniscal defect that is opposed from the first side of the at least one meniscal defect, wherein the second incision extends from the exterior surface of the inner edge to a second selected position spaced from the outer edge of the meniscus.

The step of removing the at least one meniscal defect can further comprise removing portions of the meniscus positioned between the first and second incisions to define the receiving space. The steps of making first and second incisions can define first and second side walls of the receiving space, and the step of removing portions of the meniscus positioned between the first and second incisions can comprise defining a peripheral wall of the receiving space, wherein the peripheral wall can be consistently radially spaced from the exterior surface of the outer edge of the meniscus.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space, wherein the meniscus has an inner edge and an opposed outer edge, the inner edge and the outer edge having respective exterior surfaces, wherein the step of removing the at least one meniscal defect comprises making a first incision on a first side of the at least one meniscal defect, wherein the first incision extends from the exterior surface of the inner edge to a first selected position spaced from the outer edge of the meniscus; and making a second incision on a second side of the at least one meniscal defect that is opposed from the first side of the at least one meniscal defect, wherein the second incision extends from the exterior surface of the inner edge to a second selected position spaced from the outer edge of the meniscus, further comprising forming a plurality of vascular access channels that extend from the peripheral wall of the receiving space of the subject's meniscus toward the exterior surface of the outer edge of the subject's meniscus.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, further comprising selectively removing portions of the composition until the composition has a desired shape that substantially corresponds to a shape of the receiving space.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space, wherein the meniscus has an inner edge and an opposed outer edge, the inner edge and the outer edge having respective exterior surfaces, wherein the step of removing the at least one meniscal defect comprises making a first incision on a first side of the at least one meniscal defect, wherein the first incision extends from the exterior surface of the inner edge to a first selected position spaced from the outer edge of the meniscus; and making a second incision on a second side of the at least one meniscal defect that is opposed from the first side of the at least one meniscal defect, wherein the second incision extends from the exterior surface of the inner edge to a second selected position spaced from the outer edge of the meniscus, wherein the step of removing the at least one meniscal defect further comprises removing portions of the meniscus positioned between the first and second incisions to define the receiving space, wherein the steps of making first and second incisions defines first and second side walls of the receiving space, and wherein the step of removing portions of the meniscus positioned between the first and second incisions comprises defining a peripheral wall of the receiving space, wherein the peripheral wall is consistently radially spaced from the exterior surface of the outer edge of the meniscus, wherein the step of attaching the composition to selected portions of the meniscus comprises inserting a fixation device into the composition.

In some instances, the step of attaching the composition to selected portions of the meniscus comprises securing at least a portion of the exterior surface of the outer edge of the composition to the peripheral wall of the receiving space of the meniscus. Optionally, the step of securing at least a portion of the exterior surface of the outer edge of the composition to the peripheral wall of the receiving space can comprise inserting the fixation device through the peripheral wall of the receiving space of the meniscus and passing the fixation device through the exterior surface of the outer edge of the meniscus.

In some instances, the step of attaching the composition to selected portions of the meniscus further comprises inserting at least one fixation device between the composition and the meniscus and across the first side wall of the receiving space of the meniscus; and inserting at least one fixation device between the composition and the meniscus and across the second side wall of the receiving space of the meniscus.

In the disclosed methods, cells from the meniscus or surrounding tissues or fluids of the subject can migrate to the meniscal tissue of the composition.

Disclosed are methods of repairing at least one meniscal defect in a meniscus of a subject comprising replacing the meniscal defect with any one of the disclosed compositions, wherein cells from the meniscus or surrounding tissues or fluids of the subject can migrate to and adhere to the engineered channels of the meniscal tissue of the composition.

Disclosed are methods of repairing at least one meniscal defect in a meniscus of a subject comprising replacing the meniscal defect with any one of the disclosed compositions, wherein the meniscal tissue of the composition comprises viable cells native to the meniscal tissue of the composition. In some instances, the meniscal tissue of the composition comprises 70% viable cells native to the meniscal tissue of the composition.

Disclosed are methods of repairing at least one meniscal defect in a meniscus of a subject comprising replacing the meniscal defect with any one of the disclosed compositions, wherein the subject is a mammal. In some instances, the subject can be a human.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the tool further comprises a securing mechanism configured to selectively secure the insert within the receptacle.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the tool further comprises a securing mechanism configured to selectively secure the insert within the receptacle, wherein the receptacle defines a bore, wherein the base portion of the insert has a first side wall that defines a recess, wherein, when the insert is received within the receptacle in the operative position, the bore of the receptacle is positioned in substantial alignment with the recess of the first side wall of the base portion relative to the longitudinal axis, wherein the securing mechanism comprises a screw that is positioned within the bore of the receptacle, and wherein, when the insert is received within the receptacle in the operative position, the screw is configured for axial advancement relative to the longitudinal axis until a distal portion of the screw is received within the recess of the first side wall of the base portion.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the receptacle has first and second guide walls that are spaced apart relative to the longitudinal axis.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the receptacle has first and second guide walls that are spaced apart relative to the longitudinal axis, further comprising an elongate body that extends outwardly from the second guide wall of the receptacle relative to the longitudinal axis. In some instances, the elongate body can comprise a ruler.

Disclosed are kits comprising any one or more of the disclosed compositions. For example, disclosed are kits comprising compositions comprising a meniscal tissue, wherein the meniscal tissue comprises one or more engineered channels. Disclosed are kits comprising compositions comprising a meniscal tissue, wherein the meniscal tissue comprises viable cells native to the meniscal tissue and devitalized blood vessels. Disclosed are kits comprising compositions comprising a meniscal tissue, wherein the meniscal tissue comprises greater than 30% viable non-immunogenic cells native to the meniscal tissue and less than 5% viable immunogenic cells. Disclosed are kits comprising compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells.

In some instances, the kit can further comprise at least one fixation device. In some instances, the kit can further comprise at least one cannula, trocar, or obturator. In some instances, the kit can further comprise a tool for cutting or shaving the meniscal tissue of the composition. In some instances, the kit can further comprise a tool for measuring the dimensions of a meniscus defect. In some instances, the kit can further comprise a tool for forming engineered channels in the composition.

Disclosed are kits comprising at least one of the disclosed compositions and further comprising a solution.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 4 shows a view of pin array and accompanying ruler.

FIG. 16 is a schematic drawing showing how to estimate the defect length.

FIG. 17 is a schematic drawing showing the radial cuts.

DETAILED DESCRIPTION

Figure 1:
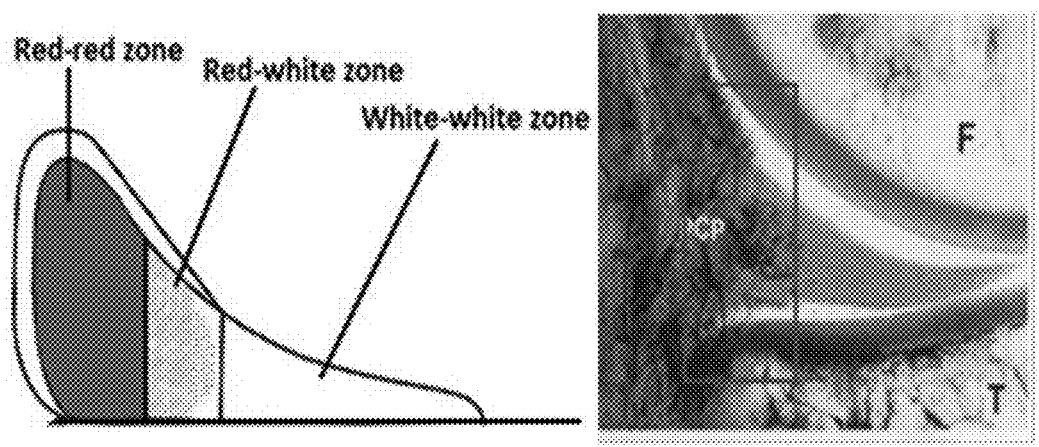
FIG. 1 shows images of vascular zones of the human meniscus (left) and the corresponding blood supply within these regions (right).

The disclosed method and compositions may be understood more readily by reference to the following detailed description of particular embodiments and the Examples included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. If a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "an engineered channel" includes a plurality of such engineered channels, reference to "the channel" is a reference to one or more engineered channels and equivalents thereof known to those skilled in the art, and so forth.

A "native meniscal red zone" as used herein refers to the outer most edge outer third of the width of a meniscus and is vascular, meaning it contains native blood vessels. A native meniscal red zone comprises viable blood vessels. "Viable blood vessels" as used herein are blood vessels that contain at least 5% viable endothelial cells. In some instances, a viable blood vessel comprises at least 50% viable and/or functional endothelial cells. In some instances, a viable blood vessel comprises at least 5, 10, 15, 20, 25, 30, 35, 40, 45, 50, 55, 60, 65, 70, 75, 80, 85, 90, or 95% or greater viable and/or functional endothelial cells.

A "native meniscal red-white zone" as used herein refers to the middle third or inner portion of the width of a meniscus and can be vascular, meaning it can contain native blood vessels. A native meniscal red-white zone can comprise viable blood vessels. In some instances, a viable blood vessel comprises at least 50% viable and/or functional endothelial cells. In some instances, a viable blood vessel in the red-white zone comprises at least 5, 10, 15, 20, 25, 30, 35, 40, 45, 50, 55, 60, 65, 70, 75, 80, 85, 90, or 95% or greater viable and/or functional endothelial cells.

An "altered red zone" as used herein refers to a red zone of a meniscal tissue that contains the physiological structures of a native meniscal red zone; however, an altered red zone has devitalized blood vessels. In some instances, an altered red zone comprises less than 5% viable and/or functional endothelial cells.

An "altered red-white zone" as used herein refers to a red-white zone of a meniscal tissue that contains the physiological structures of a native meniscal red-white zone; however, an altered red-white zone has devitalized blood vessels. In some instances, an altered red-white zone comprises less than 5% viable and/or functional endothelial cells.

"Engineered channel" as used herein refers to a non-naturally occurring, man-made channel. "Engineered channels" do not include tears or fissures that occur naturally from normal wear and tear of meniscal tissue. Optionally, engineered channels can be mechanically formed or produced. However, it is contemplated that engineered channels can be formed or produced by other means, including, for example and without limitation, lasers. In exemplary aspects, engineered channels can be formed by mechanical displacement of meniscal tissue. In other exemplary aspects, engineered channels can be formed by mechanical removal of meniscal tissue. In some instances, engineered channels are not chemically produced. Optionally, in exemplary aspects, engineered channels can comprise a primary engineered channel and at least one secondary engineered channel that branches out from and is positioned in fluid communication with the primary channel. In some aspects, it is contemplated that the longitudinal axis of each secondary engineered channel can be positioned at a selected angle relative to the longitudinal axis of the primary engineered channel. It is contemplated that two or more secondary channels can branch out from a primary engineered channel in any desired angular configuration, such as, for example and without limitation, a Y-shaped junction, a T-shaped junction, and the like. However, in other aspects, it is contemplated that at least one secondary engineered channel can have a longitudinal axis that is substantially parallel to and/or positioned in substantial alignment with the longitudinal axis of the primary engineered channel. In some exemplary aspects, engineered channels can extend substantially linearly; however, it is contemplated that engineered channels can also have a curved or arcuate profile if desired. As further disclosed herein, engineered channels can extend from the exterior surface of the outer edge of a meniscal tissue; however, it is contemplated that engineered channels can begin at and extend from any exterior surface of the meniscal tissue, including, for example, upper, lower, and side surfaces of the meniscal tissue that adjoin the exterior surface of the outer edge of the meniscal tissue. Optionally, in exemplary aspects, when engineered channels extend from multiple surfaces of the meniscal tissue, it is contemplated that at least one engineered channel that extends from a first exterior surface of the meniscal tissue can intersect with at least one other engineered channel that extends from a second exterior surface different than the first exterior surface of the meniscal tissue. Engineered channels can be produced in a controlled or specific manner. In some instances, engineered channels can be considered to be formed in a predictable manner, with a predictable and/or predetermined shape and configuration. Thus, in exemplary aspects, when a plurality of engineered channels are formed as disclosed herein, it is contemplated that at least a portion of the engineered channels can be substantially uniform in appearance. As used herein, a first engineered channel is "substantially uniform" to a second engineered channel when the longitudinal length of the first engineered channel is within 20% (above or below) of the longitudinal length of the second engineered channel. Optionally, it is contemplated that substantially uniform engineered channels can also have substantially the same diameter (maximum cross-sectional dimension), cross-sectional shape, taper profile, and the like. Optionally, in exemplary aspects, when a plurality of engineered channels are formed as disclosed herein, at least 20% of the engineered channels can be substantially uniform, with at least 20% of the engineered channels having respective longitudinal lengths that fall within 20% of the longitudinal length of a first engineered channel. In further exemplary aspects, at least 30%, at least 40%, at least 50%, at least 60%, at least 70%, at least 80%, or at least 90% of the engineered channels can be substantially uniform. Optionally, in further exemplary aspects, the longitudinal axes of at least a portion of the engineered channels can be substantially parallel to one another. For example, in these aspects, it is contemplated that the longitudinal axes of at least 20% of the engineered channels can be substantially parallel to one another. In further exemplary aspects, at least 30%, at least 40%, at least 50%, at least 60%, at least 70%, at least 80%, or at least 90% of the engineered channels can be substantially parallel to one another. In still further exemplary aspects, the longitudinal axes of substantially uniform engineered channels as disclosed herein can optionally be substantially parallel to one another. However, it is contemplated that engineered channels can be substantially uniform without being parallel to one another.

"Devitalized blood vessels" as used herein refers to blood vessels that have the physiological structural architecture of a viable blood vessel but have less than 5% viable endothelial cells within the blood vessels.

"Optional" or "optionally" as used herein refers to the subsequently described event, circumstance, or material may or may not occur or be present, and that the description includes instances where the event, circumstance, or material occurs or is present and instances where it does not occur or is not present.

"Meniscal defect" as used herein refers to a region or section of the native meniscus that has been damaged or has degenerated, or a physical absence of meniscal tissue resulting from a meniscectomy or genetic abnormality. A meniscal defect can involve <1% to 100% of the native meniscus. For example, a meniscal defect can be a meniscal tear resulting from acute trauma, a meniscal tear resulting from chronic trauma (wear and tear), a meniscal tear resulting from degeneration, an absence of meniscus tissue following a meniscectomy of part or the whole of the meniscus, or a naturally occurring absence of meniscus tissue not common to the typical physiology of a particular mammalian species, such as human.

"Subject" as used herein refers to a living individual with a meniscal defect. The term "subject" includes domesticated animals (e.g., cats, dogs, etc.), livestock (e.g., cattle, horses, pigs, sheep, goats, etc.), and laboratory animals (e.g., mouse, rabbit, rat, guinea pig, etc.). In one aspect, a subject is a mammal. In another aspect, a subject is a human. The term does not denote a particular age or sex. Thus, adult, child, adolescent and newborn subjects, whether male or female, are intended to be covered.

"Vascular access channels" as used herein refers to non-naturally occurring, man-made channels formed in the meniscus of a subject in need of a meniscal repair. For example, vascular access channels can be engineered channels formed in the meniscus of a subject in need of a meniscal repair. For example, vascular access channels can be formed through trephination of the subject's meniscus.

"Vascular zone" as used herein refers to a portion of the meniscus or meniscal tissue that comprises blood vessels. The vascular zone of a meniscus or meniscal tissue comprises a red zone of a meniscus or meniscal tissue, a red-white zone of a meniscus or meniscal tissue, a portion of a red zone of a meniscus or meniscal tissue, a portion of a red-white zone of a meniscus or meniscal tissue, or a combination thereof.

Ranges may be expressed herein as from "about" one particular value, and/or to "about" another particular value. When such a range is expressed, also specifically contemplated and considered disclosed is the range—from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Those skilled in the art will recognize, or be able to ascertain using no more than routine experimentation, many equivalents to the specific embodiments of the method and compositions described herein. Such equivalents are intended to be encompassed by the following claims.

B. Compositions Comprising Engineered Channels

Disclosed are compositions comprising a meniscal tissue, wherein the meniscal tissue comprises one or more engineered channels.

Disclosed are compositions comprising a meniscal tissue, wherein the meniscal tissue comprises one or more engineered channels, wherein the meniscal tissue further comprises a red zone or an altered red zone. In some instances, the meniscal tissue further comprises a red-white zone, and a white zone. The meniscal tissue can also comprise an altered red-white zone. The altered red zone and the altered red-white zone can comprise blood vessel structures native to the red zone and red-white zone, respectively.

Disclosed are compositions comprising a meniscal tissue, wherein the meniscal tissue comprises one or more engineered channels, wherein the meniscal tissue further comprises a red zone or an altered red zone, wherein the meniscal tissue has an inner edge and an opposed outer edge, and wherein the red zone or altered red zone has an outer surface that defines the outer edge of the meniscal tissue.

Disclosed are compositions comprising a meniscal tissue, wherein the meniscal tissue comprises one or more engineered channels, wherein the meniscal tissue further comprises a red zone or an altered red zone, a red-white zone, and a white zone, wherein the red zone or altered red zone, red-white zone, and white zone are in an orientation as present in native meniscal tissue. In the case of the altered red zone, the altered red zone is present in the orientation that a red zone is found in native meniscal tissue.

1. Engineered Channels

Disclosed are compositions comprising a meniscal tissue, wherein the meniscal tissue comprises one or more engineered channels, wherein the engineered channels are only present in a single zone of the meniscal tissue. For example, disclosed are compositions comprising a meniscal tissue, wherein the meniscal tissue comprises one or more engineered channels, wherein the engineered channels are only present in the red zone or altered red zone of the meniscal tissue. In some instances, the engineered channels are only present in the red zone and red-white zone, the altered red zone, the altered red-white zone, or the altered red zone and altered red-white zone of the meniscal tissue. In some instances, the engineered channels are not in the white zone.

Disclosed are compositions comprising a meniscal tissue, wherein the meniscal tissue comprises one or more engineered channels, wherein the meniscal tissue has an inner edge and an opposed outer edge, and wherein at least one engineered channel does not extend from the outer edge of the meniscal tissue to the inner edge of the meniscal tissue. Optionally, in exemplary aspects, the red zone or altered red zone of the meniscal tissue can define the outer edge of the meniscal tissue, and the white zone of the meniscal tissue can define the inner edge of the meniscal tissue. Thus, in these aspects, it is contemplated that at least one engineered channel does not extend completely through the red zone or altered red zone, the red-white zone or altered red-white zone, and the white zone.

Disclosed are compositions comprising a meniscal tissue, wherein the meniscal tissue comprises one or more engineered channels, wherein at least one engineered channel does not extend completely through the red zone or altered red zone. In other words, at least one engineered channel is contained solely within the red zone or altered red zone and does not extend into the red-white zone or altered red-white zone. Disclosed are compositions comprising a meniscal tissue, wherein the meniscal tissue comprises one or more engineered channels, wherein the meniscal tissue has an inner edge and an opposed outer edge, and wherein at least one engineered channel extends from the outer edge through only a portion of the altered red zone such that the at least one engineered channel does not reach the red-white zone or the white zone of the composition.

Disclosed are compositions comprising a meniscal tissue, wherein the meniscal tissue comprises one or more engineered channels, wherein the meniscal tissue has an inner edge and an opposed outer edge, wherein the inner edge is spaced from the outer edge in an inward direction, and wherein the engineered channels extend substantially in the inward direction. As used herein, the term "inward direction" generally refers to the direction of a line that extends substantially perpendicularly from a selected point on the outer edge of the meniscal tissue toward the inner edge of the meniscal tissue when the meniscal tissue is positioned in a relaxed position (i.e., no external force applied). As used herein, it is contemplated that engineered channels can extend substantially in the inward direction when they are positioned at an oblique angle (i.e., an acute or obtuse angle) relative to the outer edge of the meniscal tissue, provided the engineered channels generally extend toward a portion of the inner edge of the meniscal tissue. Alternatively, in exemplary non-limiting aspects, at least one engineered channel does not extend substantially in the inward direction. In these aspects, it is contemplated that the engineered channel can be positioned at an oblique angle that does not intersect with any portion of the inner edge when the meniscal tissue is positioned in the relaxed position.

Disclosed are compositions comprising a meniscal tissue, wherein the meniscal tissue comprises a plurality of engineered channels, wherein the meniscal tissue has an inner edge and an opposed outer edge, the outer edge having an exterior surface, wherein each engineered channel has a first end defined in the exterior surface of the outer edge of the meniscal tissue and an opposed second end defined within the red zone or altered red zone of the meniscal tissue, and wherein the first ends of the engineered channels are substantially evenly spaced about the exterior surface of the outer edge of the meniscal tissue. As used herein, the term "substantially evenly spaced" refers to a configuration of channels in which the first end of each channel is generally equally spaced from the first ends of its neighboring channels. In exemplary aspects, the engineered channels can be substantially evenly spaced when the first ends of the neighboring channels of the meniscal tissue are spaced apart by an average separation distance (measured center-to-center) and the separation distance between the first ends of each respective pair of neighboring channels falls within about 20% of the average separation distance. Alternatively, in exemplary non-limiting aspects, it is contemplated that the first ends of the engineered channels can be randomly spaced about the exterior surface of the outer edge of the meniscal tissue. Optionally, in still further exemplary aspects, the first ends of the engineered channels can be spaced apart in a configuration in which the separation distance between the first ends of neighboring channels is selectively varied to thereby produce a desired channel pattern.

Disclosed are compositions comprising a meniscal tissue, wherein the meniscal tissue comprises one or more engineered channels, wherein each engineered channel has a diameter ranging from about 0.05 mm to about 2 mm. In some instances, each engineered channel has a diameter ranging from about 0.008 mm to about 2 mm. In some instances, the high end of the range can be about 1 mm. In some instances, each engineered channel has a diameter ranging from about 0.008 mm to about 1 mm or from about 0.2 mm to about 1 mm. The diameter of the engineered channels is large enough for at least one cell to fit inside the engineered channel. The average size of most mammalian cells is 10-30 µm, therefore, the diameter of the engineered channels can be larger than 10-30 µm. In some instances, the diameter of the engineered channel can be 8 µm, which can be smaller than the size of a cell but still large enough for a cell to squeeze into the engineered channel. In some instances, the diameter of the engineered channels is large enough for multiple cells to fit inside the engineered channel. When determining diameter size, the height of the meniscal tissue should be considered. Engineered channels having diameters too much larger than 2 mm can lead to excessive tissue loss which can lead to weakening of the mechanical structure of the tissue and loss of tissue function.

Disclosed are compositions comprising a meniscal tissue, wherein the meniscal tissue comprises one or more engineered channels, wherein each engineered channel has a longitudinal axis, and wherein each engineered channel has a consistent diameter throughout the entire longitudinal length of the engineered channel. As used herein, the term "diameter" refers to the largest cross-sectional distance defined by the channel, and it is contemplated that the engineered can have any desired cross-sectional shape, including, for example and without limitation, a polygonal shape, such as a circle, an ellipse, a square, a rectangle, a rhombus, a trapezoid, and the like. The disclosed compositions can be attached to healthy meniscus in a subject to replace damaged tissue. The engineered channels within the meniscal tissue of the composition provide a greater surface area for the meniscal tissue. The greater surface area can allow for growth factors and cells from the subject's healthy meniscal tissue to contact the meniscal tissue of the composition in more places and allow for better integration of the meniscal tissue into the subject. The engineered channels also allow growth factors and cells preserved within the meniscal tissue to release from the meniscal tissue and contact the subject. In some instances, the diameter of an engineered channel can vary along the longitudinal length of the engineered channel. For example, the diameter of the engineered channel can get narrower or larger (e.g. cone shaped). In some instances, each engineered channel has a longitudinal axis, wherein at least one engineered channel has a diameter that varies moving along the longitudinal length of the engineered channel. In one exemplary aspect, at least a portion of at least one engineered channel can be inwardly tapered moving from the first end of the channel toward the second end of the channel such that the diameter of the channel decreases moving from the first end of the channel toward the second end of the channel. Alternatively, in another optional aspect, at least a portion of at least one engineered channel can be outwardly tapered moving from the first end of the channel toward the second end of the channel such that the diameter of the channel increases moving from the first end of the channel toward the second end of the channel. Optionally, in further exemplary aspects, the longitudinal axis of at least one engineered channel can be positioned at a selected angle (i.e., acute, perpendicular, or obtuse) relative to the longitudinal axis of at least one other engineered channel. In still further optional aspects, it is contemplated that the longitudinal axis of at least one engineered channel can be substantially parallel to the longitudinal axis of at least one other engineered channel.

Disclosed are compositions comprising a meniscal tissue, wherein the meniscal tissue comprises one or more engineered channels, wherein each engineered channel has a diameter, and wherein the diameter of at least one engineered channel is equal to the diameter of at least one other engineered channel. In some instances, the engineered channels can all have substantially the same diameter. In some instances, a portion of the engineered channels (i.e. a first group of channels) can all have substantially the same diameter and another portion of the engineered channels (i.e. a second group of channels) can all have substantially the same diameter wherein the at least two portions of engineered channels do not have the same diameter.

Disclosed are compositions comprising a meniscal tissue, wherein the meniscal tissue comprises one or more engineered channels, wherein each engineered channel has a longitudinal axis, and wherein each engineered channel has a longitudinal length ranging from about 0.2 mm to about 5 mm. In some instances, each engineered channel can have a longitudinal length ranging from about 0.1 mm to about 10 mm. Longitudinal lengths can vary. Longitudinal lengths can be based on the location of the engineered channel within the meniscal tissue. The engineered channels can be present in a vascular zone or altered vascular zone of the meniscal tissue. The vascular zone of the average human meniscus can be about 3-5 mm in length. In some aspects, the uppermost surface of the vascular zone is not as wide due to the triangular shape of the meniscus. Thus, engineered channels in the uppermost region of the vascular zone can have a shorter longitudinal length than engineered channels toward the middle region or lower region of the vascular zone. The longitudinal length can be based on the location of the engineered channel within the meniscal tissue. In some instances, the longitudinal length of an engineered channel can be as small as 0.1 mm.

Disclosed are compositions comprising a meniscal tissue, wherein the meniscal tissue comprises one or more engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length. In some instances, a portion of the engineered channels (i.e. a first group of channels) can all have substantially the same longitudinal length and another portion of the engineered channels (i.e. a second group of channels) can all have substantially the same longitudinal length, wherein the at least two portions of engineered channels do not have the same longitudinal length.

2. Size of Meniscal Tissue

Disclosed are compositions comprising a meniscal tissue, wherein the meniscal tissue comprises one or more engineered channels, wherein the meniscal tissue has an inner edge and an opposed outer edge, wherein the outer edge has a first end and an opposed second end, and wherein a first line extending from the first end of the outer edge to the second end of the outer edge has a length (i.e. chord length) ranging from about 5 mm to about 60 mm.

Also disclosed are compositions comprising a meniscal tissue, wherein the meniscal tissue comprises one or more engineered channels, wherein the meniscal tissue has an inner edge and an opposed outer edge, wherein the outer edge has a first end and an opposed second end, and wherein a first line extending from the first end of the outer edge to the second end of the outer edge has a length (i.e., chord length) ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm.

The length (i.e., chord length) of a first line extending from the first end of the outer edge to the second end of the outer edge can vary based on the desired size of the meniscal tissue. For example, a meniscal tissue that can cover about 50% defects in most people can have a first line extending from the first end of the outer edge to the second end of the outer edge having a length (i.e., chord length) ranging from about 25 mm to about 27 mm. Meniscal tissue around this size is designed for versatility because they can be used for treating both medial and lateral defects. However, smaller meniscal tissue pieces can have a first line extending from the first end of the outer edge to the second end of the outer edge having a length (i.e., chord length) of 5 mm.

The length of a second line extending perpendicularly from the center point to the first line can vary based on the desired size of the meniscal tissue. For example, a meniscal tissue that can cover about 50% defects in most people can have a second line extending perpendicularly from the center point to the first line that has a length ranging from about 9 mm to about 13 mm. Meniscal tissue around this size are designed for versatility because they can be used for treating both medial and lateral defects.

Figures 24A, 24B, 24C:
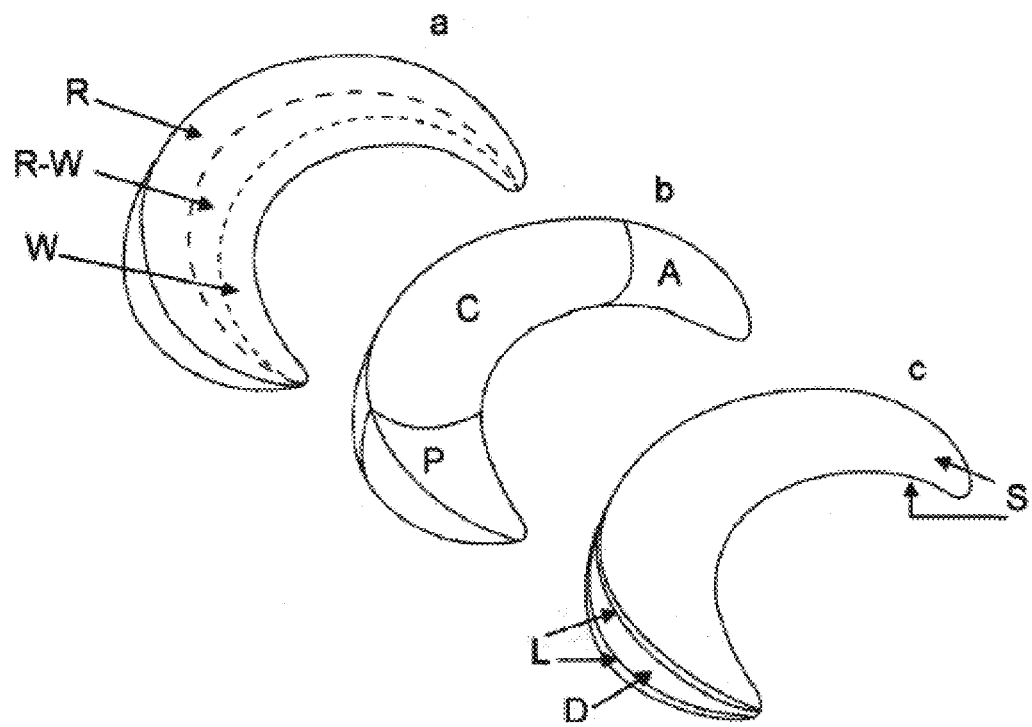
FIGS. 24A, 24B, and 24C show schematic diagrams of the spatial variations within the meniscus. A) vascular and avascular zones of the meniscus. The red zone (R) and the red-white zone (R-W) are vascularized. The white zone (W) is avascular. B) Topographical regions of the meniscus, posterior (P), central (C), and anterior (A). C) different depths of the meniscus. Surface (S), Lamellar layer (L), and deep zone (D).

In some instances, the size of the meniscal tissue of the compositions described herein is 10, 20, 30, 40, 50, 60, 70, 80, 90, or 100% of a full size, naturally-occurring meniscus. In other words, the meniscal tissue of the composition can be an entire, full length meniscus or can be a portion of full length meniscus. FIG. 24 shows a schematic of a full length meniscus. As described herein, the meniscal tissue of the composition can comprise the entire width of the red zone (R), red-white zone (R-W), and white zone (W) or a portion of one or more of red zone, red-white zone, and white zone. The red zone can also be referred to as the outer third. The red-white zone can also be referred to as the middle zone. The white zone can also be referred to as the inner zone.

The meniscal tissue of the compositions described herein can comprise the full length of a meniscus meaning it can comprise the anterior (A), central/middle (C), and posterior (P) regions of the meniscus or it can comprise a portion of one more of these regions (see FIG. 24). For example, meniscal tissue of the compositions described herein can comprise 1) all or a portion of the central region, 2) all or a portion of the central region and all or a portion of the posterior region, 3) all or a portion of the central region and all or a portion of the anterior region, 4) all or a portion of the central region and all or a portion of the posterior region and all or a portion of the anterior region, or 5) all or a portion of the anterior or posterior region.

FIG. 24 also shows the different depths of meniscal tissue. The meniscal tissue of the compositions described herein can comprise all the layers or a portion of the layers found in native meniscus. In some instances, the meniscal tissue of the compositions described herein can comprise the top surface layer, the top lamellar layer and all or a portion of the deep zone. In some instances, the meniscal tissue of the compositions described herein can comprise the bottom surface layer, the bottom lamellar layer and all or a portion of the deep zone.

3. Native Factors in the Meniscal Tissue

Disclosed are compositions comprising a meniscal tissue, wherein the meniscal tissue comprises one or more engineered channels, wherein the meniscal tissue comprises viable cells native to the meniscal tissue. In some instances, the meniscal tissue comprises at least 70% viable cells native to the meniscal tissue. In some instances, the meniscal tissue comprises at least 20, 30, 40, 50, 60, 70, 80, or 90% viable cells native to the meniscal tissue. In some instances, at least a portion of the viable cells native to the meniscal tissue are of mesenchymal origin. For example, in some instances at least a portion of the viable cells native to the meniscal tissue of mesenchymal origin are mesenchymal stem cells (MSCs).

Disclosed are compositions comprising a meniscal tissue, wherein the meniscal tissue comprises one or more engineered channels, wherein the composition is not immunogenic. As used herein, a composition is immunogenic if it produces >100 pg/mL of TNF upon stimulation with a bacterial immunogen, such as lipopolysaccharide (LPS), within about 24 hours of culture. FACs analysis can be used to determine the presence or absence of immunogenic cells. If <5% of viable cells are positive for the hematopoietic cell marker, CD45, and/or the endothelial cell marker, CD31, then the composition can be considered absent of immunogenic cells. An absence of immunogenic cells can be further confirmed if it does not produce >100 pg/ml of TNF upon stimulation with a bacterial immunogen, such as lipopolysaccharide (LPS), within about 24 hours of culture. In some instances, >5% of cells present in the composition can be immune cells however the composition would be considered absent of immunogenic cells if <5% of the viable cells are immune cells.

Disclosed are compositions comprising a meniscal tissue, wherein the meniscal tissue comprises one or more engineered channels, wherein the meniscal tissue comprises growth factors native to the meniscal tissue. The growth factors can be one or more of TGF-β1, TGF-b3, bFGF, PDGF-AB, PDGF-BB, IGF-1, HGF, BMP-7, EGF, CTGF, BMP-2, BMP-6, and VEGF.

Disclosed are compositions comprising a meniscal tissue, wherein the meniscal tissue comprises one or more engineered channels further comprising exogenous cells, growth factors, or proteins. Exogenous cells can be cultured cells or cells that are obtained from a tissue other than the meniscal tissue of the composition.

Disclosed are compositions comprising a meniscal tissue, wherein the meniscal tissue comprises one or more engineered channels, wherein the composition does not comprise fatty, immunogenic connective tissue. In some instances, the fatty, immunogenic connective tissue can be from the joint capsule.

Disclosed are compositions comprising a meniscal tissue, wherein the meniscal tissue comprises one or more engineered channels, wherein the meniscal tissue does not comprise hematopoietic cells. In some instances, not comprising hematopoietic cells can mean that <5% of the total cells in the meniscal tissue are hematopoietic. Disclosed are compositions comprising a meniscal tissue, wherein the meniscal tissue comprises one or more engineered channels, wherein the meniscal tissue does not comprise hematopoietic cells but does comprise cells of mesenchymal origin, such as MSCs.

Disclosed are compositions comprising a meniscal tissue, wherein the meniscal tissue comprises one or more engineered channels, wherein the meniscal tissue comprises all collagen layers of human meniscus. Also disclosed are compositions comprising a meniscal tissue, wherein the meniscal tissue comprises one or more engineered channels, wherein the meniscal tissue comprises at least one of the collagen layers of human meniscus. In some instances, multiple collagen layers are present in the meniscal tissue of the composition but still less than all of the collagen layers normally found in human meniscus. Human meniscus comprises a superficial layer, a lamellar layer, and deep layers. Therefore, disclosed are compositions comprising a meniscal tissue, wherein the meniscal tissue comprises one or more engineered channels, wherein the meniscal tissue comprises all collagen layers of a human meniscus, wherein the collagen layers comprise a superficial layer, a lamellar layer, and deep layers. In some instances, the collagen layers comprise random collagen fibers, radial tie fibers, and circumferential collagen fibers.

In some instances, the meniscal tissue of the composition does not comprise exogenous cells or cells that are not native to that tissue. In other words, in some instances any cells present in the meniscal tissue of the composition are cells native to the meniscal tissue.

4. Cryopreservation

Disclosed are compositions comprising a meniscal tissue, wherein the meniscal tissue comprises one or more engineered channels, wherein the meniscal tissue is cryopreserved. In some instances, the viability of the cells is substantially maintained for at least about 24 months when stored frozen Disclosed are compositions comprising a meniscal tissue, wherein the meniscal tissue comprises one or more engineered channels further comprising a cryopreservation solution.

Also disclosed are previously cryopreserved compositions comprising a meniscal tissue, wherein the meniscal tissue comprises one or more engineered channels as described herein. Previously cryopreserved means that the composition has been thawed from its cryopreserved state.

C. Compositions Comprising Less than 5% Viable Endothelial Cells

Disclosed are compositions comprising a meniscal tissue, wherein the meniscal tissue comprises viable cells native to the meniscal tissue and devitalized blood vessels.

Disclosed are compositions comprising a meniscal tissue, wherein the meniscal tissue comprises viable cells native to the meniscal tissue and devitalized blood vessels, wherein the meniscal tissue further comprises an altered red zone. In some instances, the meniscal tissue further comprises a red-white zone, and a white zone. The meniscal tissue can also comprise an altered red-white zone. The altered red zone and the altered red-white zone can comprise blood vessel structures native to the red zone and red-white zone, respectively.

Disclosed are compositions comprising a meniscal tissue, wherein the meniscal tissue comprises viable cells native to the meniscal tissue and devitalized blood vessels, wherein the meniscal tissue further comprises an altered red zone, wherein the meniscal tissue has an inner edge and an opposed outer edge, and wherein the altered red zone has an outer surface that defines the outer edge of the meniscal tissue.

Disclosed are compositions comprising a meniscal tissue, wherein the meniscal tissue comprises viable cells native to the meniscal tissue and devitalized blood vessels, wherein the meniscal tissue further comprises an altered red zone, a red-white zone, and a white zone, wherein the altered red zone, red-white zone, and white zone are in an orientation as present in native meniscal tissue. For example, the altered red zone is present in the orientation that a red zone is found in native meniscal tissue.

Also disclosed are compositions comprising a meniscal tissue, wherein the meniscal tissue comprises greater than 30% viable non-immunogenic cells native to the meniscal tissue and less than 5% viable immunogenic cells. In some instances, the meniscal tissue comprises at least 20, 30, 40, 50, 60, 70, 80, or 90% viable non-immunogenic cells native to the meniscal tissue.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises an altered red zone. In some instances, the meniscal tissue further comprises a red-white zone, and a white zone. The meniscal tissue can also comprise an altered red-white zone. The altered red zone and the altered red-white zone can comprise blood vessel structures native to the red zone and red-white zone, respectively.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises an altered red zone, wherein the meniscal tissue has an inner edge and an opposed outer edge, and wherein the altered red zone has an outer surface that defines the outer edge of the meniscal tissue.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises an altered red zone, a red-white zone, and a white zone, wherein the altered red zone, red-white zone, and white zone are in an orientation as present in native meniscal tissue.

1. Engineered Channels

Disclosed are compositions comprising a meniscal tissue, wherein the meniscal tissue comprises viable cells native to the meniscal tissue and devitalized blood vessels, wherein the meniscal tissue further comprises engineered channels.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, wherein the engineered channels are only present in the altered red zone. In some instances, the meniscal tissue further comprises and altered red-white zone, wherein the engineered channels are only present in the altered red zone and altered red-white zone.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, an altered red-white zone, and a white zone wherein the meniscal tissue has an inner edge and an opposed outer edge, and wherein at least one engineered channel does not extend from the outer edge of the meniscal tissue to the inner edge of the meniscal tissue. Optionally, in exemplary aspects, the red zone or altered red zone of the meniscal tissue can define the outer edge of the meniscal tissue, and the white zone of the meniscal tissue can define the inner edge of the meniscal tissue. Thus, in these aspects, it is contemplated that at least one engineered channel does not extend completely through the red zone, the red-white zone, and the white zone.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, altered red-white zone, and white zone, wherein at least one engineered channel does not extend completely through the altered red zone. For example, at least one engineered channel is contained solely within the altered red zone and does not extend into the altered red-white zone. Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, wherein the meniscal tissue has an inner edge and an opposed outer edge, and wherein at least one engineered channel extends from the outer edge through only a portion of the altered red zone such that the at least one engineered channel does not reach the red-white zone or the white zone of the composition.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue has an inner edge and an opposed outer edge, wherein the inner edge is spaced from the outer edge in an inward direction, and wherein the engineered channels extend substantially in the inward direction. As used herein, the term "inward direction" generally refers to the direction of a line that extends substantially perpendicularly from a selected point on the outer edge of the meniscal tissue toward the inner edge of the meniscal tissue when the meniscal tissue is positioned in a relaxed position (i.e., no external force applied). As used herein, it is contemplated that engineered channels can extend substantially in the inward direction when they are positioned at an oblique angle (i.e., an acute or obtuse angle) relative to the outer edge of the meniscal tissue, provided the engineered channels generally extend toward a portion of the inner edge of the meniscal tissue. Alternatively, in exemplary non-limiting aspects, at least one engineered channel does not extend substantially in the inward direction. In these aspects, it is contemplated that the engineered channel can be positioned at an oblique angle that does not intersect with any portion of the inner edge when the meniscal tissue is positioned in the relaxed position.

Disclosed are compositions comprising a meniscal tissue, wherein the meniscal tissue comprises viable cells native to the meniscal tissue and devitalized blood vessels, wherein the meniscal tissue further comprises engineered channels, wherein the meniscal tissue further comprises an altered red zone, wherein the meniscal tissue has an inner edge and an opposed outer edge, the outer edge having an exterior surface, wherein each engineered channel has a first end defined in the exterior surface of the outer edge of the meniscal tissue and an opposed second end defined within the altered red zone of the meniscal tissue, and wherein the first ends of the engineered channels are substantially evenly spaced about the exterior surface of the outer edge of the meniscal tissue. As used herein, the term "substantially evenly spaced" refers to a configuration of channels in which the first end of each channel is generally equally spaced from the first ends of its neighboring channels. In exemplary aspects, the engineered channels can be substantially evenly spaced when the first ends of the neighboring channels of the meniscal tissue are spaced apart by an average separation distance (measured center-to-center) and the separation distance between the first ends of each respective pair of neighboring channels falls within about 20% of the average separation distance. Alternatively, in exemplary non-limiting aspects, it is contemplated that the first ends of the engineered channels can be randomly spaced about the exterior surface of the outer edge of the meniscal tissue. Optionally, in still further exemplary aspects, the first ends of the engineered channels can be spaced apart in a configuration in which the separation distance between the first ends of neighboring channels is selectively varied to thereby produce a desired channel pattern.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a diameter ranging from about 0.05 mm to about 2 mm. In some instances, each engineered channel has a diameter ranging from about 0.008 mm to about 2 mm. In some instances, the high end of the range can be about 1 mm. In some instances, each engineered channel has a diameter ranging from about 0.008 mm to about 1 mm or from about 0.2 mm to about 1 mm. The diameter of the engineered channels is large enough for at least one cell to fit inside the engineered channel. The average size of most mammalian cells is 10-30 µm, therefore, the diameter of the engineered channels can be larger than 10-30 µm. In some instances, the diameter of the engineered channel can be 8 µm, which can be smaller than the size of a cell but still larger enough for a cell to squeeze into the engineered channel. In some instances, the diameter of the engineered channels is large enough for multiple cells to fit inside the engineered channel. When determining diameter size, the height of the meniscal tissue should be considered. Engineered channels having diameters too much larger than 2 mm can lead to excessive tissue loss which can lead to weakening of the mechanical structure of the tissue and loss of tissue function.

Disclosed are compositions comprising meniscal tissue, wherein the meniscal tissue comprises viable cells native to the meniscal tissue and devitalized blood vessels, wherein the meniscal tissue further comprises engineered channels, wherein each engineered channel has a longitudinal axis, and wherein each engineered channel has a consistent diameter throughout the entire longitudinal length of the engineered channel. As used herein, the term "diameter" refers to the largest cross-sectional distance defined by the channel, and it is contemplated that the engineered can have any desired cross-sectional shape, including, for example and without limitation, a polygonal shape, such as a circle, an ellipse, a square, a rectangle, a rhombus, a trapezoid, and the like. The disclosed compositions can be attached to healthy meniscus in a subject to replace damaged tissue. The engineered channels within the meniscal tissue of the composition provide a greater surface area for the meniscal tissue. The greater surface area can allow for growth factors and cells from the subject's healthy meniscal tissue to contact the meniscal tissue of the composition in more places and allow for better integration of the meniscal tissue into the subject. The engineered channels also allow growth factors and cells present in the meniscal tissue to release from the meniscal tissue and contact the subject. In some instances, the diameter of an engineered channel can vary along the longitudinal length of the engineered channel. For example, the diameter of the engineered channel can get narrower or larger (e.g. cone shaped). In some instances, each engineered channel has a longitudinal axis, wherein at least one engineered channel has a diameter that varies moving along the longitudinal length of the engineered channel. In one exemplary aspect, at least a portion of at least one engineered channel can be inwardly tapered moving from the first end of the channel toward the second end of the channel such that the diameter of the channel decreases moving from the first end of the channel toward the second end of the channel. Alternatively, in another optional aspect, at least a portion of at least one engineered channel can be outwardly tapered moving from the first end of the channel toward the second end of the channel such that the diameter of the channel increases moving from the first end of the channel toward the second end of the channel. Optionally, in further exemplary aspects, the longitudinal axis of at least one engineered channel can be positioned at a selected angle (i.e., acute, perpendicular, or obtuse) relative to the longitudinal axis of at least one other engineered channel. In still further optional aspects, it is contemplated that the longitudinal axis of at least one engineered channel can be substantially parallel to the longitudinal axis of at least one other engineered channel.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a diameter, and wherein the diameter of at least one engineered channel is equal to the diameter of at least one other engineered channel. In some instances, the engineered channels can all have substantially the same diameter. In some instances, a portion of the engineered channels (i.e., a first group of channels) can all have substantially the same diameter and another portion of the engineered channels (i.e., a second group of channels) can all have substantially the same diameter wherein the at least two portions of engineered channels do not have the same diameter.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a longitudinal axis, and wherein each engineered channel has a longitudinal length ranging from about 0.2 mm to about 5 mm. In some instances, each engineered channel can have a longitudinal length ranging from about 0.1 mm to about 10 mm. Longitudinal lengths can vary. Longitudinal lengths can be based on the location of the engineered channel within the meniscal tissue. The engineered channels can be present in a vascular zone or altered vascular zone of the meniscal tissue. The vascular zone of the average human meniscus can be about 3-5 mm in length. In some aspects, the uppermost surface of the vascular zone is not as wide due to the triangular shape of the meniscus. Thus, engineered channels in the uppermost region of the vascular zone can have a shorter longitudinal length than engineered channels toward the middle region or lower region of the vascular zone. The longitudinal length can be based on the location of the engineered channel within the meniscal tissue. In some instances, the longitudinal length of an engineered channel can be as small as 0.1 mm.

Disclosed are compositions comprising a meniscal tissue, wherein the meniscal tissue comprises viable cells native to the meniscal tissue and devitalized blood vessels, wherein the meniscal tissue further comprises engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length. In some instances, a portion of the engineered channels (i.e., a first group of channels) can all have substantially the same longitudinal length and another portion of the engineered channels (i.e., a second group of channels) can all have substantially the same longitudinal length, wherein the at least two portions of engineered channels do not have the same longitudinal length.

Also disclosed are compositions comprising a meniscal tissue comprising greater than 30% viable non-immunogenic cells native to the meniscal tissue and less than 5% viable immunogenic cells, wherein the meniscal tissue further comprises engineered channels.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, wherein the engineered channels are only present in the altered red zone. In some instances, the meniscal tissue further comprises and altered red-white zone, wherein the engineered channels are only present in the altered red zone and altered red-white zone.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, an altered red-white zone, and a white zone wherein the meniscal tissue has an inner edge and an opposed outer edge, and wherein at least one engineered channel does not extend from the outer edge of the meniscal tissue to the inner edge of the meniscal tissue. Optionally, in exemplary aspects, the altered red zone of the meniscal tissue can define the outer edge of the meniscal tissue, and the white zone of the meniscal tissue can define the inner edge of the meniscal tissue. Thus, in these aspects, it is contemplated that at least one engineered channel does not extend completely through the altered red zone, the altered red-white zone, and the white zone.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, altered red-white zone, and white zone, wherein at least one engineered channel does not extend completely through the altered red zone. In other words, at least one engineered channel is contained solely within the altered red zone and does not extend into the altered red-white zone. Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, wherein the meniscal tissue has an inner edge and an opposed outer edge, and wherein at least one engineered channel extends from the outer edge through only a portion of the altered red zone such that the at least one engineered channel does not reach the red-white zone or the white zone of the composition.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue has an inner edge and an opposed outer edge, wherein the inner edge is spaced from the outer edge in an inward direction, and wherein the engineered channels extend substantially in the inward direction. As used herein, the term "inward direction" generally refers to the direction of a line that extends substantially perpendicularly from a selected point on the outer edge of the meniscal tissue toward the inner edge of the meniscal tissue when the meniscal tissue is positioned in a relaxed position (i.e., no external force applied). As used herein, it is contemplated that engineered channels can extend substantially in the inward direction when they are positioned at an oblique angle (i.e., an acute or obtuse angle) relative to the outer edge of the meniscal tissue, provided the engineered channels generally extend toward a portion of the inner edge of the meniscal tissue. Alternatively, in exemplary non-limiting aspects, at least one engineered channel does not extend substantially in the inward direction. In these aspects, it is contemplated that the engineered channel can be positioned at an oblique angle that does not intersect with any portion of the inner edge when the meniscal tissue is positioned in the relaxed position.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein the meniscal tissue further comprises an altered red zone, wherein the meniscal tissue has an inner edge and an opposed outer edge, the outer edge having an exterior surface, wherein each engineered channel has a first end defined in the exterior surface of the outer edge of the meniscal tissue and an opposed second end defined within the altered red zone of the meniscal tissue, and wherein the first ends of the engineered channels are substantially evenly spaced about the exterior surface of the outer edge of the meniscal tissue. As used herein, the term "substantially evenly spaced" refers to a configuration of channels in which the first end of each channel is generally equally spaced from the first ends of its neighboring channels. In exemplary aspects, the engineered channels can be substantially evenly spaced when the first ends of the neighboring channels of the meniscal tissue are spaced apart by an average separation distance (measured center-to-center) and the separation distance between the first ends of each respective pair of neighboring channels falls within about 20% of the average separation distance. Alternatively, in exemplary non-limiting aspects, it is contemplated that the first ends of the engineered channels can be randomly spaced about the exterior surface of the outer edge of the meniscal tissue. Optionally, in still further exemplary aspects, the first ends of the engineered channels can be spaced apart in a configuration in which the separation distance between the first ends of neighboring channels is selectively varied to thereby produce a desired channel pattern. Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a diameter ranging from about 0.05 mm to about 2 mm. In some instances, each engineered channel has a diameter ranging from about 0.008 mm to about 2 mm. In some instances, the high end of the range can be about 1 mm. In some instances, each engineered channel has a diameter ranging from about 0.008 mm to about 1 mm or from about 0.2 mm to about 1 mm. The diameter of the engineered channels is large enough for at least one cell to fit inside the engineered channel. The average size of most mammalian cells is 10-30 µm, therefore, the diameter of the engineered channels can be larger than 10-30 µm. In some instances, the diameter of the engineered channel can be 8 µm, which can be smaller than the size of a cell but still larger enough for a cell to squeeze into the engineered channel. In some instances, the diameter of the engineered channels is large enough for multiple cells to fit inside the engineered channel. When determining diameter size, the height of the meniscal tissue should be considered. Engineered channels having diameters too much larger than 2 mm can lead to excessive tissue loss which can lead to weakening of the mechanical structure of the tissue and loss of tissue function.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a longitudinal axis, and wherein each engineered channel has a consistent diameter throughout the entire longitudinal length of the engineered channel. As used herein, the term "diameter" refers to the largest cross-sectional distance defined by the channel, and it is contemplated that the engineered can have any desired cross-sectional shape, including, for example and without limitation, a polygonal shape, such as a circle, an ellipse, a square, a rectangle, a rhombus, a trapezoid, and the like. The disclosed compositions can be attached to healthy meniscus in a subject to replace damaged tissue. The engineered channels within the meniscal tissue of the composition provide a greater surface area for the meniscal tissue. The greater surface area can allow for growth factors and cells from the subject's healthy meniscal tissue to contact the meniscal tissue of the composition in more places and allow for better integration of the meniscal tissue into the subject. The engineered channels also allow growth factors and cells present in the meniscal tissue to release from the meniscal tissue and contact the subject. In some instances, the diameter of an engineered channel can vary along the longitudinal length of the engineered channel. For example, the diameter of the engineered channel can get narrower or larger (e.g. cone shaped). In some instances, each engineered channel has a longitudinal axis, wherein at least one engineered channel has a diameter that varies moving along the longitudinal length of the engineered channel. In one exemplary aspect, at least a portion of at least one engineered channel can be inwardly tapered moving from the first end of the channel toward the second end of the channel such that the diameter of the channel decreases moving from the first end of the channel toward the second end of the channel. Alternatively, in another optional aspect, at least a portion of at least one engineered channel can be outwardly tapered moving from the first end of the channel toward the second end of the channel such that the diameter of the channel increases moving from the first end of the channel toward the second end of the channel. Optionally, in further exemplary aspects, the longitudinal axis of at least one engineered channel can be positioned at a selected angle (i.e., acute, perpendicular, or obtuse) relative to the longitudinal axis of at least one other engineered channel. In still further optional aspects, it is contemplated that the longitudinal axis of at least one engineered channel can be substantially parallel to the longitudinal axis of at least one other engineered channel.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a diameter, and wherein the diameter of at least one engineered channel is equal to the diameter of at least one other engineered channel. In some instances, the engineered channels can all have substantially the same diameter. In some instances, a portion of the engineered channels (i.e., a first group of channels) can all have substantially the same diameter and another portion of the engineered channels (i.e., a second group of channels) can all have substantially the same diameter wherein the at least two portions of engineered channels do not have the same diameter.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a longitudinal axis, and wherein each engineered channel has a longitudinal length ranging from about 0.2 mm to about 5 mm. In some instances, each engineered channel can have a longitudinal length ranging from about 0.1 mm to about 10 mm. Longitudinal lengths can vary. Longitudinal lengths can be based on the location of the engineered channel within the meniscal tissue. The engineered channels can be present in a vascular zone or altered vascular zone of the meniscal tissue. The vascular zone of the average human meniscus can be about 3-5 mm in length. In some aspects, the uppermost surface of the vascular zone is not as wide due to the triangular shape of the meniscus. Thus, engineered channels in the uppermost region of the vascular zone can have a shorter longitudinal length than engineered channels toward the middle region or lower region of the vascular zone. The longitudinal length can be based on the location of the engineered channel within the meniscal tissue. In some instances, the longitudinal length of an engineered channel can be as small as 0.1 mm.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue further comprises engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length. In some instances, a portion of the engineered channels (i.e., a first group of channels) can all have substantially the same longitudinal length and another portion of the engineered channels (i.e., a second group of channels) can all have substantially the same longitudinal length, wherein the at least two portions of engineered channels do not have the same longitudinal length.

2. Size of Meniscal Tissue

Disclosed are compositions comprising a meniscal tissue, wherein the meniscal tissue comprises viable cells native to the meniscal tissue and devitalized blood vessels, wherein the meniscal tissue has an inner edge and an opposed outer edge, wherein the outer edge has a first end and an opposed second end, and wherein a first line extending from the first end of the outer edge to the second end of the outer edge has a length (i.e., chord length) ranging from about 5 mm to about 60 mm.

Disclosed are compositions comprising a meniscal tissue, wherein the meniscal tissue comprises viable cells native to the meniscal tissue and devitalized blood vessels, wherein the meniscal tissue has an inner edge and an opposed outer edge, wherein the outer edge has a first end and an opposed second end, and wherein a first line extending from the first end of the outer edge to the second end of the outer edge has a length (i.e., chord length) ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm.

Also disclosed are compositions comprising a meniscal tissue, wherein the meniscal tissue comprises greater than 30% viable non-immunogenic cells native to the meniscal tissue and less than 5% viable immunogenic cells, wherein the meniscal tissue has an inner edge and an opposed outer edge, wherein the outer edge has a first end and an opposed second end, and wherein a first line extending from the first end of the outer edge to the second end of the outer edge has a length (i.e., chord length) ranging from about 5 mm to about 60 mm.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue has an inner edge and an opposed outer edge, wherein the outer edge has a first end and an opposed second end, and wherein a first line extending from the first end of the outer edge to the second end of the outer edge has a length (i.e., chord length) ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm The distance of a first line extending from the first end of the outer edge to the second end of the outer edge can vary based on the desired size of the meniscal tissue. For example, a meniscal tissue that can cover about 50% defects in most people can have a first line extending from the first end of the outer edge to the second end of the outer edge having a distance ranging from about 25 mm to about 27 mm. Meniscal tissue around this size can provide greater versatility because they can be used for treating both medial and lateral defects. However, smaller meniscal tissue pieces can have a first line extending from the first end of the outer edge to the second end of the outer edge having a distance of 5 mm. The length of a second line extending perpendicularly from the center point to the first line can vary based on the desired size of the meniscal tissue. For example, a meniscal tissue that can cover about 50% defects in most people can have a second line extending perpendicularly from the center point to the first line that has a length ranging from about 9 mm to about 13 mm. Meniscal tissues around this size are designed for versatility because they can be used for treating both medial and lateral defects.

In some instances, the size of the meniscal tissue of the composition is 10, 20, 30, 40, 50, 60, 70, 80, 90, or 100% of a full size, naturally-occurring meniscus. In other words, the meniscal tissue of the composition can be an entire, full length meniscus or can be a portion of full length meniscus. FIG. 24 shows a schematic of a full length meniscus. As described herein, the meniscal tissue of the composition can comprise the entire width of the red zone (R), red-white zone (R-W), and white zone (W) or a portion of one or more of red zone, red-white zone, and white zone. The red zone can also be referred to as the outer third. The red-white zone can also be referred to as the middle zone. The white zone can also be referred to as the inner zone.

The meniscal tissue of the composition can comprise the full length of a meniscus meaning it can comprise the anterior (A), central/middle (C), and posterior (P) regions of the meniscus or it can comprise a portion of one more of these regions (see FIG. 24) For example, meniscal tissue of the composition can comprise 1) all or a portion of the central region, 2) all or a portion of the central region and all or a portion of the posterior region, 3) all or a portion of the central region and all or a portion of the anterior region, 4) all or a portion of the central region and all or a portion of the posterior region and all or a portion of the anterior region, or 5) all or a portion of the anterior or posterior region.

FIG. 24 also shows the different depths of meniscal tissue. The meniscal tissue of the composition can comprise all the layers or a portion of the layers found in native meniscus. In some instances, the meniscal tissue of the composition can comprise the top surface layer, the top lamellar layer and all or a portion of the deep zone. In some instances, the meniscal tissue of the composition can comprise the bottom surface layer, the bottom lamellar layer and all or a portion of the deep zone.

3. Native Factors in Meniscal Tissue

Disclosed are compositions comprising a meniscal tissue, wherein the meniscal tissue comprises viable cells native to the meniscal tissue and devitalized blood vessels. In some instances, the meniscal tissue comprises at least 70% viable cells native to the meniscal tissue. In some instances, the meniscal tissue comprises at least 20, 30, 40, 50, 60, 70, 80, or 90% viable cells native to the meniscal tissue. In some instances, at least a portion of the viable cells native to the meniscal tissue are of mesenchymal origin. For example, in some instances at least a portion of the viable cells native to the meniscal tissue of mesenchymal origin are MSCs.

Disclosed are compositions comprising a meniscal tissue, wherein the meniscal tissue comprises viable cells native to the meniscal tissue and devitalized blood vessels, wherein the composition is not immunogenic. A composition is immunogenic if it produces >100 pg/mL of TNF upon stimulation with a bacterial immunogen, such as LPS, within about 24 hours of culture. FACs analysis can be used to determine the presence or absence of immunogenic cells. If <5% of viable cells are positive for the hematopoietic cell marker, CD45, and/or the endothelial cell marker, CD31, then the composition can be considered absent of immunogenic cells. An absence of immunogenic cells can be further confirmed if it does not produce >100 pg/ml of TNF upon stimulation with a bacterial immunogen, such as lipopolysaccharide (LPS), within about 24 hours of culture. In some instances, >5% of cells present in the composition can be immune cells however the composition would be considered absent of immunogenic cells if <5% of the viable cells are immune cells.

Disclosed are compositions comprising a meniscal tissue, wherein the meniscal tissue comprises viable cells native to the meniscal tissue and devitalized blood vessels, wherein the meniscal tissue comprises growth factors native to the meniscal tissue. The growth factors can be one or more of TGF-β1, TGF-b3, bFGF, PDGF-AB, PDGF-BB, IGF-1, HGF, BMP-7, EGF, CTGF, BMP-2, BMP-6, and VEGF.

Disclosed are compositions comprising a meniscal tissue, wherein the meniscal tissue comprises viable cells native to the meniscal tissue and devitalized blood vessels further comprising exogenous cells, growth factors, or proteins. Exogenous cells can be cultured cells or cells that originated from a different tissue.

Disclosed are compositions comprising a meniscal tissue, wherein the meniscal tissue comprises viable cells native to the meniscal tissue and devitalized blood vessels, wherein the composition does not comprise fatty, immunogenic connective tissue. In some instances, the fatty, immunogenic connective tissue can be from the joint capsule.

Disclosed are compositions comprising a meniscal tissue, wherein the meniscal tissue comprises viable cells native to the meniscal tissue and devitalized blood vessels, wherein the meniscal tissue does not comprise hematopoietic cells. In some instances, not comprising hematopoietic cells can mean that <5% of the total cells in the meniscal tissue are hematopoietic. Disclosed are compositions comprising a meniscal tissue, wherein the meniscal tissue comprises viable cells native to the meniscal tissue and devitalized blood vessels, wherein the meniscal tissue does not comprise hematopoietic cells but does comprise cells of mesenchymal origin, such as MSCs.

Disclosed are compositions comprising a meniscal tissue, wherein the meniscal tissue comprises viable cells native to the meniscal tissue and devitalized blood vessels, wherein the meniscal tissue comprises all collagen layers of human meniscus. Also disclosed are compositions comprising a meniscal tissue, wherein the meniscal tissue comprises viable cells native to the meniscal tissue and devitalized blood vessels, wherein the meniscal tissue comprises at least one of the collagen layers of human meniscus. In some instances, multiple collagen layers are present in the meniscal tissue of the composition but still less than all of the collagen layers normally found in human meniscus. Human meniscus comprises a superficial layer, a lamellar layer, and deep layers. Therefore, disclosed are compositions comprising a meniscal tissue comprising viable cells native to the meniscal tissue and devitalized blood vessels, wherein the meniscal tissue comprises all collagen layers of human meniscus, wherein the collagen layers comprise a superficial layer, a lamellar layer, and deep layers. In some instances, the collagen layers comprise random collagen fibers, radial tie fibers, and circumferential collagen fibers.

Also disclosed are compositions comprising a meniscal tissue, wherein the meniscal tissue comprises greater than 30% viable non-immunogenic cells native to the meniscal tissue and less than 5% viable immunogenic cells. In some instances, the meniscal tissue comprises at least 70% viable cells native to the meniscal tissue. In some instances, the meniscal tissue comprises at least 20, 30, 40, 50, 60, 70, 80, or 90% viable cells native to the meniscal tissue. In some instances, at least a portion of the viable cells native to the meniscal tissue are of mesenchymal origin. For example, in some instances at least a portion of the viable cells native to the meniscal tissue of mesenchymal origin are MSCs.

Disclosed are compositions comprising a meniscal tissue, wherein the meniscal tissue comprises greater than 30% viable non-immunogenic cells native to the meniscal tissue and less than 5% viable immunogenic cells, wherein the composition is not immunogenic. A composition is immunogenic if it produces >100 pg/mL of TNF upon stimulation with a bacterial immunogen, such as a lipopolysaccharide (LPS), within about 24 hours of culture. FACs analysis can be used to determine the presence or absence of immunogenic cells. If <5% of viable cells are positive for the hematopoietic cell marker, CD45, and/or the endothelial cell marker, CD31, then the composition can be considered absent of immunogenic cells. An absence of immunogenic cells can be further confirmed if it does not produce >100 pg/ml of TNF upon stimulation with a bacterial immunogen, such as lipopolysaccharide (LPS), within about 24 hours of culture. In some instances, >5% of cells present in the composition can be immune cells however the composition would be considered absent of immunogenic cells if <5% of the viable cells are immune cells.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue comprises growth factors native to the meniscal tissue. The growth factors can be one or more of TGF-β1, TGF-b3, bFGF, PDGF-AB, PDGF-BB, IGF-1, HGF, BMP-7, EGF, CTGF, BMP-2, BMP-6, and VEGF.

Disclosed are compositions comprising a meniscal tissue, wherein the meniscal tissue comprises greater than 30% viable non-immunogenic cells native to the meniscal tissue and less than 5% viable immunogenic cells further comprising exogenous cells, growth factors, or proteins. Exogenous cells can be cultured cells or cells that originated from a different tissue.

Disclosed are compositions comprising a meniscal tissue, wherein the meniscal tissue comprises greater than 30% viable non-immunogenic cells native to the meniscal tissue and less than 5% viable immunogenic cells, wherein the composition does not comprise fatty, immunogenic connective tissue. In some instances, the fatty, immunogenic connective tissue can be from the joint capsule.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue does not comprise hematopoietic cells. In some instances, not comprising hematopoietic cells can mean that <5% of the total cells in the meniscal tissue are hematopoietic. Disclosed are compositions comprising a meniscal tissue, wherein the meniscal tissue comprises greater than 30% viable non-immunogenic cells native to the meniscal tissue and less than 5% viable immunogenic cells, wherein the meniscal tissue does not comprise hematopoietic cells but does comprise cells of mesenchymal origin, such as MSCs.

Disclosed are compositions comprising a meniscal tissue, wherein the meniscal tissue comprises greater than 30% viable non-immunogenic cells native to the meniscal tissue and less than 5% viable immunogenic cells, wherein the meniscal tissue comprises all collagen layers of human meniscus. Also disclosed are compositions comprising a meniscal tissue comprising greater than 30% viable non-immunogenic cells native to the meniscal tissue and less than 5% viable immunogenic cells, wherein the meniscal tissue comprises at least one of the collagen layers of human meniscus. In some instances, multiple collagen layers are present in the meniscal tissue of the composition but still less than all of the collagen layers normally found in human meniscus. Human meniscus comprises a superficial layer, a lamellar layer, and deep layers. Therefore, disclosed are compositions comprising a meniscal tissue, wherein the meniscal tissue comprises greater than 30% viable non-immunogenic cells native to the meniscal tissue and less than 5% viable immunogenic cells, wherein the meniscal tissue comprises all collagen layers of human meniscus, wherein the collagen layers comprise a superficial layer, a lamellar layer, and deep layers. In some instances, the collagen layers comprise random collagen fibers, radial tie fibers, and circumferential collagen fibers.

In some instances, the meniscal tissue of the composition does not comprise exogenous cells or cells that are not native to that tissue. In other words, in some instances any cells present in the meniscal tissue of the composition are native cells.

4. Cryopreservation

Disclosed are compositions comprising a meniscal tissue, wherein the meniscal tissue comprises viable cells native to the meniscal tissue and devitalized blood vessels, wherein the meniscal tissue is cryopreserved. In some instances, the viability of the cells is substantially maintained for at least about 24 months when stored frozen Disclosed are compositions comprising a meniscal tissue, wherein the meniscal tissue comprises viable cells native to the meniscal tissue and devitalized blood vessels further comprising a cryopreservation solution.

Also disclosed are previously cryopreserved compositions comprising a meniscal tissue, wherein the meniscal tissue comprises viable cells native to the meniscal tissue and devitalized blood vessels as described herein. Previously cryopreserved means that the composition has been thawed from its cryopreserved state.

Also disclosed are compositions comprising a meniscal tissue, wherein the meniscal tissue comprises greater than 30% viable non-immunogenic cells native to the meniscal tissue and less than 5% viable immunogenic cells, wherein the meniscal tissue is cryopreserved. In some instances, the viability of the cells is substantially maintained for at least about 24 months when stored frozen Disclosed are compositions comprising a meniscal tissue, wherein the meniscal tissue comprises greater than 30% viable non-immunogenic cells native to the meniscal tissue and less than 5% viable immunogenic cells further comprising a cryopreservation solution.

Also disclosed are previously cryopreserved compositions comprising a meniscal tissue, wherein the meniscal tissue comprises greater than 30% viable non-immunogenic cells native to the meniscal tissue and less than 5% viable immunogenic cells as described herein. Previously cryopreserved means that the composition has been thawed from its cryopreserved state.

D. Compositions Comprising Previously Cryopreserved Meniscal Tissue

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises an altered red zone. The meniscal tissue can also comprise an altered red-white zone. The altered red zone and the altered red-white zone can comprise blood vessel structures native to the red zone and red-white zone, respectively.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises an altered red zone, wherein the meniscal tissue has an inner edge and an opposed outer edge, and wherein the altered red zone has an outer surface that defines the outer edge of the meniscal tissue.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises an altered red zone, an altered red-white zone, and a white zone, wherein the altered red zone, altered red-white zone, and white zone are in an orientation as present in native meniscal tissue. In the case of the altered red zone and altered red-white zone, these altered zones are present in the orientation that a red zone and red-white zone are found in native meniscal tissue.

1. Engineered Channels

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, wherein the engineered channels are only present in the altered red zone. In some instances, the meniscal tissue further comprises and altered red-white zone, wherein the engineered channels are only present in the altered red zone and altered red-white zone.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, an altered red-white zone, and a white zone wherein the meniscal tissue has an inner edge and an opposed outer edge, and wherein at least one engineered channel does not extend from the outer edge of the meniscal tissue to the inner edge of the meniscal tissue. Optionally, in exemplary aspects, the red zone or altered red zone of the meniscal tissue can define the outer edge of the meniscal tissue, and the white zone of the meniscal tissue can define the inner edge of the meniscal tissue Thus, in these aspects, it is contemplated that at least one engineered channel does not extend completely through the altered red zone, the altered red-white zone, and the white zone.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, altered red-white zone, and white zone, wherein at least one engineered channel does not extend completely through the altered red zone. In other words, at least one engineered channel is contained solely within the altered red zone and does not extend into the altered red-white zone.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, wherein the meniscal tissue has an inner edge and an opposed outer edge, and wherein at least one engineered channel extends from the outer edge through only a portion of the altered red zone such that the at least one engineered channel does not reach the red-white zone or the white zone of the composition.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue has an inner edge and an opposed outer edge, wherein the inner edge is spaced from the outer edge in an inward direction, and wherein the engineered channels extend substantially in the inward direction. As used herein, the term "inward direction" generally refers to the direction of a line that extends substantially perpendicularly from a selected point on the outer edge of the meniscal tissue toward the inner edge of the meniscal tissue when the meniscal tissue is positioned in a relaxed position (i.e., no external force applied). As used herein, it is contemplated that engineered channels can extend substantially in the inward direction when they are positioned at an oblique angle (i.e., an acute or obtuse angle) relative to the outer edge of the meniscal tissue, provided the engineered channels generally extend toward a portion of the inner edge of the meniscal tissue. Alternatively, in exemplary non-limiting aspects, at least one engineered channel does not extend substantially in the inward direction. In these aspects, it is contemplated that the engineered channel can be positioned at an oblique angle that does not intersect with any portion of the inner edge when the meniscal tissue is positioned in the relaxed position.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein the meniscal tissue further comprises an altered red zone, wherein the meniscal tissue has an inner edge and an opposed outer edge, the outer edge having an exterior surface, wherein each engineered channel has a first end defined in the exterior surface of the outer edge of the meniscal tissue and an opposed second end defined within the altered red zone of the meniscal tissue, and wherein the first ends of the engineered channels are substantially evenly spaced about the exterior surface of the outer edge of the meniscal tissue. As used herein, the term "substantially evenly spaced" refers to a configuration of channels in which the first end of each channel is generally equally spaced from the first ends of its neighboring channels. In exemplary aspects, the engineered channels can be substantially evenly spaced when the first ends of the neighboring channels of the meniscal tissue are spaced apart by an average separation distance (measured center-to-center) and the separation distance between the first ends of each respective pair of neighboring channels falls within about 20% of the average separation distance. Alternatively, in exemplary non-limiting aspects, it is contemplated that the first ends of the engineered channels can be randomly spaced about the exterior surface of the outer edge of the meniscal tissue. Optionally, in still further exemplary aspects, the first ends of the engineered channels can be spaced apart in a configuration in which the separation distance between the first ends of neighboring channels is selectively varied to thereby produce a desired channel pattern. Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a diameter ranging from about 0.05 mm to about 2 mm. In some instances, each engineered channel has a diameter ranging from about 0.008 mm to about 2 mm. In some instances, the high end of the range can be about 1 mm. In some instances, each engineered channel has a diameter ranging from about 0.008 mm to about 1 mm or from about 0.2 mm to about 1 mm. The diameter of the engineered channels is large enough for at least one cell to fit inside the engineered channel. The average size of most mammalian cells is 10-30 μm, therefore, the diameter of the engineered channels can be larger than 10-30 μm. In some instances, the diameter of the engineered channel can be 8 μm, which can be smaller than the size of a cell but still larger enough for a cell to squeeze into the engineered channel. In some instances, the diameter of the engineered channels is large enough for multiple cells to fit inside the engineered channel. When determining diameter size, the height of the meniscal tissue should be considered. Engineered channels having diameters too much larger than 2 mm can lead to excessive tissue loss which can lead to weakening of the mechanical structure of the tissue and loss of tissue function.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a longitudinal axis, and wherein each engineered channel has a consistent diameter throughout the entire longitudinal length of the engineered channel. As used herein, the term "diameter" refers to the largest cross-sectional distance defined by the channel, and it is contemplated that the engineered can have any desired cross-sectional shape, including, for example and without limitation, a polygonal shape, such as a circle, an ellipse, a square, a rectangle, a rhombus, a trapezoid, and the like. The disclosed compositions can be attached to healthy meniscus in a subject to replace damaged tissue. The engineered channels within the meniscal tissue of the composition provide a greater surface area for the meniscal tissue. The greater surface area can allow for growth factors and cells from the subject's healthy meniscal tissue to contact the meniscal tissue of the composition in more places and allow for better integration of the meniscal tissue into the subject. The engineered channels also allow growth factors and cells present in the meniscal tissue to release from the meniscal tissue and contact the subject. In some instances, the diameter of a engineered channel can vary along the longitudinal length of the engineered channel. For example, the diameter of the engineered channel can get narrower or larger (e.g. cone shaped). In some instances, each engineered channel has a longitudinal axis, wherein at least one engineered channel has a diameter that varies moving along the longitudinal length of the engineered channel. In one exemplary aspect, at least a portion of at least one engineered channel can be inwardly tapered moving from the first end of the channel toward the second end of the channel such that the diameter of the channel decreases moving from the first end of the channel toward the second end of the channel. Alternatively, in another optional aspect, at least a portion of at least one engineered channel can be outwardly tapered moving from the first end of the channel toward the second end of the channel such that the diameter of the channel increases moving from the first end of the channel toward the second end of the channel. Optionally, in further exemplary aspects, the longitudinal axis of at least one engineered channel can be positioned at a selected angle (i.e., acute, perpendicular, or obtuse) relative to the longitudinal axis of at least one other engineered channel. In still further optional aspects, it is contemplated that the longitudinal axis of at least one engineered channel can be substantially parallel to the longitudinal axis of at least one other engineered channel.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a diameter, and wherein the diameter of at least one engineered channel is equal to the diameter of at least one other engineered channel. In some instances, the engineered channels can all have substantially the same diameter. In some instances, a portion of the engineered channels (i.e., a first group of channels) can all have substantially the same diameter and another portion of the engineered channels (i.e., a second group of channels) can all have substantially the same diameter wherein the at least two portions of engineered channels do not have the same diameter.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a longitudinal axis, and wherein each engineered channel has a longitudinal length ranging from about 0.2 mm to about 5 mm. In some instances, each engineered channel can have a longitudinal length ranging from about 0.1 mm to about 10 mm. Longitudinal lengths can vary. Longitudinal lengths can be based on the location of the engineered channel within the meniscal tissue. The engineered channels can be present in a vascular zone or altered vascular zone of the meniscal tissue. The vascular zone of the average human meniscus can be about 3-5 mm in length. In some aspects, the uppermost surface of the vascular zone is not as wide due to the triangular shape of the meniscus. Thus, engineered channels in the uppermost region of the vascular zone can have a shorter longitudinal length than engineered channels toward the middle region or lower region of the vascular zone. The longitudinal length can be based on the location of the engineered channel within the meniscal tissue. In some instances, the longitudinal length of a engineered channel can be as small as 0.1 mm.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue further comprises engineered channels, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length. In some instances, a portion of the engineered channels (i.e., a first group of channels) can all have substantially the same longitudinal length and another portion of the engineered channels (i.e., a second group of channels) can all have substantially the same longitudinal length, wherein the at least two portions of engineered channels do not have the same longitudinal length.

2. Size of Meniscal Tissue

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue has an inner edge and an opposed outer edge, wherein the outer edge has a first end and an opposed second end, and wherein a first line extending from the first end of the outer edge to the second end of the outer edge has a length (i.e., chord length) ranging from about 5 mm to about 60 mm.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue has an inner edge and an opposed outer edge, wherein the outer edge has a first end and an opposed second end, and wherein a first line extending from the first end of the outer edge to the second end of the outer edge has a length (i.e., chord length) ranging from about 5 mm to about 60 mm, wherein the outer edge of the meniscal tissue has an exterior surface and a center point positioned midway between the first and second ends of the outer edge relative to the exterior surface, and wherein a second line extending perpendicularly from the center point to the first line has a length ranging from about 5 mm to about 20 mm The length (i.e., chord length) of a first line extending from the first end of the outer edge to the second end of the outer edge can vary based on the desired size of the meniscal tissue. For example, a meniscal tissue that can cover about 50% defects in most people can have a first line extending from the first end of the outer edge to the second end of the outer edge having a length (i.e., chord length) ranging from about 25 mm to about 27 mm. Meniscal tissue around this size can allow for versatility because they can be used for treating both medial and lateral defects. However, smaller meniscal tissue pieces can have a first line extending from the first end of the outer edge to the second end of the outer edge having a length (i.e., chord length) of 5 mm.

The length of a second line extending perpendicularly from the center point to the first line can vary based on the desired size of the meniscal tissue. For example, a meniscal tissue that can cover about 50% defects in most people can have a second line extending perpendicularly from the center point to the first line that has a length ranging from about 9 mm to about 13 mm. Meniscal tissue around this size are designed for versatility because they can be used for treating both medial and lateral defects.

In some instances, the size of the meniscal tissue of the composition is 10, 20, 30, 40, 50, 60, 70, 80, 90, or 100% of a full size, naturally-occurring meniscus. In other words, the meniscal tissue of the composition can be an entire, full length meniscus or can be a portion of full length meniscus. FIG. 24 shows a schematic of a full length meniscus. As described herein, the meniscal tissue of the composition can comprise the entire width of the red zone (R), red-white zone (R-W), and white zone (W) or a portion of one or more of red zone, red-white zone, and white zone. The red zone can also be referred to as the outer third. The red-white zone can also be referred to as the middle zone. The white zone can also be referred to as the inner zone.

The meniscal tissue of the composition can comprise the full length of a meniscus meaning it can comprise the anterior (A), central/middle (C), and posterior (P) regions of the meniscus or it can comprise a portion of one more of these regions (see FIG. 24). For example, meniscal tissue of the composition can comprise 1) all or a portion of the central region, 2) all or a portion of the central region and all or a portion of the posterior region, 3) all or a portion of the central region and all or a portion of the anterior region, 4) all or a portion of the central region and all or a portion of the posterior region and all or a portion of the anterior region, or 5) all or a portion of the anterior or posterior region.

FIG. 24 also shows the different depths of meniscal tissue. The meniscal tissue of the composition can comprise all the layers or a portion of the layers found in native meniscus. In some instances, the meniscal tissue of the composition can comprise the top surface layer, the top lamellar layer and all or a portion of the deep zone. In some instances, the meniscal tissue of the composition can comprise the bottom surface layer, the bottom lamellar layer and all or a portion of the deep zone.

3. Native Factors in Meniscal Tissue

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells. In some instances, the meniscal tissue comprises at least 70% viable cells native to the meniscal tissue. In some instances, the meniscal tissue comprises at least 20, 30, 40, 50, 60, 70, 80, or 90% viable cells native to the meniscal tissue. In some instances, at least a portion of the viable cells native to the meniscal tissue are of mesenchymal origin. For example, in some instances at least a portion of the viable cells native to the meniscal tissue of mesenchymal origin are MSCs.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the composition is not immunogenic. A composition is immunogenic if it produces >100 pg/mL of TNF upon stimulation with a bacterial immunogen, such as LPS, within about 24 hours of culture. FACs analysis can be used to determine the presence or absence of immunogenic cells. If <5% of viable cells are positive for the hematopoietic cell marker, CD45, and/or the endothelial cell marker, CD31, then the composition can be considered absent of immunogenic cells. An absence of immunogenic cells can be further confirmed if it does not produce >100 pg/ml of TNF upon stimulation with a bacterial immunogen, such as LPS, within about 24 hours of culture. In some instances, >5% of cells present in the composition can be immune cells however the composition would be considered absent of immunogenic cells if <5% of the viable cells are immune cells.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue comprises growth factors native to the meniscal tissue. The growth factors can be one or more of TGF-β1, TGF-b3, bFGF, PDGF-AB, PDGF-BB, IGF-1, HGF, BMP-7, EGF, CTGF, BMP-2, BMP-6, and VEGF.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells further comprising exogenous cells, growth factors, or proteins. Exogenous cells can be cultured cells or cells that originated from a different tissue.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the composition does not comprise fatty, immunogenic connective tissue. In some instances, the fatty, immunogenic connective tissue can be from the joint capsule.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue does not comprise hematopoietic cells. In some instances, not comprising hematopoietic cells can mean that <5% of the total cells in the meniscal tissue are hematopoietic. Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue does not comprise hematopoietic cells but does comprise cells of mesenchymal origin, such as MSCs.

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue comprises all collagen layers of human meniscus. Also disclosed are compositions comprising a meniscal tissue comprising viable cells native to the meniscal tissue and devitalized blood vessels, wherein the meniscal tissue comprises at least one of the collagen layers of human meniscus. In some instances, multiple collagen layers are present in the meniscal tissue of the composition but still less than all of the collagen layers normally found in human meniscus. Human meniscus comprises a superficial layer, a lamellar layer, and deep layers. Therefore, disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the meniscal tissue comprises all collagen layers of human meniscus, wherein the collagen layers comprise a superficial layer, a lamellar layer, and deep layers. In some instances, the collagen layers comprise random collagen fibers, radial tie fibers, and circumferential collagen fibers.

In some instances, the meniscal tissue of the composition does not comprise exogenous cells or cells that are not native to that tissue. In other words, in some instances any cells present in the meniscal tissue of the composition are native cells.

4. Cryopreservation

Disclosed are compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells, wherein the previously cryopreserved meniscal tissue is stored for an extended period of time prior to subsequent thawing. In some instances, the extended period of time is from about 1 day to at least 24 months.

E. Methods of Making

Disclosed are methods of producing the disclosed compositions comprising forming engineered channels in a meniscal tissue isolated from a subject. For example, disclosed are methods of producing compositions comprising a meniscal tissue, comprising forming engineered channels in a meniscal tissue isolated from a subject. Also disclosed are methods of producing compositions comprising a meniscal tissue comprising viable cells native to the meniscal tissue and devitalized blood vessels, comprising forming engineered channels in a meniscal tissue isolated from a subject. Also disclosed are methods of producing compositions comprising a meniscal tissue comprising greater than 30% viable non-immunogenic cells native to the meniscal tissue and less than 5% viable immunogenic cells, wherein the meniscal tissue further comprises engineered channels, comprising forming engineered channels in a meniscal tissue isolated from a subject.

In some instances, a meniscal tissue isolated from a subject can be cryopreserved, wherein the engineered channels can be formed in the meniscal tissue prior to cryopreservation. In some instances, a meniscal tissue isolated from a subject can be cryopreserved, wherein the engineered channels can be formed in the meniscal tissue after thawing the cryopreserved meniscal tissue.

Disclosed are methods of producing the disclosed compositions comprising forming engineered channels in a meniscal tissue isolated from a subject, wherein the engineered channels can be formed using the disclosed tools. For example, the engineered channels can be formed using a tool for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position.

Disclosed are methods of producing the disclosed compositions comprising forming engineered channels in a meniscal tissue isolated from a subject, wherein the meniscal tissue further comprises a red zone or an altered red zone, wherein the engineered channels are only present in the red zone or altered red zone. In some instances, the meniscal tissue further comprises a red-white zone or an altered red-white zone, wherein the engineered channels are only present in the red zone and red-white zone or altered red zone and altered red-white zone, respectively.

Disclosed are methods of producing the disclosed compositions comprising forming engineered channels in a meniscal tissue isolated from a subject, wherein the meniscal tissue further comprises a red zone, a red-white zone, and a white zone or an altered red zone, an altered red-white zone, and a white zone wherein the meniscal tissue has an inner edge and an opposed outer edge, and wherein at least one engineered channel does not extend from the outer edge of the meniscal tissue to the inner edge of the meniscal tissue. For example, the outer edge of the meniscal tissue can be the edge containing the red zone or altered red zone while the inner edge can be the edge containing the white zone.

Disclosed are methods of producing the disclosed compositions comprising forming engineered channels in a meniscal tissue isolated from a subject, wherein the meniscal tissue further comprises a red zone, a red-white zone and a white zone, or an altered red zone, altered red-white zone, and white zone, wherein at least one engineered channel does not extend completely through the red zone or altered red zone. In other words, at least one engineered channel is contained solely within the red zone or altered red zone and does not extend into the red-white zone or altered red-white zone. Disclosed are methods of producing the disclosed compositions comprising forming engineered channels in a meniscal tissue isolated from a subject, wherein the meniscal tissue further comprises a red zone or an altered red zone, wherein the meniscal tissue has an inner edge and an opposed outer edge, and wherein at least one engineered channel extends from the outer edge through only a portion of the red zone or altered red zone.

Disclosed are methods of producing the disclosed compositions comprising forming engineered channels in a meniscal tissue isolated from a subject, wherein the meniscal tissue has an inner edge and an opposed outer edge, wherein the inner edge is spaced from the outer edge in an inward direction, and wherein the engineered channels extend substantially in the inward direction.

Disclosed are methods of producing the disclosed compositions comprising forming engineered channels in a meniscal tissue isolated from a subject, wherein the meniscal tissue further comprises a red zone or an altered red zone, wherein the meniscal tissue has an inner edge and an opposed outer edge, the outer edge having an exterior surface, wherein each engineered channel has a first end defined in the exterior surface of the outer edge of the meniscal tissue and an opposed second end defined within the red zone or altered red zone of the meniscal tissue, and wherein the first ends of the engineered channels are substantially evenly spaced about the exterior surface of the outer edge of the meniscal tissue. As used herein, the term "substantially evenly spaced" refers to a configuration of channels in which the first end of each channel is generally equally spaced from the first ends of its neighboring channels. In exemplary aspects, the engineered channels can be substantially evenly spaced when the first ends of the neighboring channels of the meniscal tissue are spaced apart by an average separation distance (measured center-to-center) and the separation distance between the first ends of each respective pair of neighboring channels falls within about 20% of the average separation distance. Alternatively, in exemplary non-limiting aspects, it is contemplated that the first ends of the engineered channels can be randomly spaced about the exterior surface of the outer edge of the meniscal tissue. Optionally, in still further exemplary aspects, the first ends of the engineered channels can be spaced apart in a configuration in which the separation distance between the first ends of neighboring channels is selectively varied to thereby produce a desired channel pattern. Disclosed are methods of producing the disclosed compositions comprising forming engineered channels in a meniscal tissue isolated from a subject, wherein each engineered channel has a diameter ranging from about 0.05 mm to about 2 mm. In some instances, the high end of the range can be about 1 mm. In some instances, each engineered channel has a diameter ranging from about 0.2 mm to about 1 mm. The diameter of the engineered channels is large enough for at least one cell to fit inside the engineered channel. The average size of most mammalian cells is 10-30 µm, therefore, the diameter of the engineered channels can be larger than 10-30 µm. In some instances, the diameter of the engineered channel can be 8 µm, which can be smaller than the size of a cell but still larger enough for a cell to squeeze into the engineered channel. In some instances, the diameter of the engineered channels is large enough for multiple cells to fit inside the engineered channel. When determining diameter size, the height of the meniscal tissue should be considered. Engineered channels having diameters too much bigger than 2 mm can lead to excessive tissue loss which can lead to weakening of the mechanical structure of the tissue and loss of tissue function.

Disclosed are methods of producing the disclosed compositions comprising forming engineered channels in a meniscal tissue isolated from a subject, wherein each engineered channel has a longitudinal axis, and wherein each engineered channel has a consistent diameter throughout the entire longitudinal length of the engineered channel. The disclosed compositions can be attached to healthy meniscus in a subject to replace damaged tissue. The engineered channels within the meniscal tissue of the composition provide a greater surface area for the meniscal tissue. The greater surface area can allow for growth factors and cells from the subject's healthy meniscal tissue to contact the meniscal tissue of the composition in more places and allow for better integration of the meniscal tissue into the subject. The engineered channels also allow growth factors and cells present in the meniscal tissue to release from the meniscal tissue and contact the subject. In some instances, the diameter of a engineered channel can vary along the longitudinal length of the engineered channel. For example, the diameter of the engineered channel can get narrower or larger (e.g. cone shaped). In some instances, each engineered channel has a longitudinal axis, wherein at least one engineered channel has a diameter that varies moving along the longitudinal length of the engineered channel.

Disclosed are methods of producing the disclosed compositions comprising forming engineered channels in a meniscal tissue isolated from a subject, wherein each engineered channel has a diameter, and wherein the diameter of at least one engineered channel is equal to the diameter of at least one other engineered channel. In some instances, the engineered channels can all have substantially the same diameter. In some instances, a portion of the engineered channels can all have substantially the same diameter and another portion of the engineered channels can all have substantially the same diameter wherein the at least two portions of engineered channels do not have the same diameter.

Disclosed are methods of producing the disclosed compositions comprising forming engineered channels in a meniscal tissue isolated from a subject, wherein each engineered channel has a longitudinal axis, and wherein each engineered channel has a longitudinal length ranging from about 0.2 mm to about 5 mm. Longitudinal lengths can vary. Longitudinal lengths can be based on the location of the engineered channel within the meniscal tissue. The engineered channels can be present in a vascular zone of the meniscal tissue. The vascular zone of the average human meniscus can be about 3-5 mm in length. In some aspects, the uppermost surface of the vascular zone is not as wide due to the triangular shape of the meniscus. Thus, engineered channels in the uppermost region of the vascular zone can have a shorter longitudinal length than engineered channels toward the middle region or lower region of the vascular zone. The longitudinal length can be based on the location of the engineered channel within the meniscal tissue. In some instances, the longitudinal length of an engineered channel can be as small as 0.1 mm.

Disclosed are methods of producing the disclosed compositions comprising forming engineered channels in a meniscal tissue isolated from a subject, wherein each engineered channel has a longitudinal axis and a longitudinal length, and wherein the longitudinal length of at least one engineered channel is substantially equal to the longitudinal length of at least one other engineered channel. In some instances, the engineered channels can all have substantially the same longitudinal length. In some instances, a portion of the engineered channels can all have substantially the same longitudinal length and another portion of the engineered channels can all have substantially the same longitudinal length, wherein the at least two portions of engineered channels do not have the same longitudinal length.

Although generally disclosed herein as extending from the exterior surface of the outer edge of the meniscal tissue, it is contemplated that engineered channels as disclosed herein can extend from any desired exterior surface of the meniscal tissue, such as, for example and without limitation, an upper surface or a lower surface of the meniscal tissue that adjoins the exterior surface of the outer edge of the meniscal tissue.

F. Methods of Treating

Disclosed are methods of repairing at least one meniscal defect in a meniscus of a subject comprising using one or more of the compositions described herein. For example, disclosed herein are methods of repairing at least one meniscal defect in a meniscus of a subject comprising replacing the meniscal defect with any one of the disclosed compositions. For example, disclosed are methods of repairing at least one meniscal defect in a meniscus of a subject comprising replacing the meniscal defect with compositions comprising a meniscal tissue, wherein the meniscal tissue comprises one or more engineered channels. Disclosed are methods of repairing at least one meniscal defect in a meniscus of a subject comprising replacing the meniscal defect with compositions comprising a meniscal tissue comprising viable cells native to the meniscal tissue and devitalized blood vessels. Disclosed are methods of repairing at least one meniscal defect in a meniscus of a subject comprising replacing the meniscal defect with compositions comprising a meniscal tissue comprising greater than 30% viable non-immunogenic cells native to the meniscal tissue and less than 5% viable immunogenic cells. Disclosed are methods of repairing at least one meniscal defect in a meniscus of a subject comprising replacing the meniscal defect with compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells.

Replacing the at least one meniscal defect can comprise removing the at least one meniscal defect by cutting or shaving the meniscus around the at least one meniscal defect to define a receiving space, and inserting the composition into the receiving space. A receiving space is a space that is formed by cutting or shaving around the meniscal defect(s). All meniscal defects may not be eliminated by the receiving space. However, the receiving space is formed by cutting or shaving around the meniscal defect(s) of interest.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space, wherein the meniscus has an inner edge and an opposed outer edge, the inner edge and the outer edge having respective exterior surfaces, wherein the step of removing the at least one meniscal defect comprises making a first incision on a first side of the at least one meniscal defect, wherein the first incision extends from the exterior surface of the inner edge to a first selected position spaced from the outer edge of the meniscus; and making a second incision on a second side of the at least one meniscal defect that is opposed from the first side of the at least one meniscal defect, wherein the second incision extends from the exterior surface of the inner edge to a second selected position spaced from the outer edge of the meniscus. Optionally, in exemplary aspects, at least one of the first and second incisions can be substantially perpendicular to the outer edge of the meniscus. In these aspects, it is contemplated that both the first and the second incisions can optionally be substantially perpendicular to the outer edge of the meniscus. Alternatively, in other exemplary aspects, at least one of the first and second incisions can have an arcuate or curved profile that circumferentially surrounds a portion of the meniscal defect. However, it is understood that any desired incision orientation can be used. Optionally, in still further exemplary aspects, rather than using two distinct incisions, it is contemplated that the entire meniscal defect can be removed by forming a single incision that circumferentially surrounds the meniscal defect.

The step of removing the at least one meniscal defect can further comprise removing portions of the meniscus positioned between the first and second incisions to define the receiving space. The steps of making first and second incisions can define first and second side walls of the receiving space, and the step of removing portions of the meniscus positioned between the first and second incisions can comprise defining a peripheral wall of the receiving space, wherein the peripheral wall can be consistently radially spaced from the exterior surface of the outer edge of the meniscus.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space, wherein the meniscus has an inner edge and an opposed outer edge, the inner edge and the outer edge having respective exterior surfaces, wherein the step of removing the at least one meniscal defect comprises making a first incision on a first side of the at least one meniscal defect, wherein the first incision extends from the exterior surface of the inner edge to a first selected position spaced from the outer edge of the meniscus; and making a second incision on a second side of the at least one meniscal defect that is opposed from the first side of the at least one meniscal defect, wherein the second incision extends from the exterior surface of the inner edge to a second selected position spaced from the outer edge of the meniscus, further comprising forming at least one vascular access channel that extends from the peripheral wall of the receiving space of the subject's meniscus through the meniscus and toward the exterior surface of the outer edge of the subject's meniscus. Optionally, the at least one vascular access channel can comprise a plurality of vascular access channels (e.g., engineered channels) that extend from the peripheral wall of the receiving space of the subject's meniscus toward the exterior surface of the outer edge of the subject's meniscus.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, further comprising selectively removing portions of the composition until the composition has a desired shape that substantially corresponds to a shape of the receiving space. In some instances, selectively removing portions of the composition until the composition has a desired shape that substantially corresponds to a shape of the receiving space can be performed by measuring the receiving space and cutting or shaving the composition to the measured size of the receiving space.

Disclosed are methods of repairing at least one meniscal defect in a meniscus of a subject comprising replacing the meniscal defect with the disclosed compositions, wherein replacing the at least one meniscal defect comprises removing the at least one meniscal defect by cutting or shaving the meniscus around the at least one meniscal defect to define a receiving space, and inserting the composition into the receiving space, wherein inserting the composition into the receiving space comprises attaching the composition to selected portions of the subjects meniscus surrounding the receiving space, wherein the meniscus has an inner edge and an opposed outer edge, the inner edge and the outer edge having respective exterior surfaces, wherein the step of removing the at least one meniscal defect comprises making a first incision on a first side of the at least one meniscal defect, wherein the first incision extends from the exterior surface of the inner edge to a first selected position spaced from the outer edge of the meniscus; and making a second incision on a second side of the at least one meniscal defect that is opposed from the first side of the at least one meniscal defect, wherein the second incision extends from the exterior surface of the inner edge to a second selected position spaced from the outer edge of the meniscus, wherein the step of removing the at least one meniscal defect further comprises removing portions of the meniscus positioned between the first and second incisions to define the receiving space, wherein the steps of making first and second incisions defines first and second side walls of the receiving space, and wherein the step of removing portions of the meniscus positioned between the first and second incisions comprises defining a peripheral wall of the receiving space, wherein the peripheral wall is consistently radially spaced from the exterior surface of the outer edge of the meniscus, wherein the step of attaching the composition to selected portions of the meniscus comprises inserting a fixation device into the composition. A fixation device can be any device capable of being used to attach the composition to the meniscus of the subject. A fixation device can be a device that inserts or otherwise effects operative positioning of a separate fixation element, which in turn affixes the composition to the meniscus of the subject or a fixation device can directly affix the composition to the meniscus. For example, a fixation device can be a device that inserts sutures or in some instances can be the sutures. A fixation device can also be an anchor, a needle, staples, staple gun, fixation darts, lasso, sharp cannula loaded with suture, or natural or synthetic material that forms a net around the regions requiring fixation. The needle can be a double-armed, open-ended spinal, or other thin, flexible, open-ended needle.

In some instances, the step of attaching the composition to selected portions of the meniscus comprises securing at least a portion of the exterior surface of the outer edge of the composition to the peripheral wall of the receiving space of the meniscus. Optionally, the step of securing at least a portion of the exterior surface of the outer edge of the composition to the peripheral wall of the receiving space can comprises inserting the fixation device through the peripheral wall of the receiving space of the meniscus and passing the fixation device through the exterior surface of the outer edge of the meniscus. Alternatively, it is contemplated that the composition can be attached to selected portions of the meniscus without passing a fixation device through the meniscus. For example, in one optional aspect, the exterior surface of the outer edge of the composition can be secured to the peripheral wall of the receiving space of the meniscus using a stitch that extends circumferentially around a portion of the meniscus and composition without piercing any portion of the meniscus. Examples of such circumferential stitches are produced by Ceterix Therapeuitcs (e.g. NovoStitch).

In some instances, the step of attaching the composition to selected portions of the meniscus further comprises inserting at least one fixation device between the composition and the meniscus and across the first side wall of the receiving space of the meniscus; and inserting at least one fixation device between the composition and the meniscus and across the second side wall of the receiving space of the meniscus.

In the disclosed methods, cells from the meniscus or surrounding tissues or fluids of the subject can migrate to the meniscal tissue of the composition. The cells from the meniscus or surrounding tissue or fluids of the subject can come from blood, bone marrow, synovial fluid, synovial membrane, or lymphatics. The cells from the meniscus or surrounding tissues or fluids of the subject can comprise one or more of mesenchymal stem cells, chondrocytes, fibrochondrocytes, fibroblasts, chondroprogenitor cells, synoviocytes, and endothelial cells.

Disclosed are methods of repairing at least one meniscal defect in a meniscus of a subject comprising replacing the meniscal defect with any one of the disclosed compositions, wherein cells from the meniscus or surrounding tissues or fluids of the subject can migrate to and adhere to the engineered channels of the meniscal tissue of the composition.

Disclosed are methods of repairing at least one meniscal defect in a meniscus of a subject comprising replacing the meniscal defect with any one of the disclosed compositions, wherein the meniscal tissue of the composition comprises viable cells native to the meniscal tissue of the composition. In some instances, the meniscal tissue of the composition comprises 70% viable cells native to the meniscal tissue of the composition. In some instances, the meniscal tissue of the composition comprises 20, 30, 40, 50, 60, 70, 80, or 90% viable cells native to the meniscal tissue of the composition. In some instances, the viable cells native to the meniscal tissue of the composition are non-immunogenic cells. In some instances, the cells native to the meniscal tissue of the composition can proliferate. In some instances, the cells native to the meniscal tissue of the composition can secrete functional growth factors. For example, the growth factors can be one or more of TGF-β1, TGF-b3, bFGF, PDGF-AB, PDGF-BB, IGF-1, HGF, BMP-7, EGF, CTGF, BMP-2, BMP-6, and VEGF.

Disclosed are methods of repairing at least one meniscal defect in a meniscus of a subject comprising replacing the meniscal defect with any one of the disclosed compositions, wherein the subject is a mammal. In some instances, the subject can be a human. In some instances, the subject can be, but is not limited to, a horse, sheep, dog, or cow.

G. Engineered Channel-Forming Tool

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position. Although disclosed herein as extending outwardly from the base portion relative to the vertical axis, it is contemplated that one or more of the engineered channels can be angularly oriented relative to the vertical axis (e.g., at a selected acute angle). In exemplary aspects, the projections can be substantially cylindrical. However, it is contemplated that the projections can have any desired shape that is capable of forming an engineered channel as disclosed herein. Optionally, in exemplary aspects, the projections can have a tapered profile with a variable diameter that is capable of forming tapered channels as disclosed herein. For example, in some aspects, it is contemplated that the projections can have a substantially conical profile.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the tool further comprises a securing mechanism configured to selectively secure the insert within the receptacle. As described herein, the "operative position" of the insert refers to a position of the insert in which the projections of the insert are configured to form engineered channels within a meniscal tissue as disclosed herein.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the tool further comprises a securing mechanism configured to selectively secure the insert within the receptacle, wherein the receptacle defines a bore, wherein the base portion of the insert has a first side wall that defines a recess, wherein, when the insert is received within the receptacle in the operative position, the bore of the receptacle is positioned in substantial alignment with the recess of the first side wall of the base portion relative to the longitudinal axis, wherein the securing mechanism comprises a screw that is positioned within the bore of the receptacle, and wherein, when the insert is received within the receptacle in the operative position, the screw is configured for axial advancement relative to the longitudinal axis until a distal portion of the screw is received within the recess of the first side wall of the base portion.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the receptacle has first and second guide walls that are spaced apart relative to the longitudinal axis.

Disclosed are tools for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position, wherein the receptacle has first and second guide walls that are spaced apart relative to the longitudinal axis, further comprising an elongate body that extends outwardly from the second guide wall of the receptacle relative to the longitudinal axis. In some instances, the elongate body can comprise a ruler.

H. Kits

Disclosed are kits comprising any one or more of the disclosed compositions. For example, disclosed are kits comprising compositions comprising a meniscal tissue, wherein the meniscal tissue comprises one or more engineered channels. Disclosed are kits comprising compositions comprising a meniscal tissue, wherein the meniscal tissue comprises viable cells native to the meniscal tissue and devitalized blood vessels. Disclosed are kits comprising compositions comprising a meniscal tissue, wherein the meniscal tissue comprises greater than 30% viable non-immunogenic cells native to the meniscal tissue and less than 5% viable immunogenic cells. Disclosed are kits comprising compositions comprising a previously cryopreserved meniscal tissue, wherein after cryopreservation and subsequent thawing the meniscal tissue comprises a) cells native to the meniscal tissue and greater than 30% of the cells are viable, b) extracellular matrix that is native to the meniscal tissue, c) one or more growth factors that are native to the meniscal tissue, and d) depleted amounts of one or more types of functional immunogenic cells. The compositions comprising meniscal tissue in the kits can comprise cells of mesenchymal origin, such as MSCs, native to the meniscal tissue.

In some instances, the kit can further comprise at least one fixation device. For example, the kit can further comprise a suture needle, a suture, or both.

In some instances, the kit can further comprise at least one cannula, trocar, or obturator.

In some instances, the kit can further comprise a tool for cutting or shaving the meniscal tissue of the composition. Tools for cutting or shaving the meniscal tissue can be, but are not limited to, a scalpel, scissors, knives, blades, biters, punchers, or arthroscopic shavers. For example, the kit can comprise at least one of the disclosed compositions and scalpel.

In some instances, the kit can further comprise a tool for measuring the dimensions of a meniscus defect. A tool for measuring the dimensions of a meniscus defect can be, but is not limited to, a ruler.

In some instances, the kit can further comprise a tool for forming channels in the composition. The disclosed engineered channel-forming tools can be present in the kits. For example, a kit can comprise at least one of the disclosed compositions and a tool for forming a plurality of engineered channels within a product, the tool having a longitudinal axis and comprising a receptacle; and an insert having a base portion and a plurality of projections secured to and extending outwardly from the base portion relative to a vertical axis that is substantially perpendicular to the longitudinal axis, wherein the receptacle is configured to removably receive the insert in an operative position. In some instances, the tool for forming the plurality of engineered channels further comprises a tool for measuring.

Disclosed are kits comprising at least one of the disclosed compositions and further comprising a solution. In some instances, the solution is a thawing solution. In some instances, the solution is a wash solution. Thawing solutions and wash solutions can be, but are not limited to, saline, water, phosphate buffered saline, PlasmaLyte, physiologically balanced salt solutions, or platelet-rich plasma.

EXAMPLES

A. Development of a Previously Cryopreserved Meniscal Tissue: Viable Meniscal Allograft A previously cryopreserved meniscal tissue can be used as a viable meniscal allograft, which has an intact native meniscus architecture, chondrogenic and angiogenic growth factors, and endogenous meniscal fibrochondrocytes and chondrocytes identical to native human meniscus. A previously cryopreserved meniscal tissue can be used to repair meniscus defects following partial meniscectomy. A broad spectrum of immunochemical, cell-based, and biomechanical assays were used to assess the safety, function, and potency of a previously cryopreserved meniscal tissue including ELISA for presence of growth factors within lysates and conditioned medium, FACS, cell adhesion and migration, and biomechanical function. Data show that a previously cryopreserved meniscal tissue has high cell viability post-thaw, encourages adhesion and migration of human meniscus cells and hMSCs, and secretes greater levels of functional growth factors than acellular controls. No immunogenic components were detected in a previously cryopreserved meniscal tissue. Data indicate that engineered channel added along the surface of a previously cryopreserved meniscal tissue meant to interface with the host tissue after implantation promote deeper penetration of migrating cells and greater release of essential growth factors for meniscus repair compared to non-perforated controls. A previously cryopreserved meniscal tissue will thaw in less than 5 minutes once submerged in sterile saline, remains stable at room temperature for up to 3 hours after thawing, and can be cut to size to match any meniscal defect dimensions Unlike total meniscal allografts, a previously cryopreserved meniscal tissue requires no donor-recipient size matching and can be used to repair both medial and lateral defects. In summary, a previously cryopreserved meniscal tissue is a ready-to-use cryopreserved viable meniscal allograft that can be implanted in a single-step procedure to repair meniscus defects following partial meniscectomy.

1. Methods i. Tissue Collection and Processing

Meniscus tissue was isolated from human knee-en-blocs or leg-en-blocs received from tissue banks after authorization for donation. The tissues were collected according to recovery agency SOPs. The finalized procedure of processing the donor knee-en-blocs or leg-en-blocs is described below.

Surfaces of cadaveric knees-en-bloc or leg-en-blocs were thoroughly wiped down with povidone iodine solution using sterile wiper. The knee joint was dissected to separate the femur, tibia and fibula without damaging the cartilage surfaces, meniscus, or periosteum and preserving the bone-tendon-bone (BTB). Soft tissue (adipose, muscle, fascia, ligaments and tendons) was removed to expose the articular cartilage surfaces on tibial plateau and the overlaying meniscus.

Using dissecting scissors or a scalpel, the ligamentous attachments near the center of the tibia connecting each meniscus to bone were severed, and the fatty, connective tissue of the joint capsule and collateral ligament attachments to the center of each meniscus were cut away to isolate 1 medial and 1 lateral meniscus from each knee-en-bloc.

a. Trimming of Whole Meniscal Tissue

Isolated whole meniscus pieces were further trimmed to remove all fatty tissue from each meniscus, exposing the fibrillar collagen structure of the meniscus. Care was taken not to remove excess tissue from the periphery, for this is the vascularized, growth-factor rich region of the meniscus known to be capable of spontaneous repair in vivo.

b. Forming Engineered Channels in the Meniscal Tissue

For each whole meniscus piece, the tissue was perforated using a selection of engineered channel tools—a microdermal roller (0.2 mm spikes, 3 mm long), 1 mm biopsy punch, 0.2 mm biopsy punch, or a custom stainless steel channel tool (0.5 mm spikes, 3 mm long).

c. Shaping of Uniform Units

To generate uniform pieces, each meniscus can be measured with a ruler and cut to form uniform pieces of meniscal tissue with engineered channels. For example, a piece can have the dimensions of: a) the outer corner to corner length being 26 mm±1 mm and b) the midline length being 11 mm±2 mm.

d. Treating all Meniscal Tissue with Antibiotic to Sterilize

Prior to placement of units into antibiotic solution, all units can be pooled together, dabbed with tissue paper to remove excess water, and a total tissue weight can be measured with a balance and recorded.

Viable meniscal units were then added to an antibiotic cocktail of gentamycin, vancomycin, and amphotericin B t a maximum ratio of 1 g meniscal tissue for every 10 ml antibiotic solution (25 g or less in 250 ml antibiotic solution) for 18 to 84 hours at 37° C., 5% CO2.

Meniscal tissue was then rinsed twice in saline and the entire lot was submerged in cryopreservation solution containing DMSO (and incubated for a period of time at a pre-determined temperature.

At that time, individual units were packaged and transferred to a −80±5° C. freezer.

ii. Live/Dead Staining and Cell Counting

The presence of viable cells within a previously cryopreserved meniscal tissue was assessed with the LIVE/DEAD Viability/Cytotoxicity kit, a commercially available fluorescent cell staining kit. Staining was performed according to the manufacturer's instructions. The presence of live cells (green staining) and dead cells (red staining) was assessed fluorescently. Thin slices of previously cryopreserved meniscal tissue from the top layer, bottom layer, or both layers were placed into cell culture plates and incubated with 1 ml of staining solution for 20-30 min. at 37° C./5% $CO_2$. Staining solution was prepared by adding 1 µl of Calcein-AM solution and 1 µl of ethidium bromide solution to 1 ml of PBS. Following incubation, slices were placed onto a slide and photographed using a fluorescent microscope (Olympus IX70) with an attached camera. In some cases, live and dead cells were hand-counted for a quantitative comparison of test conditions. In such cases, at least 3 different fields of view were imaged and counted and an mean viability and standard deviation across fields was calculated.

iii. Growth Factor Analysis

Cryopreserved meniscal tissue was thawed for 5-10 minutes by directly adding room temperature saline. Units were cut into small pieces, minced using a scalpel into very small cubes (1×1×1 mm), and snap-frozen in a homogenization tube placed in a liquid nitrogen bath. Once pre-cooled (for at least 5 minutes on dry ice) 5 mm steel bead was added to each tube and tissue was homogenized in an appropriate buffer using a Qiagen Tissue Lyser). Homogenates were then gently rotated overnight at 4° C. Homogenates were then spun down at 18,000+1000 g for 10+1 minutes using a microcentrifuge. Supernatants were collected and analyzed for specific growth factors via ELISA using either R&D System Duoset or Quantikine kit. GuHCl treated samples were processed using a Zeba Spin Desalting Column (Thermo Scientific).

iv. Biomechanical Tibial Contact Pressure Testing

Contact pressures and contact areas on the tibial cartilage underneath the meniscus of human cadaveric knee specimens were measured using a static load mechanical test system. The goal of this experiment was to compare the contact pressure distributions for intact meniscus to an injured state after partial meniscectomy and repaired state after implantation of a previously cryopreserved meniscal tissue following partial meniscectomy. In all repair cases, medial defects were repaired with a previously cryopreserved meniscal tissue from lateral meniscus and lateral defects were repaired with a previously cryopreserved meniscal tissue from medial meniscus, to demonstrate the versatility of a previously cryopreserved meniscal tissue for repairing defects in any side of the knee. A fixed load of 2.3-2.5× body weight was applied to human cadaveric knees fixed to a mechanical test system at 15° of flexion to simulate the moment in a natural walking gait cycle when peak forces are loaded on the knee joint. Pressure sensitive films (FujiFilm™) were inserted between lateral and medial meniscus and tibial cartilage prior to testing. For each experimental state, 3 replicate tests were conducted for a total of n=5 donor knees (right). Mean contact pressures for a defined region of interest and total contact area for each test were calculated to compare groups.

v. Conditioned Medium

Conditioned medium from meniscus tissue or previously cryopreserved meniscal tissue were collected to assess the effects of adding engineered channels or to compare cryopreserved to devitalized meniscal allografts that do not contain viable cells. In either case, pieces of meniscus from the same donor were cut into uniform sizes and split into different treatment groups for direct comparison. Pieces were placed in 6-well plates and submerged in 3 mL of culture medium (DMEM+10% FBS+1% anti-anti+2% GlutaMAX) and incubated at 37° C. for 4 weeks, with media changes at 1 week and 2 weeks. Conditioned medium volumes were recorded at each time point, aliquoted and stored at −80° C., and analyzed using ELISA for the release of angiogenic and chondrogenic growth factors.

vi. LPS-Induced TNF-α Secretion from a Previously Cryopreserved Meniscal Tissue

Unprocessed meniscus with synovial membrane and fatty tissue intact and final thawed previously cryopreserved meniscal tissue units were placed in DMEM+10% FBS and exposed to bacterial LPS (1 µg/mL, Sigma) for 24±1 hours. After 24 hours, tissue culture supernatants were collected and tested for the presence of TNF-α via ELISA. Human hPBMCs, known to secrete high levels of TNF-α upon LPS stimulation, were used as a positive control in the assay. hPBMCs, unprocessed meniscus, and previously cryopreserved meniscal tissue without LPS were included as controls in the analysis.

vii. FACS Analysis of a Previously Cryopreserved Meniscal Tissue

FACS was performed using single-color analysis on a FACS Calibur System (Becton-Dickinson) using CELLQuest Software on enzyme extracted cells. A cryopreserved meniscal tissue was thawed in 37±+2° C. water bath for 5-10 minutes, washed in DMEM, and incubated in a pronase (Roche) for 1.5 hours followed by collagenase type II (Worthington) solution overnight on a rocker at 37±2° C. Collagenase solution was decanted over a 100 µm cell strainer and the digested tissue was rinsed in DMEM and decanted through the same cell strainer for a final volume of 45 mL of strained cell solution. The cell solution was centrifuged at 18000±1000 rpm for 10 min±5 min. and the cell pellet was resuspended in 1-5 mL DMEM. The isolated cells were counted and 1 M cells were plated on a T75 tissue culture flask and cultured for 7 days in DMEM+10% FBS with medium changes every 2-3 days. At Day 7, cells were detached using 0.05% trypsin-EDTA, counted using a hemacytometer, and resuspended at 2.5 M cells/ml in order to test 250,000 cells per FACS sample. Bone marrow-derived MSCs (P2) were thawed, resuspended at the same cell concentration, and used as a control cell type for this experiment. They were incubated in FACS buffer (DPBS+ 5% BSA and 0.001% sodium azide) with antibodies to CD105, CD166, CD45, CD31 or isotype control. The cells were then fixed with 1% Paraformaldehyde prior to analysis on a FACS Calibur system (BD Technologies). Data was analyzed with CellQuest Software (BD Technologies) and the hMSC isotype control sample was used to determine gating for all other samples.

2. Results a. A Previously Cryopreserved Meniscal Tissue Preserves all Vascular and Avascular Zones of Native Human Meniscal Tissue The meniscus naturally sits between the two knee bones inside the joint space and is loosely attached to the synovium that defines the joint space. The outer regions of the meniscus, closest to the synovium, are vascularized, while the inner region of the meniscus, closest to the center of the joint, is avascular. Traditionally, the meniscus has been divided into three distinct zones, the outermost third (2-3 mm) is called the red zone, the middle third is called the red-white zone (3-4 mm), and the innermost third is called the white zone (3-5 mm) (see FIG. 1). In native meniscal tissue, only the red zone and red-white zone contain functional blood vessels. The white zone is avascular and does not contain blood vessels.

Meniscus tears in the red zone of the meniscus are the only tears that can spontaneously heal after injury, likely owing to the vasculature and higher level of progenitor cell infiltration and growth factor release. The red-white zone contains some smaller blood vessels, but tears in this region rarely heal. Tears in the white zone do not self-repair.

A previously cryopreserved meniscal tissue was developed to include all three zones of the meniscus, including the red zone, while still removing all fatty, immunogenic connective tissue from the joint capsule and selectively killing cells of hematopoietic origin during cryopreservation (see immunogenicity and FACS). The previously cryopreserved meniscal tissue can be sutured into a meniscal defect after partial meniscectomy and the red zone, which was selectively altered during cryopreservation, of the previously cryopreserved meniscal tissue can be in direct contact with the red zone of the patient's meniscus.

Histology staining of the previously cryopreserved meniscal tissue confirmed that the native protein structure and proteoglycan content of intact human meniscus are retained after processing, and all three zones are retained. The red zone is fully retained, including the native structures of blood vessels naturally present in this zone. While structures of blood vessels were found, immunogenicity and FACS analysis confirmed the lack of CD45+ hematopoietic cells, the lack of CD31+ endothelial cells, and the lack of an immune response by cryopreserved meniscal tissue.

The previously cryopreserved meniscal tissue preserves all three regions of native human meniscus.

b. Methods for Creating Engineered Channels in Meniscal Tissue

Integration of a previously cryopreserved meniscal tissue with healthy patient meniscus is essential to successful repair of the meniscus and positive clinical outcomes. In order to promote healing and integration of a previously cryopreserved meniscal tissue with the patient's healthy meniscus tissue, two actions were taken during product development. First, the vascularized outer third of the meniscus known as the "red zone" was fully retained though was deprived of viable immunogenic cells. The second means of promoting integration was to generate microscopic engineered channels within the red zone of the meniscal tissue. These engineered channels were hypothesized to facilitate growth factor release and progenitor cell and meniscus cell penetration and attachment.

Figure 2:
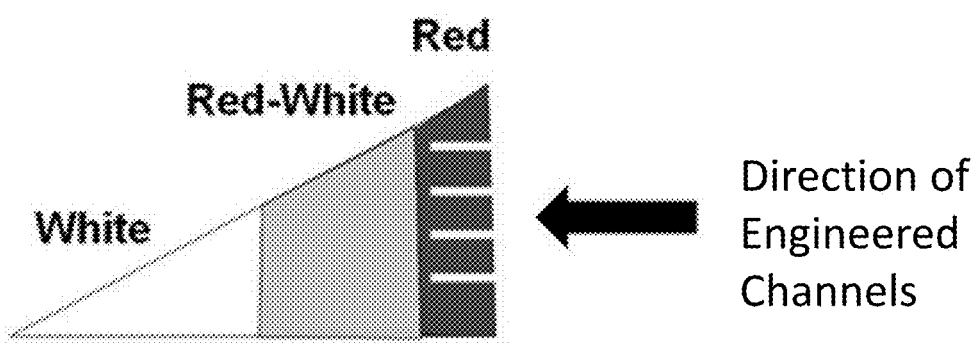
FIG. 2 shows a schematic of meniscal tissue showing the preserved red zone or altered red zone and an exemplary direction of engineered channels cut into the red zone or altered red zone.

Engineered channels were selected over full-thickness pores in order to minimize the total tissue disruption, which could adversely affect the mechanical strength and function. Furthermore, engineered channels were only created within the red zone or red-white zone of the meniscal tissue, as this is the area known to contain higher levels of growth factors and the area that will be in direct contact with the patient's meniscus and serve as the integration interface (See FIG. 2).

Different methods for generating engineered channels were tested and later scored for their efficiency in generating engineered channels quickly, ability to create evenly spaced engineered channels along the entire peripheral surface area, final appearance of engineered channels (and removal of excess tissue), and safety for the user. Table 1 shows the results of this analysis.

TABLE 1

Evaluation of Methods for Forming Engineered channels in Meniscal Tissue

| | | Evaluation Criteria | | | | |
|---|---|---|---|---|---|---|
| Method | Engineered Channel Dimensions | Efficiency | Evenness of Engineered Channels | Final Appearance | Safety | Final Score |
| 18 g needle | ~1 mm diameter, Variable length | 2 | 1 | 2 | 4 | 9 |
| 1.0 mm biopsy punch | 1 mm diameter, Variable length | 1 | 1 | 1 | 4 | 7 |
| 0.2 mm biopsy punch | 0.2 mm diameter, variable length | 1 | 1 | 1 | 4 | 7 |
| Microdermal roller (0.2 mm diameter, 1 to 3 mm long) | 0.2 mm diameter, 1 to 3 mm length | 3 | 5 | 5 | 2 | 15 |
| Custom Tool | 0.5 mm diameter, 3 mm length | 4 | 5 | 5 | 5 | 19 |

Needles and biopsy punches, while safe for the user, were difficult to accurately and repeatedly make engineered channels in the proper orientation and with even spacing along the entire edge of the meniscus. Meniscus tissue is also much softer than hyaline cartilage, which led much of the tissue to remain stuck inside and not be easily removed with punches. Furthermore, the time required to create each engineered channel individually was judged to be too long.

Figure 3:
FIG. 3 shows an image of a microdermal roller alongside meniscus after perforation of the meniscus to define a plurality of engineered channels as disclosed herein. The roller was dipped in crystal violet dye and then used to form engineered channels to better visualize the engineered channel patterns.

Microdermal rollers are available as single-use terminally sterilized products from various international manufacturers of unknown quality. These rollers have over 500 titanium spikes measuring 0.2 mm in diameter in a range of lengths from 0.2 to 3 mm. The spikes are evenly spaced in rows that cover the full circumference of a small wheel attached to a handle. The microdermal rollers can make evenly spaced engineered channels, and the spikes pierce the meniscus tissue rather than cut away plugs for a better appearance than biopsy punches (see FIG. 3).

However, the meniscus has a slippery, low friction surface and small size that is difficult for the user to hold while pushing into the roller spikes. Additionally, the wheel feature of the roller allows for sudden slips of the hand and a higher risk to the user while making engineered channels.

Figure 4:
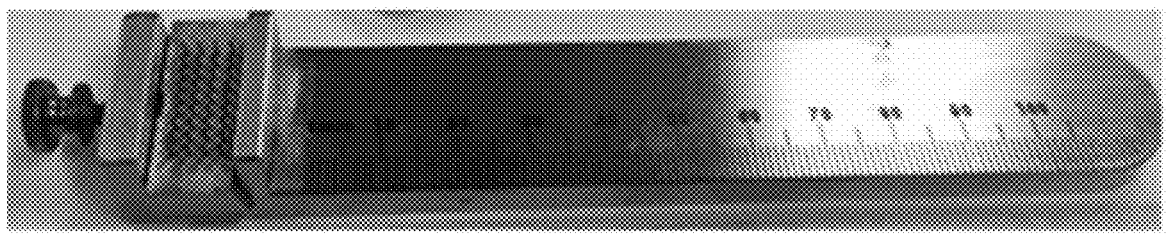
FIG. 4 shows an image of an exemplary custom engineered channel-forming tool for forming engineered channels into meniscal tissues as described herein.

To improve safety, a custom engineered channel tool was produced out of medical grade stainless steel (FIG. 4). This tool is autoclavable, reusable, and contains an array of microscopic metal pins (0.5 mm in diameter, 3 mm in length) that fits between two metal guard rails. The array of pins is removable for easier cleaning and to repair any pins that may bend over time. The pins are not sharp on the end, which greatly reduces the risk to the user.

Figure 5:
FIG. 5 shows an Hematoxylin and Eosin (H&E) stain of a meniscal tissue altered red zone showing one possible orientation of engineered channels created with a microdermal roller.

A rectangular cross section of the altered red zone of a thawed unit of a previously cryopreserved meniscal tissue was cut and stained to confirm the presence of equally spaced, microscopic engineered channels in the product (FIG. 5).

Figures 6A, 6B:
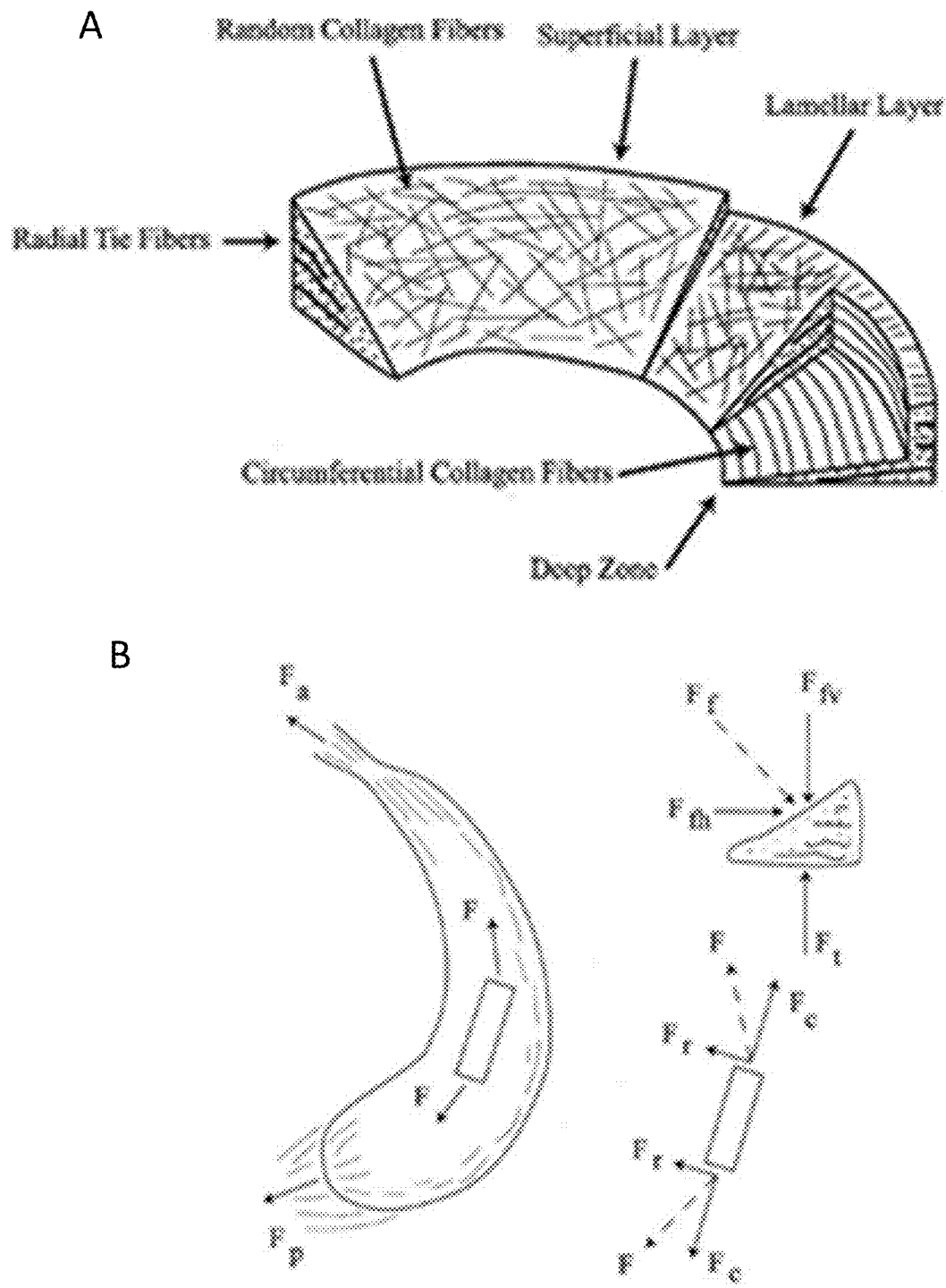
FIGS. 6A and 6B show a schematic diagram of collagen layers and hoop stresses of a human meniscal tissue. A) Sketch of the orientation of collagen fibers within the superficial, lamellar, and deep layers of the meniscus. B) Depiction of the forces acting on the meniscus as axial loads from the femur (Ff) are transmitted into circumferential hoop stresses within the meniscal tissue (Fa and Fp). Images from Sweigart and Athanasiou, 2001 *Tissue engineering* 7.2 (2001): 111-129.

Based on the grading system developed above, the best and safest method for producing engineered channels in meniscal tissue is using the custom engineered channel tool.

c. A Previously Cryopreserved Meniscal Tissue Preserves all Collagen Layers of Human Meniscus The hallmark function of the meniscus is its ability to distribute load from the femur along the entire surface of the tibial plateau. The meniscus does so by converting axial loads from the femur into "hoop stresses" that span the entire circumference of the meniscus and off-load the cartilage underlying the meniscus on the tibial plateau. Conversion of loads into hoop stresses is achieved by the unique organization of collagen fibers within the meniscus. (see FIG. 6)

The structure of collagen fibers in the meniscus is different from top to bottom, with randomly oriented collagen fibers in the superficial (top) zone that gradually transition to more organized fibers in the lamellar (middle) zone and then fully aligned circumferential collagen fibers in the deep (bottom) zone.

Differences in the mechanical function of top and bottom halves of a previously cryopreserved meniscal tissue were tested using pressure sensitive film (FujiFilm) to determine the contact pressures on the tibia for a "top" piece compared to a "bottom" piece. To safely and repeatedly generate half-thickness pieces, porous polyurethane foam (generic variety from packing material, source unknown) was cut into a semi-circular shape, sliced down the middle with a scalpel, and used to hold a whole meniscus in place while making a horizontal cut to split the meniscus into top and bottom halves.

To test differences between top and bottom halves, tibial contact pressures were measured for a human cadaveric knee affixed to a mechanical test machine when a fixed static load was applied using pressure sensitive film. Once a fixed force was applied, the film changes colors depending upon the magnitude of pressure sensed and can be converted to a pressure magnitude using a predetermined calibration scale.

Pilot test results showed that a "top" half had inferior mechanical function compared to a "bottom" half. The "bottom" half led to tibial contact pressure patterns very similar to the uninjured meniscus state, whereas the "top" half had little effect on restoring contact pressures and was closer in pattern to the injured state.

d. Final Dimensions of a Previously Cryopreserved Meniscal Tissue

Figure 7:
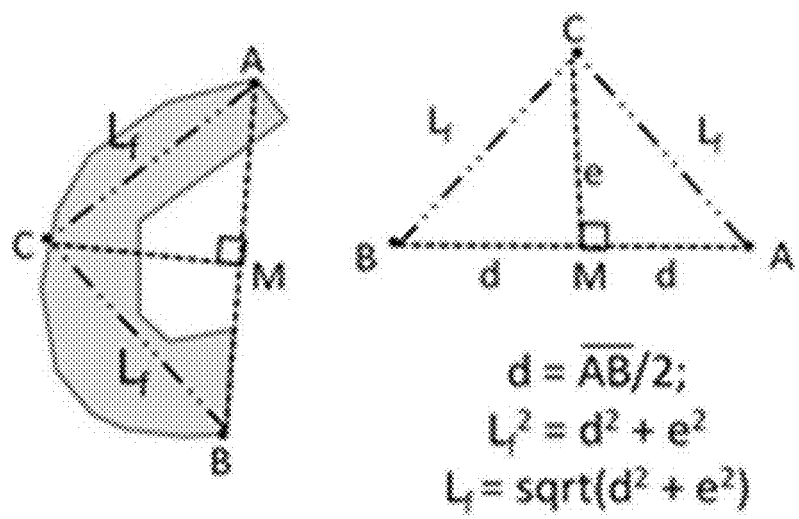
FIG. 7 shows a schematic representing a method for predicting the outer corner-to-corner length of a 50% defect from the length and width measurements of a whole meniscus. The AB and MC distances were previously measured for 18 lots. Using this data, Lf was calculated for each lot.

A previously cryopreserved meniscal tissue can be used to treat any size meniscal defect, including a full meniscal defect. In some instances, a previously cryopreserved meniscal tissue can be developed to treat up to a 50% defect and these meniscal tissues can be used for both medial and lateral repair. For 18 separate lots representing starting material from male and female donors of a wide range of ages (mean=50 years, range 18 to 73 yo), body weights, and body heights, the mean length of a 50% defect was 24.5 mm+/−3.2 mm. This mean length matched well with the mean L of FIG. 7. Therefore, the minimum L for a meniscal tissue to treat up to 50% defects in the majority of patients was found to be 25 mm.

Therefore, in one example, a range of dimensions for a previously cryopreserved meniscal tissue was found to be: L=26+/−1 mm and W=11+/−2 mm, which should be large enough to treat up to 50% defects in the majority of patients while still maximizing the yield from each lot.

e. Versatility of a Previously Cryopreserved Meniscal Tissue to Treat Medial and Lateral Defects The medial and lateral meniscus in humans and other species have distinct shapes, due to the shape of the femur bone and different profile of forces applied to the inside (medial) and outside (lateral) regions of the knee. In humans, the medial meniscus is shaped like a C and becomes gradually wider from the front (anterior) to the back (posterior) of the knee, while the lateral meniscus is shaped like a closed C and is more symmetrical from anterior to posterior. In general, the medial meniscus is slightly larger than the lateral meniscus for most people.

Figure 8:
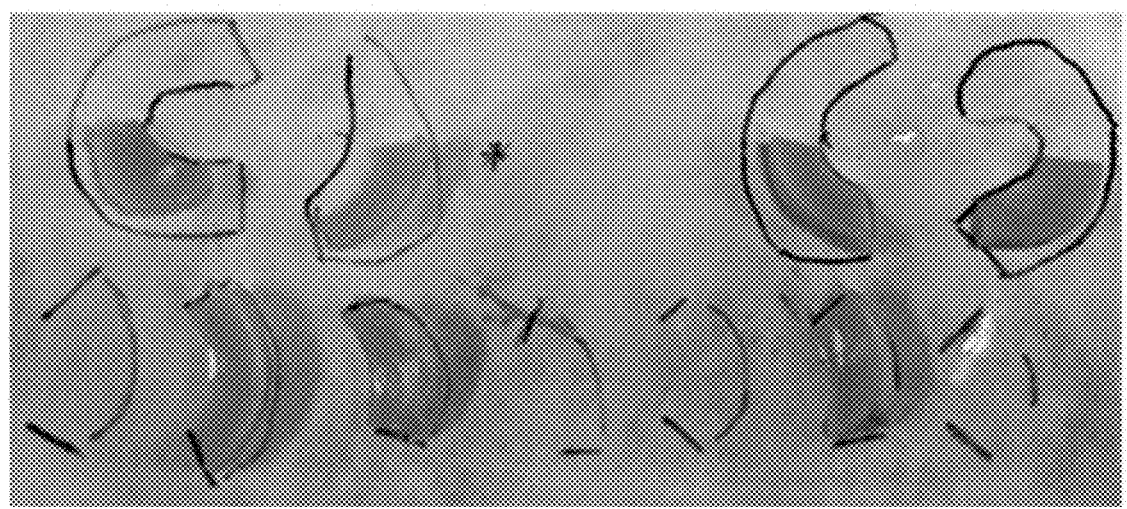
FIG. 8 demonstrates the versatility of the compositions described herein to treat both lateral and medial defects.

A previously cryopreserved meniscal tissue was designed to treat both medial and lateral defects, rather than having two separate products specific to the sides of the knee. The development of specific size ranges for the previously cryopreserved meniscal tissue helped to make this possible. As shown in FIG. 8, treatment of medial and lateral defects <50% of the total volume of the meniscus can be achieved for both medial and lateral sides with the same unit of a previously cryopreserved meniscal tissue. In many cases, after processing a lot of a previously cryopreserved meniscal tissue, it becomes difficult to determine if a given 25 mm unit originated from a medial or lateral meniscus. It is important to note that if previously cryopreserved meniscal tissues were ever enlarged to treat >50% defects, this feature of versatility would disappear and separate medial and lateral versions of the product would be necessary.

Figure 9:
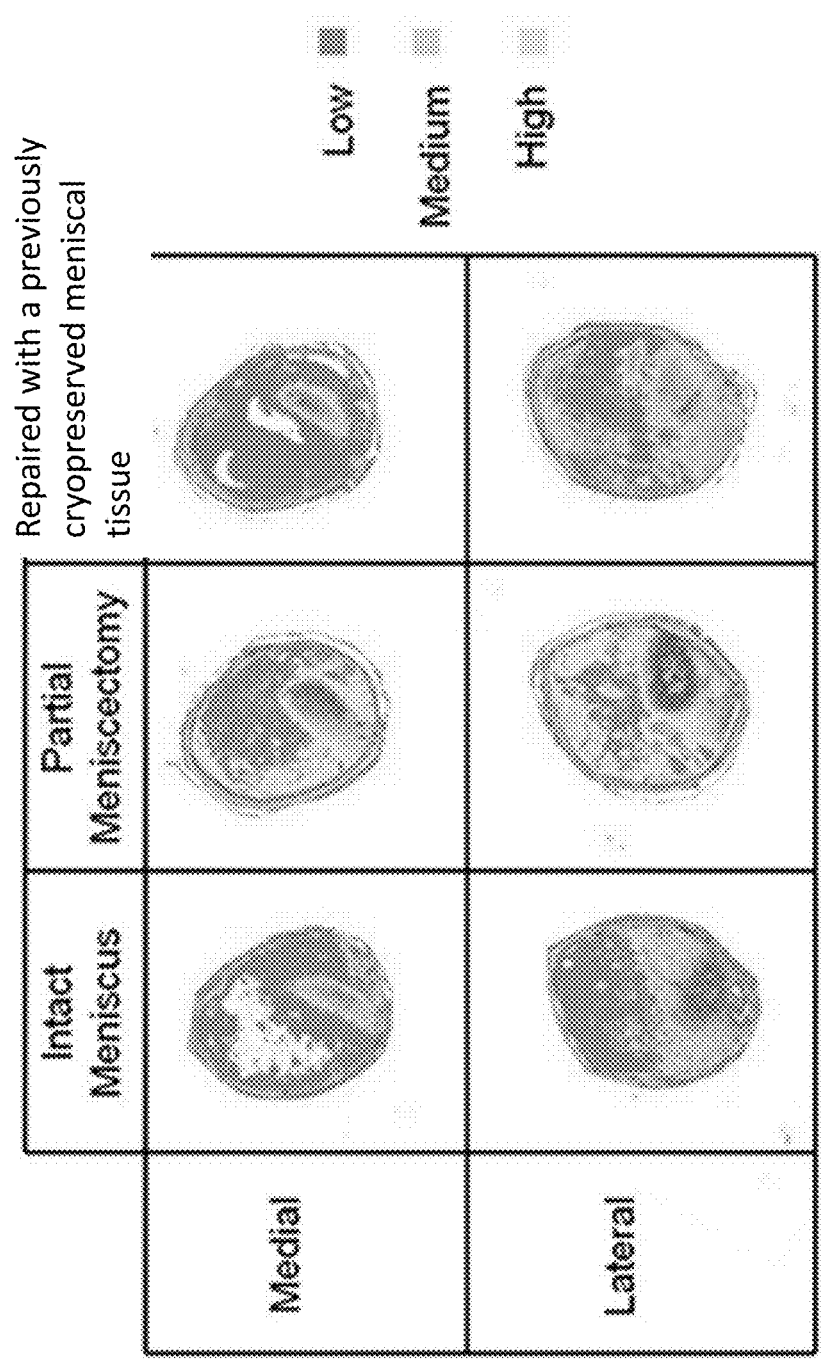
FIG. 9 shows a tibial contact pressure testing with a previously cryopreserved meniscal tissue illustrating the biomechanical function of a previously cryopreserved meniscal tissue upon implantation and return to intact state pressure distributions.

The versatility of a previously cryopreserved meniscal tissue was confirmed using tibial contact pressure testing. For one medial and one lateral defect, a previously cryopreserved meniscal tissue derived from a lateral meniscus and a previously cryopreserved meniscal tissue derived from a medial unit were used to repair the defects, respectively. In both cases, a previously cryopreserved meniscal tissue protected the underlying cartilage and led to a pressure pattern identical to the intact, uninjured state (FIG. 9).

Figure 15:
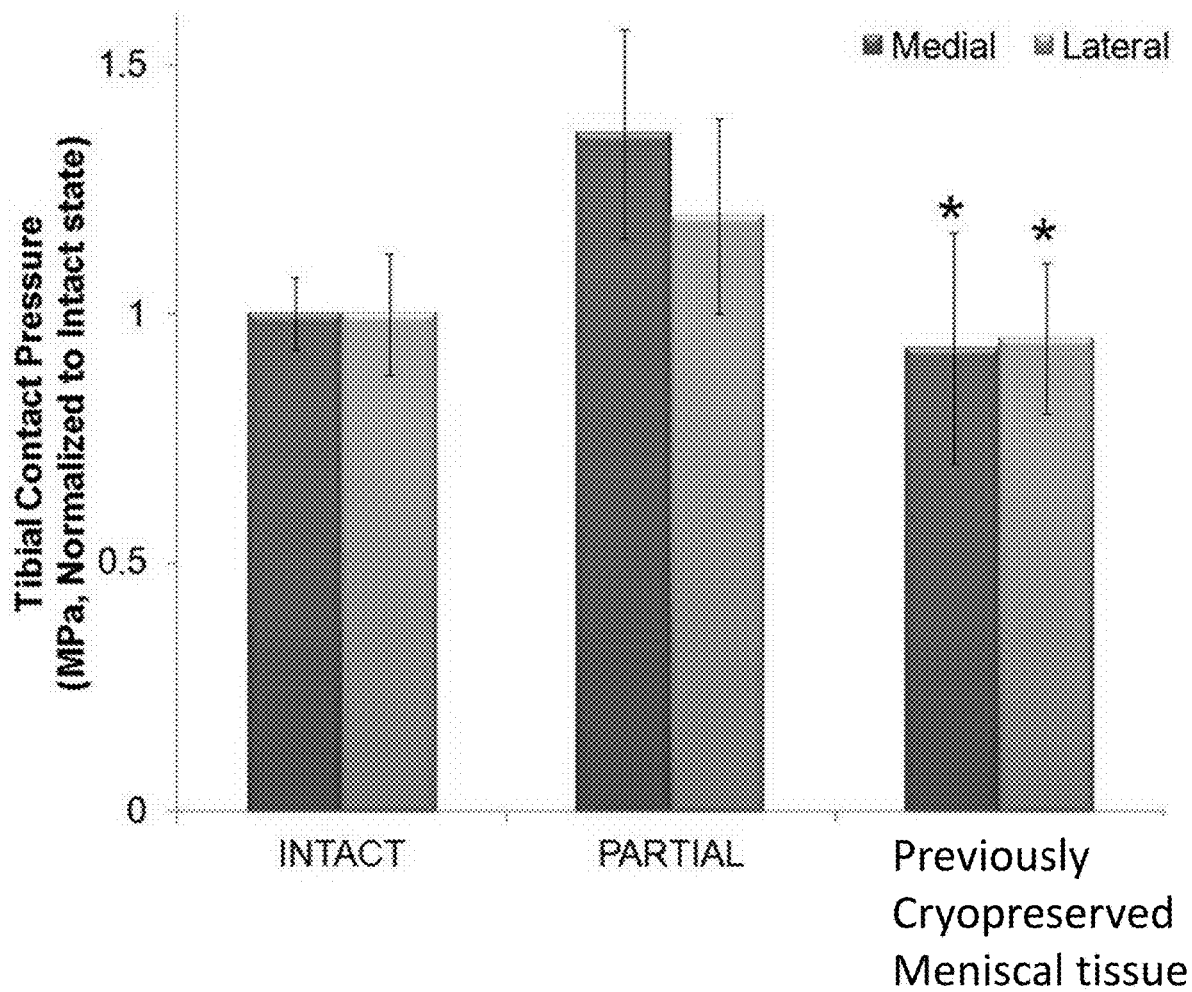
FIG. 15 is a bar graph showing mean tibial contact pressures on human cadaveric knee joints for three experimental states. Previously cryopreserved meniscal tissue led to a statistically significant drop in contact pressures for both medial and lateral defects (n=5 donors, $p<0.0001$) and was not different from the intact state.

Quantification of mean pressures detected on the tibial plateau for three states, intact state, partial meniscectomy state, and repair with a previously cryopreserved meniscal tissue after partial meniscectomy, indicated that the previously cryopreserved meniscal tissue protects the underlying cartilage from the excessive forces caused by partial meniscectomy immediately after implantation and before any healing or integration has taken place (FIG. 15, bar graph of pressures)

Previously cryopreserved meniscal tissue can be used to repair medial or lateral defects.

f. A Previously Cryopreserved Meniscal Tissue's Cells Adhere and Proliferate In Vitro To confirm the presence of viable meniscal cells in a previously cryopreserved meniscal tissue, units of a cryopreserved meniscal tissue were thawed, washed in sterile saline, minced into 1×1×1 mm cubes with a scalpel, and sequentially incubated in a pronase solution (Roche) for 1.5 hours followed by a collagenase solution (Worthington Type II) for 18 hours on a rocker at 37+2° C. (based on method by Sanchez-Adams et al., (Tissue Engineering Part C: Methods 18.3 (2011): 235-243). At the conclusion of digestion, the collagenase solution was decanted over a 100 µm cell strainer and the digested tissue was rinsed in DMEM and decanted through the same cell strainer. The cell solution was centrifuged at 1800 rpm for 10 min. The cell pellet was resuspended in 2 mL meniscus culture medium (DMEM with 10% FBS, 1% anti-anti, 2% Glutamax, and 50 µg/ml ascorbic acid-2-phosphate) and cells were seeded on tissue culture flasks. In most cases, 1-2 million cells can be isolated from 1 gram of tissue.

Cells were seen adhering and expanding from the plated cell pellets after 72 hours. At 72 hours, two distinct cell populations were observed, a polygonal, rounded chondrocyte-like cell type and a spread-out fibroblast-like cell type, as has been previously reported for meniscal cell cultures. After 10 days in culture, 5.4 M cells were counted and passaged. Over 2 weeks, cells were passaged 3 times and frozen down at each passage to generate stocks of primary human meniscal cells.

Cells isolated from a previously cryopreserved meniscal tissue after 3 days in culture. Two native cells types are evident, rounded chondrocyte-like cells and spread-out fibroblast-like cells.

Figure 10:
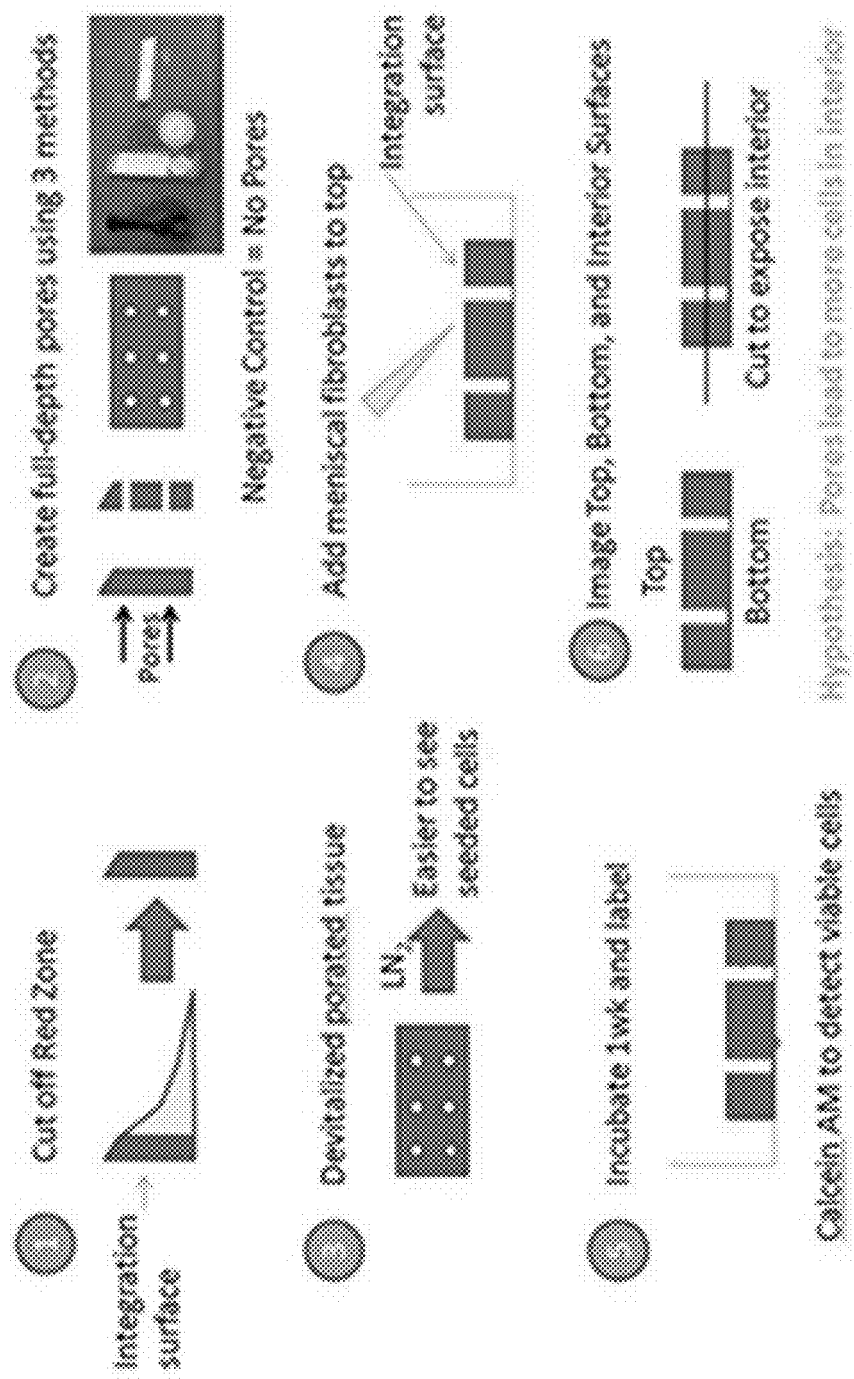
FIG. 10 is a schematic of a cell attachment assay for a meniscal tissue or previously cryopreserved meniscal tissue red zone or altered red zone segments with and without engineered channels.

Viable cells in a previously cryopreserved meniscal tissue can be isolated enzymatically, can adhere to tissue culture plastic, and can proliferate in vitro.

g. Engineered Channels within a Previously Cryopreserved Meniscal Tissue Promote Cell Attachment and Tissue Penetration To demonstrate the effects of engineered channels added to the red zone of a previously cryopreserved meniscal tissue on cell attachment and penetration into meniscus tissue, an experiment was conducted using meniscus cells isolated from the previously cryopreserved meniscal tissue and red zone segments of the previously cryopreserved meniscal tissue with and without engineered channels (FIG. 10). For this experiment, red zone segments were first devitalized by snap freezing with dry ice so that attaching cells could be more easily distinguished. Engineered channels were made in red zone segments using an 18 gauge needle, microdermal roller, or 1 mm biopsy punch, and red zone segments without engineered channelsserved as the negative control. Segments were placed in 6-well plates and 100 µl of meniscal fibrochondrocytes (1M cells/ml, 100,000 cells total) in culture medium was carefully ejected onto the integration interface and allowed to attach for 5 min. before slowly adding enough culture medium to fully submerge the segment.

Segments and meniscal cells were incubated for 1 week and then stained with calcein-AM to visualize attaching cells. To assess the degree of penetration into the interior of the tissue segments, slices of each red zone segments were taken from the top, bottom, and interior. Only tissue segments with engineered channels had any cells within the interior, and cells could be seen coating the entire surface area of the engineered channels.

A similar experiment was performed using hMSCs as the attaching cell type and without first devitalizing the meniscus tissue segments. Because hMSCs appear to be significantly larger than the majority of viable meniscus cells within a previously cryopreserved meniscal tissue, devitalizing the meniscus tissue was not needed. Using the 1 mm biopsy punch as an example engineered channel, 100,000 hMSCs were added in 100 ul of culture medium to each tissue segment and allowed to incubated at 37° C. for 2 weeks with culture medium changes every 3-4 days.

A previously cryopreserved meniscal tissue's cells and hMSCs can adhere to a previously cryopreserved meniscal tissue tissue segments, and engineered channels promote deeper penetration of attaching cells into the tissue, which can positively affect allograft integration in vivo.

h. Growth Factors in a Previously Cryopreserved Meniscal Tissue

A previously cryopreserved meniscal tissue is composed of viable meniscal cells, growth factors, and extracellular matrix identical to intact native human meniscus. Previously cryopreserved meniscal tissue extracts were analyzed by ELISA for presence of growth factors (Table 3).

TABLE 3

Growth Factors Present in previously cryopreserved meniscal tissue (adapted from Makris et al., 2011 Biomaterials 32.30 (2011): 7411-7431)

Figure 11:
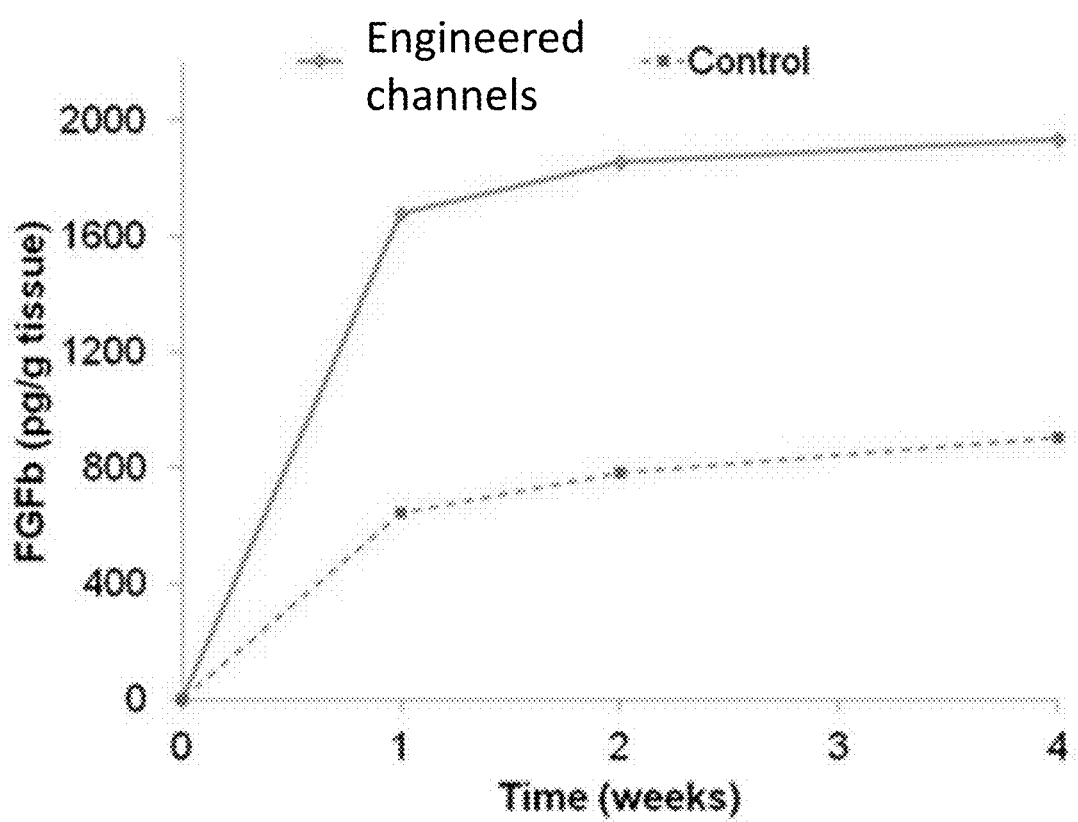
FIG. 11 is a graph showing the release of basic FGF from a cryopreserved meniscal tissue with and without engineered channels over 4 weeks.

| Growth Factor | Role in Meniscus Repair |
| --- | --- |
| TGF-$\beta$1 | Chondrogenesis/Collagen and Proteoglycan Synthesis/Cell proliferation |
| bFGF | Angiogenesis/Collagen and Proteoglycan Synthesis/Cell migration and proliferation |
| PDGF-AB | Collagen and Proteoglycan Synthesis/Cell Migration and Proliferation |
| IGF-1 | Collagen and Proteoglycan Synthesis/Cell Migration and Proliferation |
| HGF | Cell Proliferation and Migration | i. Previously Cryopreserved Meniscal Tissue Engineered Channels Increase the Release of Basic FGF In Vitro To demonstrate the effect of adding engineered channels to the red zone of Menvivo, whole pieces of cryopreserved meniscus (n=2 lots) without engineered channels were thawed and cut into ~25 mm units. Of these units, half served as controls without engineered channels and half were perforated with a microdermal roller to create engineered channels in the red zone. Pieces were placed in 6-well plates and submerged in 3 mL of culture medium (DMEM+10% FBS+1% anti-anti+2% GlutaMAX) and incubated at 37° C. for 4 weeks, with media changes at 1 week and 2 weeks. Conditioned medium volumes were recorded at each time point and analyzed using ELISA for the release of a key angiogenic growth factor, bFGF (FIG. 11).

Adding engineered channels to a previously cryopreserved meniscal tissue increases the release of basic FGF from the previously cryopreserved meniscal tissue, which can promote better integration in vivo.

j. Viable Cells within Menvivo Promote Greater Release of TGFb1 Over Time

Figure 12:
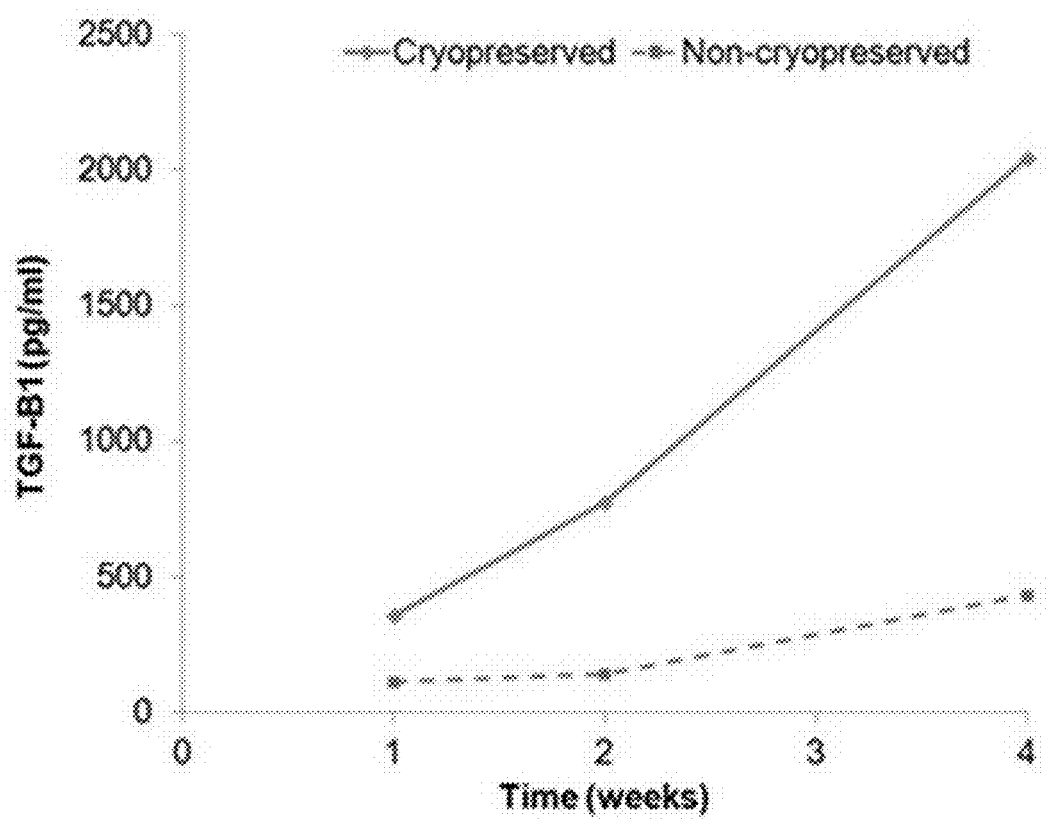
FIG. 12 is a graph showing the release of TGFb1 from cryopreserved meniscal tissue and devitalized (non-cryopreserved) meniscal tissue over 4 weeks.
Figure 13:
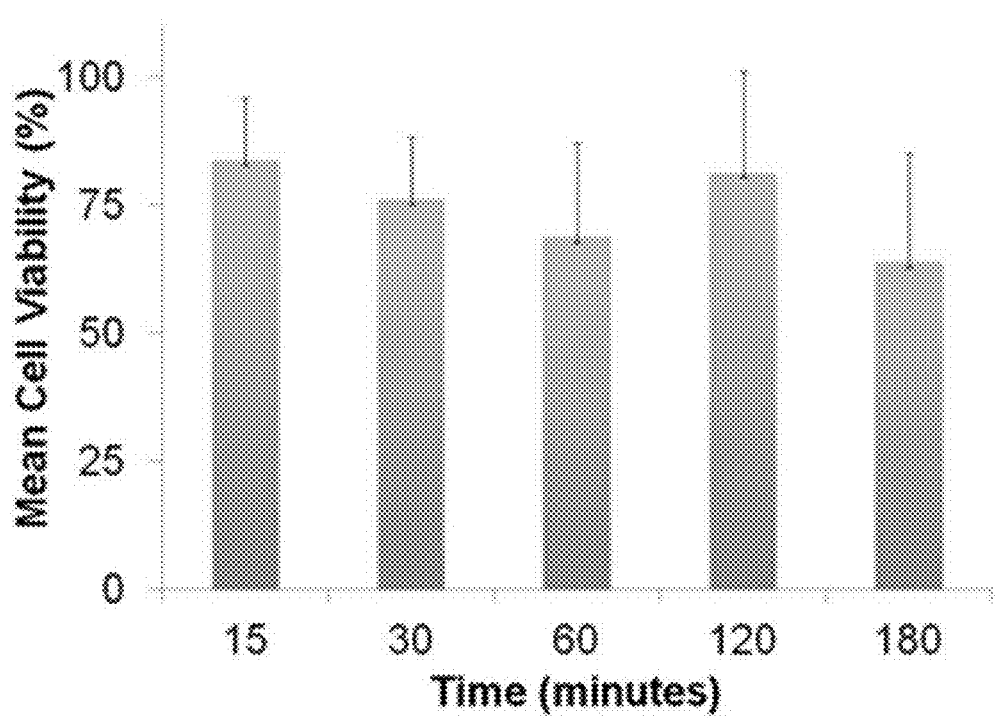
FIG. 13 is a graph showing the mean cell viability of meniscal tissue for different soaking times in cryopreservation solution (n=3 to 5 lots, mean+SD).

Preservation of cell viability within Menvivo tissue led to greater release of TGFb1 over time. Cryopreserved whole meniscus was thawed and engineered channels were formed with a microdermal roller in the red zone. Tissue pieces were cut in half into ~25 mm units and split into two groups: cryopreserved meniscus and non-cryopreserved meniscus. Non-cryopreserved meniscus was devitalized by successive cycles of snap freezing tissue in liquid nitrogen and thawing for 5 minutes in saline. As described above, pieces were incubated in hMSC medium for up to 4 weeks, and conditioned medium at 1 week, 2 weeks, and 4 weeks was analyzed using ELISA for the release of TGFb1 (FIG. 12).

Cryopreserved meniscus, which contains viable cells after thaw, releases more TGFb1 over time than non-cryopreserved meniscus.

k. Previously Cryopreserved Meniscal Tissue Promotes the Migration of Meniscal Cells In Vitro Growth factors naturally present in a previously cryopreserved meniscal tissue also retain the ability to elicit cell migration in a process known as chemotaxis. In this experiment, two cell types, human meniscal fibrochondrocytes isolated from a previously cryopreserved meniscal tissue and human MSCs, were tested. Cells were detached from culture plates, resuspended in DMEM at 250,000 cells/ml, and 200 µl (50,000 cells/well) were added to the top of a transwell filter (FluoroBlok™). Filters with cells were then submerged in 700 µl of DMEM (negative control), DMEM+ 20% FBS+2% GlutaMAX (positive control), or previously cryopreserved meniscal tissue conditioned medium. Conditioned medium was prepared by incubating segments of a previously cryopreserved meniscal tissue in DMEM for 72 h at 37° C. and was added to the bottom chamber of transwells undiluted. Cells were incubated at 37° C. and allowed to migrate for 24 h before washing the top side of the filters to remove cells that did not migrate. Cells that migrated to the bottom side of the filter were stained with calcein-AM and viewed with a microscope. Both cell types readily migrated toward the natural cocktail of growth factors released from a previously cryopreserved meniscal tissue, and did so in greater numbers than the positive control.

Previously cryopreserved meniscal tissue growth factors retain the bioactivity of chemotaxis, a key function for tissue repair, and can attract both meniscal cells and progenitor cells. Furthermore, the cells isolated from one lot of a previously cryopreserved meniscal tissue can actively migrate toward growth factors released from a different lot of a previously cryopreserved meniscal tissue—a demonstration of the role a previously cryopreserved meniscal tissue can play in meniscus repair in vivo.

ii. Antibiotic Treatment a. Effect of Length of Antibiotic Treatment on Cell Viability and Growth Factors in Meniscal Tissue (A) Cell Viability Meniscal tissue was treated with agentamycin, vancomycin and amphotericin B solution at a ratio of no more than 0.1 gram of meniscal tissue to 1 mL of antibiotic (up to 25 grams in 250 ml of antibiotic solution) at 37±2° C. and 5% $CO_2$ for 24 and 96 hours, cryopreserved, thawed, and then tested for cell viability using Live/Dead Staining. Cell viability after thawing was maintained for both antibiotic treatment times, and there was no change in cell viability observed between 24 h (74+/−24%) and 96 h (72+/−32%).

Treatment of meniscal tissue with the gentamycin, vancomycin and amphotericin B solution for up to 96 hours did not affect cell viability.

(B) Growth Factor Level

The retention of growth factors after treatment with antibiotics was evaluated. To ensure that growth factor levels are maintained, TGFb1 levels in previously cryopreserved meniscal tissue lysates from the same lot were compared after 24 hours or 96 hours of antibiotic treatment by ELISA. Mean TGFb1 levels from each antibiotic treatment are shown in Table 4.

TABLE 4

Comparison of TGFB1 levels after 24 and 96 hour antibiotic treatment

| Antibiotic Treatment (hours) | TGFβ1 Levels (pg/gram tissue) | | | % of 24 Hour |
|---|---|---|---|---|
| | Mean | St. Dev | % CV | |
| 24 | 4718 | 221 | 4.68 | 100 |
| 96 | 7102 | 358 | 5.04 | 150 |

TGFβ1 was present at high levels for 24 hour and 96 hour treatment with the gentamycin, vancomycin and amphotericin B solution.

iii. Freezing

Two desired properties of cryopreserved meniscal tissue are to have a long-term shelf-life when stored between −75° C. and −85° C. and to have viable cells upon thawing. To achieve this goal, optimization of the cryopreservation solution composition and freezing kinetics/process was required. For optimization experiments, Meniscal tissue precursor units (human meniscus with different dimensions and thicknesses) and final units were used to test different freezing conditions. Cell viability was used as the primary criterion for selection of the optimal freezing parameters, which were cryopreservation solution composition, soaking or submersion, chilling time, and temperature of the Styrofoam box used during freezing.

a. Cryopreservation Solution Composition

Initial experiments tested units from two donors that were split between four cryopreservation solutions all using Plasma-Lyte as the base solution: C1 (10% DMSO, 5% HSA), C2 (10% DMSO, 0% HSA), C3 (5% DMSO, 5% HSA), and C4 (5% DMSO, 0% HSA). Individual units of meniscal tissue were packaged in 15 mL Nalgene vials containing 10 mL of one solution, incubated for 60 minutes at 2-8° C. and then transferred to a styrofoam box pre-chilled to −80° C. and stored at −80° C. for freezing. After storage at −80° C. for at least 72 hours, units were thawed by placing in warm saline, removed from cryopreservation solution, and washed in saline. A thin slice from the top and bottom of each unit was made with a scalpel and cell viability was assessed by live dead staining. For each stained slice, at least 3 different fields of view were imaged at 10× magnification, and cells were hand-counted to quantify viability for each condition. Based upon this experiment, solution C4 was found to be the best solution and was further investigated.

TABLE 5

Viability data for different cryopreservation solutions (n = 2 donors)

| Solution | C1 | C2 | C3 | C4 |
|---|---|---|---|---|
| % DMSO | 10 | 10 | 5 | 5 |
| % HSA | 5 | 0 | 5 | 0 |
| Mean Viability (%) | 69.5 | 87.3 | 65.9 | 90.7 |
| Standard Deviation (%) | 4.1 | 4.9 | 5.6 | 1.5 |

Saline was also tested (C5), in place of Plasma-Lyte, as an alternative base for the cryopreservation solution. For two lots, no significant differences were detected between solutions C4 and C5.

iv. Menvivo Packaging/Storage

A meniscal tissue requires a primary storage container that has a large opening. Primary and secondary packaging should utilize existing manufacturing systems if possible. The 15 mL straight sided jars were selected and satisfied all requirements for meniscal tissue packaging. After placing one unit of meniscal tissue into a 15 mL straight sided jar, the lid was tightened using a Torque Wrench to 22 to 31 in·lbs, which is the manufacture's recommended pressure for this container. After tightening, the jar is sealed in a 4×7 inch mangar pouch to ensure sterility.

v. Thawing a Cryopreserved Meniscal Tissue

A cryopreserved meniscal tissue previously frozen and stored at −80±5° C. in jars were evaluated for the time required to thaw, which is defined as when a previously cryopreserved meniscal tissue can be easily compressed at the thickest spot using sterile surgical tools (forceps, spatula, etc.). Cryopreserved meniscal tissue samples were thawed by four methods: 1) sealed jar on a bench at room temperature, 2) directly adding RT saline to the jar with the cryopreserved meniscal tissue, 3) directly adding 37° C. saline to the jar with cryopreserved meniscal tissue, and 4) placing sealed jar into 37° C. water bath. Summary of results are in Table 8. Thawing of cryopreserved meniscal tissue was fastest by directly adding RT or warm saline.

TABLE 8

Evaluation of cry opreserved meniscal tissue Thaw Time

| Donor | Thawing Condition | Thaw Time |
|---|---|---|
| D1 | RT Saline | 3-4 minutes |
| D2 | RT Saline | 3-4 minutes |
| D1 | Warm Saline | 3-4 minutes |
| D2 | Warm Saline | 3-4 minutes |
| D1 | 37 C. Water Bath | 9-10 minutes |
| D2 | 37 C. Water Bath | 9-10 minutes |
| D1 | RT Benchtop | 45 minutes |
| D2 | RT Benchtop | 45 minutes |

Thawing cryopreserved meniscal tissue by directly adding RT or 37° C. saline is recommended.

vi. Post-Thaw Stability of Menvivo

Jars containing units of cryopreserved meniscal tissue from the same lot were partially thawed in RT saline for 1-2 minutes, just long enough to cut them in half for testing. At this time units were stored in sealed jars with or without RT saline for 1, 2, or 3 hours and then thin slices were taken from the top and bottom of each unit for live/dead staining to determine cell viability. For a baseline comparison, one unit from the same lot was thawed at the same time by adding RT saline and immediately evaluating with live/dead staining after thawing for a 0 hour baseline measure. Results are summarized in Table 9.

All samples tested at each time point contained viable cells. At each time point tested, RT Saline led to higher cell viability than RT Air. The lowest calculated viability, and only sample with aviability below baseline, was for RT Air at 2 hours.

Viable cells were present and maintained a high percent viability through three hours post thaw when stored with or without RT saline. Therefore, a previously cryopreserved meniscal tissue is considered stable 3 hr post-thaw at room temperature and should be stored in RT saline to improve viability.

TABLE 9

Previously cryopreserved meniscal tissue Post-Thaw Stability Results (n = 6 fields of view)

| Time (hr) | Thaw method | Mean Viability (%) | Standard deviation (%) |
|---|---|---|---|
| Baseline, 0 | RT Saline | 67.8 | 18.7 |
| 1 | RT Saline | 94.3 | 10.5 |
|  | RT Air | 85.0 | 14.5 |
| 2 | RT Saline | 78.8 | 13.4 |
|  | RT Air | 61.8 | 19.0 |
| 3 | RT Saline | 94.2 | 11.5 |
|  | RT Air | 86.6 | 6.7 | vii. Menvivo Cell Viability

For quantitative assessment cell viability in previously cryopreserved meniscal tissue lots, slices of tissue from the top and bottom layer of each recently thawed 4 mm unit were incubated in live/dead stain and viewed under a microscope. For each slice of tissue, at least 3 different representative fields of view were imaged at 10× magnification, and live and dead cells were hand counted to determine percent viability for each field. Mean cell viability across fields for each slice and for each sample were calculated, and mean cell viability for each lot was then calculated (Table 10).

TABLE 10

Evaluation of cell count and viability for previously cryopreserved meniscal tissue

| Lot | Donor Age | Mean Viability (%) |
|---|---|---|
| 1 | 33 | 74.7 |
| 2 | 51 | 88.8 |
| 3 | 53 | 73.1 |
| 4 | 22 | 46.7 |
| 5 | 45 | 88.3 |
| 6 | 27 | 81.2 |
| 7 | 36 | 73.0 |
| 8 | 41 | 90.6 |

The mean cell viability across 8 lots of previously cryopreserved meniscal tissue was found to be 77.0%±14.3%. On average, lots of previously cryopreserved meniscal tissue have >70% cell viability with an observed range of 50% to 90%.

viii. TGFb1 Levels in a Previously Cryopreserved Meniscal Tissue

Previously cryopreserved meniscal tissue lysates were prepared as described above. Guanidine-HCl extracts were prepared and desalted prior to testing, The level of TGFb1 was measured using the TGFb1 R&D Quantikine ELISA kit previously cryopreserved meniscal tissue lysates were prepared undiluted or diluted 1:2, 1:5, and 1:10 with calibrator diluent and then further diluted 1:2 in assay diluent per manufacturer's recommendation. Lysates diluted 1:5 were also spiked with 200 pg/ml of TGFb1 standard to determine accuracy of TGFb1 quantitation in tested tissue extracts. Experimental absorbance values were considered valid if they were above the lower level of detection (i.e. 3 fold greater than the background absorbance). Percent recovery was calculated by subtracting the expected value from the experimental value then dividing the difference by the expected value and subtracting the absolute value from 1. The expected value was calculated by adding the pg/ml of the sample to the pg/ml of the 200 pg/ml control. Formula: 1−[(Expected value−Experimental value)/(Expected value)]. Results are summarized in Table 11 and Table 12.

TABLE 11

TGFb1 levels in previously cryopreserved meniscal tissue lysates

| | | TGFβ1 levels | | |
|---|---|---|---|---|
| Lot | Tissue weight (g) | pg/mL | Std Dev | pg/mL/gram Tissue |
| D1 | 0.19 | 1575 | 40.8 | 8290 |
| D2 | 0.17 | 1158 | 7.52 | 6813 |
| D3 | 0.24 | 1479 | 14.9 | 6164 |
| D4 | 0.3 | 1133 | 43.6 | 3777 |
| D5 | 0.2 | 1420 | 71.6 | 7102 |
| D6 | 0.4 | 1018 | 130 | 2545 |

TABLE 12

TGFb1 spike recovery from previously cryopreserved meniscal tissue lysates

| | | TGFβ1 levels | | |
|---|---|---|---|---|
| Lot | Tissue weight (g) | pg/mL | pg/mL + 200 pg/mL TGFb1 | % Recovery |
| D1 | 0.2 | 226.2 | 417.5 | 100.6 |
| D2 | 0.5 | 161.3 | 352.3 | 106.1 |
| D3 | 0.3 | 205.1 | 396.4 | 103.4 |
| D4 | 0.3 | 117.4 | 322.8 | 112.0 |
| D5 | 0.2 | 180.8 | 386.2 | 106.2 |
| D6 | 0.4 | 129.9 | 335.3 | 105.1 |

TGFb1 is present in previously cryopreserved meniscal tissue and can be accurately quantified since more than 80% of the TGFb1 spiked into previously cryopreserved meniscal tissue lysates could be recovered.

ix. Immunogenicity Testing a. LPS-Induced TNF-α Secretion

The presence of viable endothelial cells, macrophages and other cells of hematopoietic origin plays a critical role in allograft rejection. Furthermore, devitalization of these types of cells in allogeneic donor tissue decreases the level of inflammatory cytokine secretion, such as TNF-α, which correlates with tissue immunogenicity. Reduction of tissue immunogenicity can be also reached by depletion of TNF with anti-TNF antibodies or suppression of TNF secretion. In contrast, the addition of exogenous TNF triggers allograft rejection. Viable endothelial and hematopoietic cells including macrophages respond to bacterial antigens (LPS) by secretion of inflammatory cytokines such as TNF-α. Thus, the presence of immunogenic cells can be detected by stimulating the allograft with LPS and monitoring TNF-α release. To demonstrate that the manufacturing process of a previously cryopreserved meniscal tissue generates a safe product with low immunogenicity, an in vitro assay was conducted to test for the presence of immunogenic cells by LPS-induced TNF-α secretion. Data from published reports indicate a correlation between levels of TNF-α less than 100 pg/ml and an absence or insignificant immune response in a variety of experimental systems.

Figure 14:
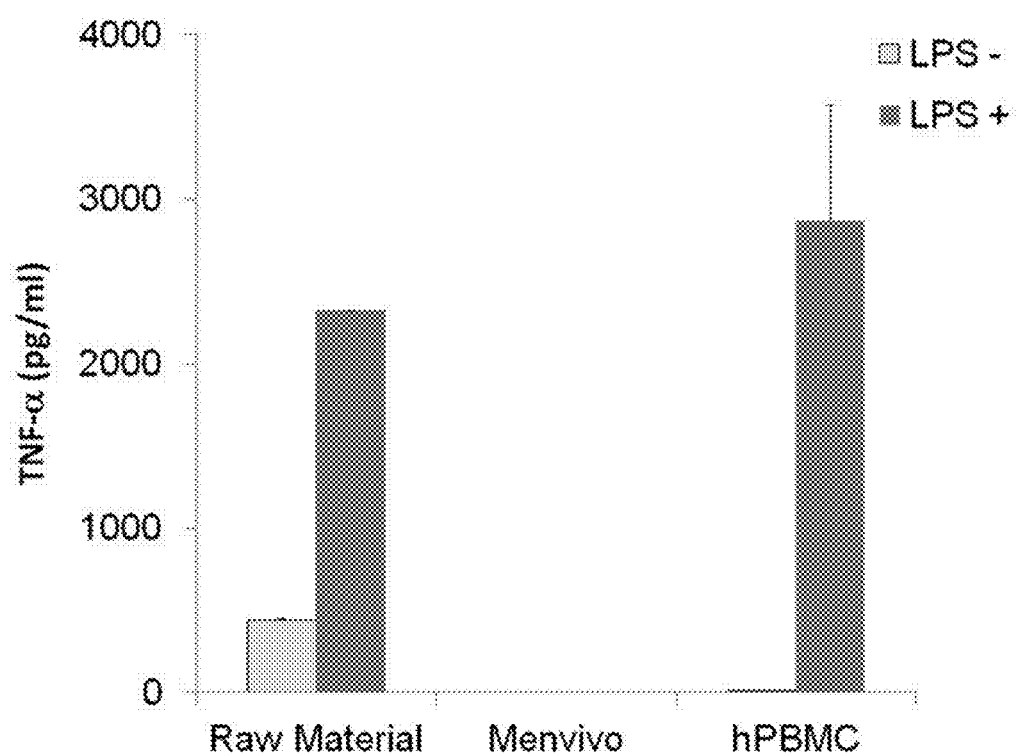
FIG. 14 is a graph showing LPS-induced TNF-α Secretion.

As shown in FIG. 14, the unprocessed raw meniscus material (n=1 lot) was immunogenic and responded to stimulation with LPS by producing levels of TNF-α 20 times higher than 100 pg/ml. The final previously cryopreserved meniscal tissue product was not immunogenic, as LPS stimulation did not lead to detectable levels of TNF.

b. Previously Cryopreserved Meniscal Tissue Cellular Composition by FACS: Absence of Immunogenic Cells FACS was performed using single-color analysis on a FACS Calibur System (Becton-Dickinson) using CELL-Quest Software on enzyme extracted cells. Cryopreserved meniscal tissue was thawed in 37±2° C. water bath for 5-10 minutes, washed in DMEM, and incubated in a pronase (Roche) for 1.5 hours followed by collagenase type II (Worthington) solution overnight on a rocker at 37±2° C. Collagenase solution was decanted over a 100 µm cell strainer and the digested tissue was rinsed in DMEM and decanted through the same cell strainer for a final volume of 45 mL of strained cell solution. The cell solution was centrifuged at 18000±1000 rpm for 10 min±5 min. and the cell pellet was resuspended in 1-5 mL DMEM. The isolated cells were counted and 1 M cells were plated on a T75 tissue culture flask and cultured for 7 days in DMEM+10% FBS with medium changes every 2-3 days. At Day 7, cells were detached using 0.05% trypsin-EDTA, counted using a hemacytometer, and resuspended at 2.5 M cells/ml in order to test 250,000 cells per FACS sample. Bone marrow-derived MSCs (P2) were thawed, resuspended at the same cell concentration, and used as a control cell type for this experiment. They were incubated in FACS buffer (DPBS+5% BSA and 0.001% sodium azide) with antibodies to CD105, CD166, CD45, CD31 or isotype control. The cells were then fixed with 1% Paraformaldehyde (1 ml of 4% paraformaldehyde and 3 ml of DPBS) prior to analysis on a FACS Calibur system (BD Technologies). Data was analyzed with CellQuest Software (BD Technologies) and the hMSC isotype control sample was used to determine gating for all other samples.

The cellular composition of the viable cells present in a previously cryopreserved meniscal tissue was characterized via fluorescence activated cell sorting (FACS). The identity of the population for MSCs was determined through the expression of CD105 and CD166. CD45 and CD31 cell surface markers were used to identify hematopoietic and endothelial cells, respectively.

Figure 25:
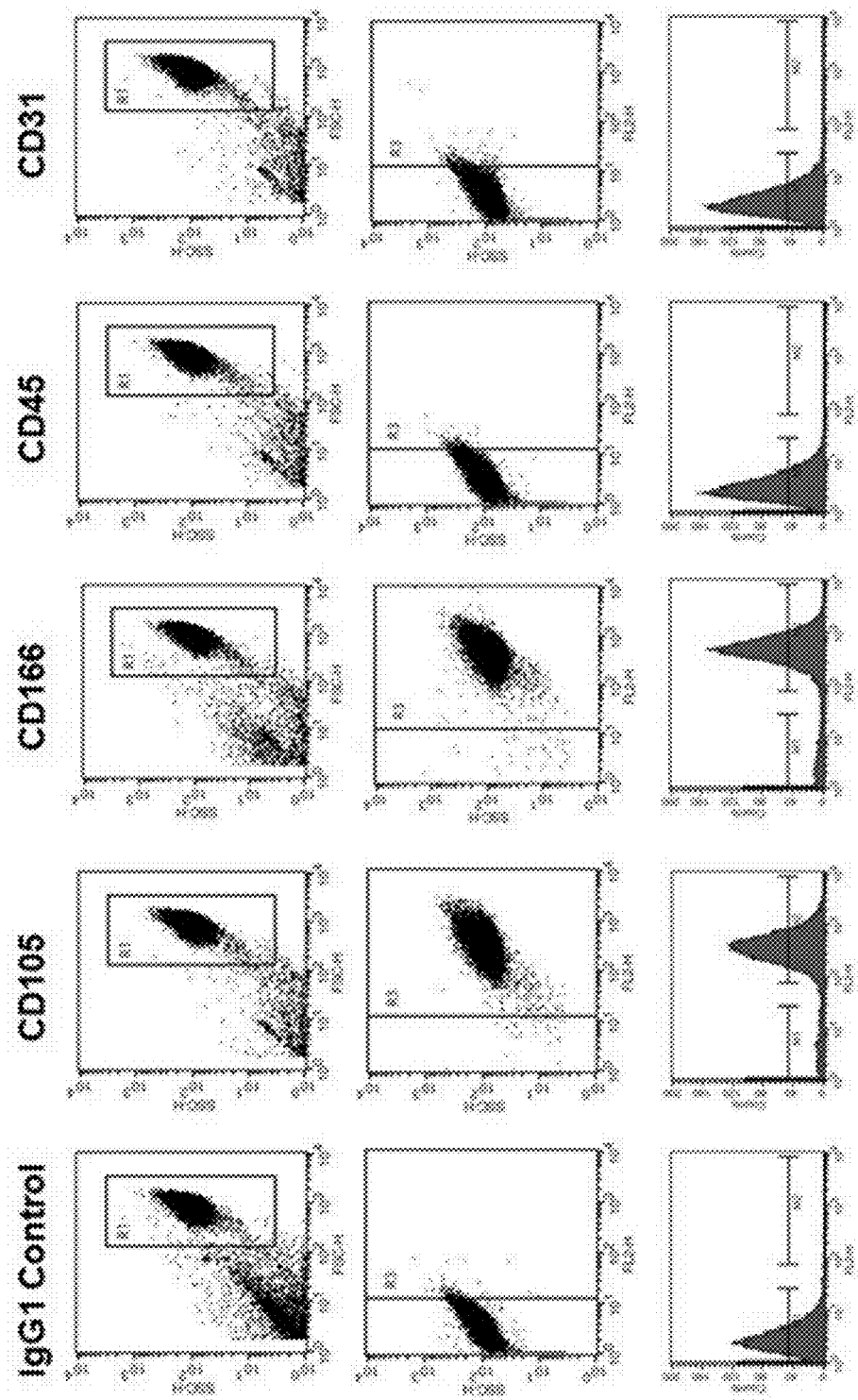
FIG. 25 shows FACS data images for hMSCs (Control). Top Row—Scatter plots of all recorded events showing cluster of cells of the typical size of hMSCs. Box R1 was defined based upon the IgG1 isotype Control. Middle Row—Results for the fluorescent channel corresponding to the fluorescent tag conjugated to each antibody. R3 represents the gate to differentiate noise from positively stained cells, as defined by the isotype control. Bottom Row—Histograms of each event showing the count of cells by signal intensity.
Figure 26:
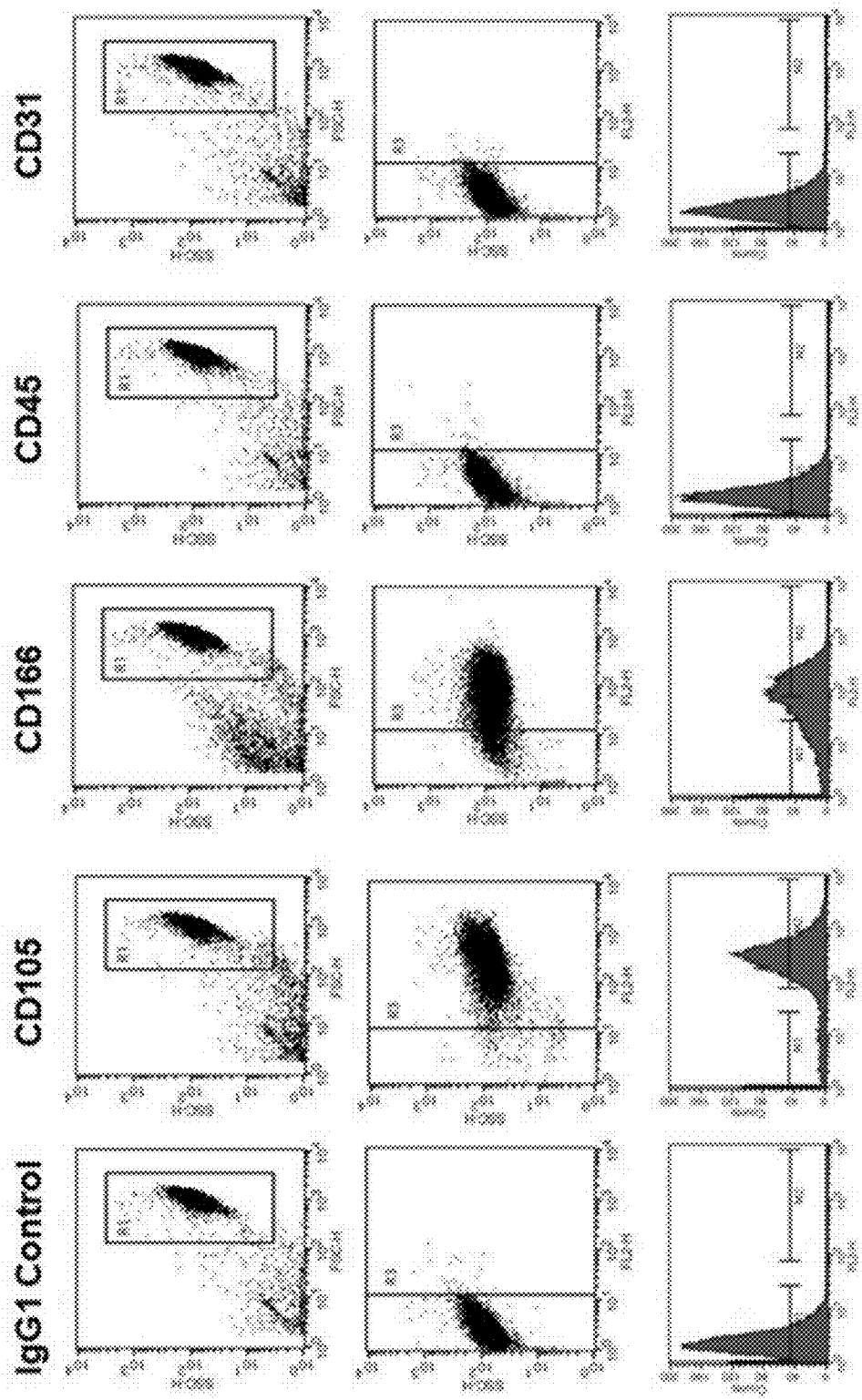
FIG. 26 shows FACS data images for cells isolated from a previously cryopreserved meniscal tissue. Using the same gating settings as defined by the hMSC isotype control from FIG. 25, a population of cells of similar size was detected for cells isolated from a previously cryopreserved meniscal tissue. The pattern of cell marker expression was consistent with hMSCs and was absent of immunogenic cell type markers, CD45 and CD31.

By FACS analysis, a previously cryopreserved meniscal tissue was shown to have a cellular profile consistent with MSCs and meniscal cells (Table 14, FIG. 25). Immunogenic CD45 (hematopoietic) and CD31 (endothelial)-positive cells were not detected in a previously cryopreserved meniscal tissue (FIG. 26).

TABLE 14

Cell Composition of a previously cryopreserved meniscal tissue

| Cell Marker | FACS Results | Marker Specificity |
|---|---|---|
| CD105 | Present | MSC |
| CD166 | Present | MSC |
| CD44 | Present | Chondrocyte-like |
| CD45 | Absent | Hematopoietic |
| CD31 | Absent | Endothelial |

TABLE 15

Percent of gated cells positively stained for cell surface markers

| | Surface Cell Marker | | | | |
|---|---|---|---|---|---|
| Cell Type | CD105 | CD166 | CD45 | CD31 | IgG1 |
| hMSC | 90.81 | 87.76 | 0.84 | 1.23 | 0.81 |
| previously cryopreserved meniscal tissue | 89.71 | 80.56 | 0.23 | 0.22 | 0.23 |

Conclusion: a previously cryopreserved meniscal tissue does not contain immunogenic cells.

A. Arthroscopic Implantation Technique

A previously cryopreserved meniscal tissue is a viable meniscal allograft that is able to repair the meniscus following partial meniscectomy or failed meniscal repair. Previously cryopreserved meniscal tissue contains viable endogenous meniscal cells, growth factors, and extracellular matrix identical to native human meniscus that will protect knee cartilage and restore knee biomechanics following injury. Previously cryopreserved meniscal tissue is designed to promote integration of the allograft with patient tissue over time.

A previously cryopreserved meniscal tissue can be designed to repair either MEDIAL or LATERAL defects. One product can address defects/tears for right and left knees on medial or lateral sides.

The disclosed technique can be used in patients <55 years old with radiographic evidence of failed meniscal repair or prior partial meniscectomy. Irreparable acute tears of the meniscus requiring partial meniscectomy can be repaired. Meniscus damage requiring less than 50% removal (≤25 mm peripheral corner-to-corner length) can be repaired. The technique can be used for intact posterior and anterior attachments of the involved meniscus. It can also be used for intact meniscal rim over the entire circumference (except for the area of the popliteal hiatus in the lateral meniscus). ACL deficiencies corrected simultaneously or within 12 weeks of a previously cryopreserved meniscal tissue implantation can also use this technique. Patients willing to follow postoperative rehabilitation program would be considered eligible for this technique.

The disclosed arthroscopic implantation technique can have the following contraindications: concomitant PCL insufficiency, diagnosis of uncorrected grade IV degenerative cartilage disease in the affected joint, uncorrected malformations or axial misalignment in the involved knee, systemic or local infection, evidence of osteonecrosis, medical history of chronic inflammatory/autoimmune conditions.

The following supplies can be used in the disclosed technique: a previously cryopreserved meniscal tissue graft and implant kit, Meniscal Tissue Repair System (SharpShooter by Ivy Sports Medicine, Meniscal Cinch by Arthrex, Fast-Fix 360 by Smith and Nephew, NovoStitch by Ceterix, OmniSpan by DePuy Mitek, CrossFix by Cayenne Medical, or other preferred meniscal repair system), set of zone-specific cannulas, double armed suture needles with 6 to 9" flexible needles (e.g. Conmed Part No. 8535), open ended 9" flexible needles, measuring device or flexible ruler with metric graduations, instruments for partial meniscectomy, straight overbiter punch and angled punches, scissor clamps, arthroscopic burrs or shavers, instruments for trephination or vascular engineered channel formation in meniscus periphery, surgical needles, spinal needles, blunt probe for positioning implant (trocar or obturator), slotted cannula (e.g. provided with Fast-Fix 360, or shoe-horn-shaped instrument) to assist with graft and suture passing.

1. Arthroscopic+Mini-Arthrotomy Surgical Technique

First, the subject's knee would be positioned to 90° flexion. Then, appropriate incisions would be made for arthroscopic portals. The meniscus tear/defect dimensions can then be assessed and any concomitant pathology can be assessed to determine if the patient is a candidate for segmental defect repair with a previously cryopreserved meniscal tissue.

Prior to making any cuts into meniscus tissue, the peripheral defect length should be confirmed to be ≤25 mm using an arthroscopic probe (see FIG. 16).

Using arthroscopic scissors, beaver blades, or a meniscus resection tool 2 clean radial cuts can be made to contain the tear/defect and define the new defect to be filled with a previously cryopreserved meniscal tissue (FIG. 17). Radial cuts that are perpendicular to the curvature of the peripheral rim with square shoulders are essential.

Confirm once more the distance between radial cuts is <25 mm, follow the product insert directions for thawing a cryopreserved meniscal tissue. Once thawed, the previously cryopreserved meniscal tissue can remain in RT saline for up to 2 hours prior to implantation.

Next, use arthroscopic biters or punchers (or other resection tools) to cut away tissue between the radial cuts back toward the peripheral wall of the meniscus, leaving 1-2 mm of the peripheral rim intact and undamaged. This step can allow the implant to interact with the peripheral red zone of the meniscus to promote healing, and the peripheral wall can serve as an anchor for previously cryopreserved meniscal tissue fixation.

Use a 4 mm or 5 mm arthroscopic shaver to debride and smooth out the defect edges.

A bleeding bed can be prepared by creating evenly spaced (3-5 mm apart) vascular access engineered channels along the face of the remaining meniscal defect tissue using a spinal needle. The synovium and meniscus tissue can also be roughened using a meniscus rasp to encourage bleeding and introduce progenitor cells and growth factors for healing.

Figure 18:
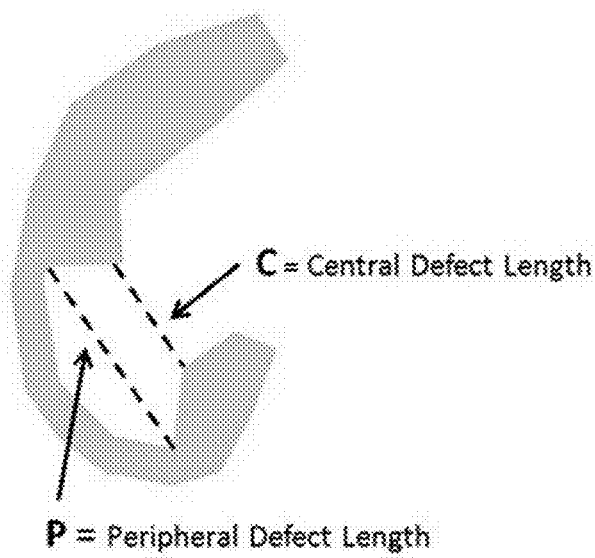
FIG. 18 is a schematic drawing showing the central defect length and peripheral defect length once the meniscal defect has been removed.

Using graduated probes or a flexible measuring device, 2 measurements can be made to define the defect: peripheral length and central length (FIG. 18). Radial lengths can be adjusted during fixation using biters. A previously cryopreserved meniscal tissue can be slightly thicker than the patient's intact peripheral rim, but does not need to be trimmed and will not adversely affect joint mechanics. Significant mismatches in thickness along the radial edges, though rare, can be addressed with shavers after initial implantation, as needed.

Figure 19:
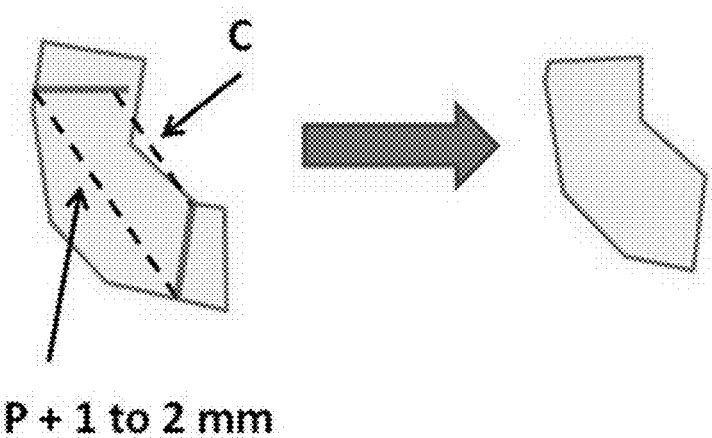
FIG. 19 is a schematic drawing showing how to cut the meniscal tissue.

The same dimensions can be traced on the a previously cryopreserved meniscal tissue graft or a sterile piece of foil or plastic using a surgical marker (FIG. 19). Press the template onto the graft to make an ink imprint and cut the graft to shape. Oversize the peripheral length by 1-2 mm (~10%) to ensure the graft is not cut too small.

Figure 20:
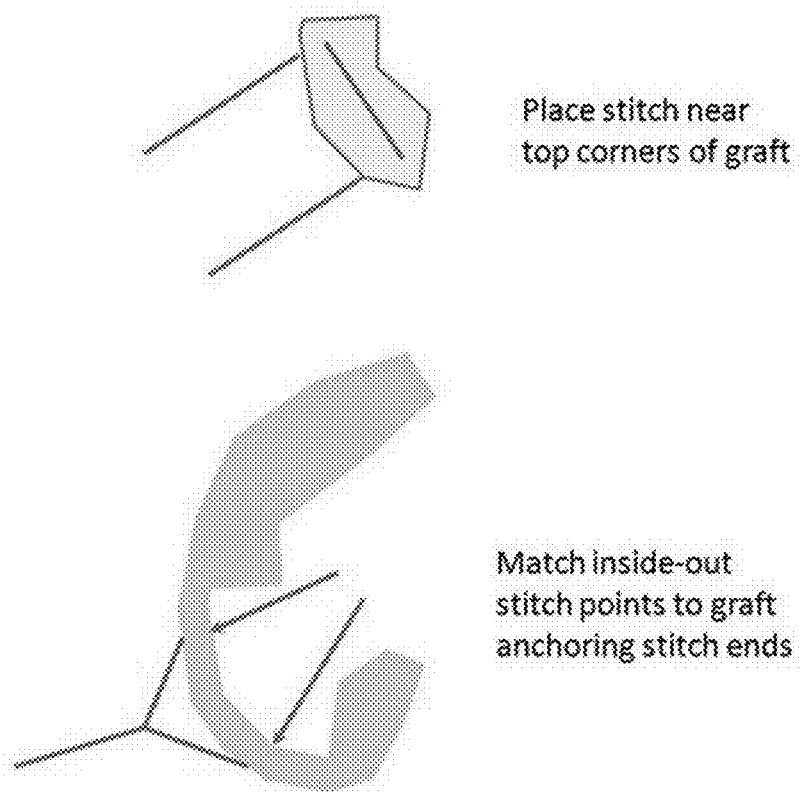
FIG. 20 is a schematic drawing showing the anchoring of a meniscal tissue composition to a meniscus that has had a meniscal defect removed.

Using flexible double-armed 6" or 9" suture needles (e.g. Conmed Part No. 8535) or a similar system, a horizontal anchoring stitch can be pre-thread into the a previously cryopreserved meniscal tissue graft. Be sure that the entry points of the suture needles are ~2 mm from the radial edges and peripheral edge of the graft, as a wide stitch can lead to improved stability inside the joint to facilitate suture fixation (FIG. 20).

Using a zone-specific cannula and an inside-out technique, each end of the double-armed suture can be threaded through the peripheral wall of the patient defect size. It is important to match the entry point of the suture in the patient's peripheral wall to the entry point of the anchoring stitch in a previously cryopreserved meniscal tissue. Avoid any neurovascular structures near the defect site while making the inside-out anchoring stitch.

Pull the graft into the defect space with the help of a slotted cannula, slide, or "shoe-horn" (e.g. slotted cannula provided with Fast-Fix 360). A probe, trochar, or grasper can be used to facilitate insertion and proper orientation of the graft.

Once the graft is properly situated in the defect, the suture ends can be clamped outside the knee joint using a hemostat, but do not tie off this anchoring stitch at this time.

Figure 21:
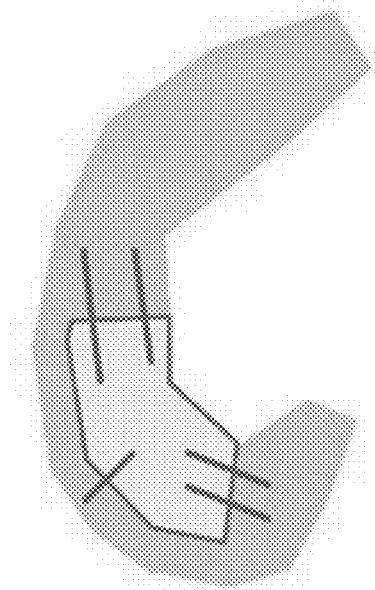
FIG. 21 is a schematic drawing showing a repaired meniscus.

Using the meniscal repair system or suturing technique of your choice (e.g. Fast-Fix, Meniscal Cinch, SharpShooter, etc.) and a braided nonresorbable 2-0 or 3-0 suture (e.g. Ethicon EXCEL, FiberWire, OrthoCord, etc.), horizontal mattress stitches or circumferential stitches can be created across both radial edges of the implant. Two horizontal stitches per radial edge is highly recommended to promote long-term fixation and healing. For larger defects, a vertical mattress suture in the center of the graft can be added (FIG. 21). The anchor stitch can be tied off or removed at this time.

Lastly, confirm fixation of a previously cryopreserved meniscal tissue arthroscopically, range the knee, and make any adjustments necessary.

To promote further healing, a notchplasty superolateral to the ACL insertion point using a flexible drill or other method can be used, as is done for radial meniscal tear repairs. Bone marrow progenitor cells and growth factors introduced into the joint space can promote early healing and integration.

B. Sheep Study: Repair of Meniscus after Partial Medial Meniscectomy in Sheep Using a Cryopreserved Viable Meniscal Allograft i. Experimental Design:

All implants were processed and cryopreserved. 2 groups, n=3, were sacrificed at 13 weeks (3 months) post-implantation: a) Devitalized (non-cryopreserved), and b) a previously cryopreserved viable allograft with Engineered Channels (CVMA).

Surgeries were conducted over 2 days, n=3 on Day 1, n=3 on Day 2.

ii. Surgical Technique for Sheep Partial Meniscectomy and Allograft Implantation The surgical approach consists of a medial incision of the right stifle made from the distal one-third of the right femur and ending below the level of the tibial plateau. With the knee joint flexed, the fat pad and fasciae are dissected to reveal the medial collateral ligament (MCL). The MCL is released including its femoral bony attachment to gain access to the medial compartment of the joint by use of an osteotome. The joint capsule is opened. Flexion and external rotation of the stifle joint can enable access to the medial meniscus.

A partial meniscectomy of the anterior horn of the right medial meniscus is performed by cutting away meniscus tissue with an 8 mm sterile biopsy punch (Acu Punch #0413 by Accuderm, Inc. Ft. Lauderdale, Fla.) leaving only ~1-2 mm of the peripheral rim of meniscus intact. The meniscal defect outer A-P length should be 8 mm across, but the anterior horn of the meniscus, ligamentous attachments, and the entire peripheral rim should remain intact and undamaged (See FIGS. 22 and 23). Care is taken to not damage the underlying tibial cartilage by sliding a metal spatula underneath meniscus.

Following partial meniscectomy, any cartilage degeneration of the tibial plateau or femoral condyles can be noted at this time. At the same time, the cryopreserved viable meniscal allograft (CVMA) corresponding to each group can be thawed in a sterile saline or water bath for 5-10 minutes, until the CVMA can be easily removed from the vial. CVMA can be transferred to a sterile saline rinsing bath and left there until sizing. The CVMA can be cut to shape to match the defect using the same 8 mm biopsy punch.

Figure 22:
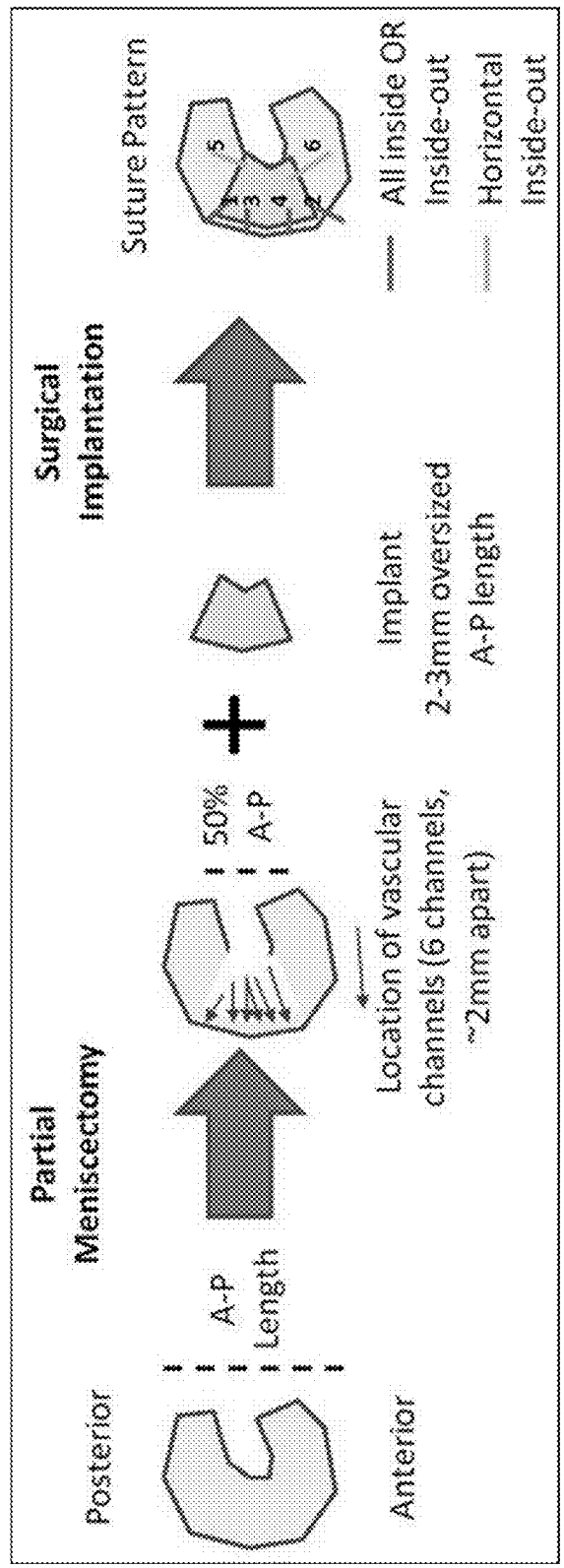
FIG. 22 shows an illustration of partial meniscectomy and meniscal allograft implantation for a mammal.
Figure 23:
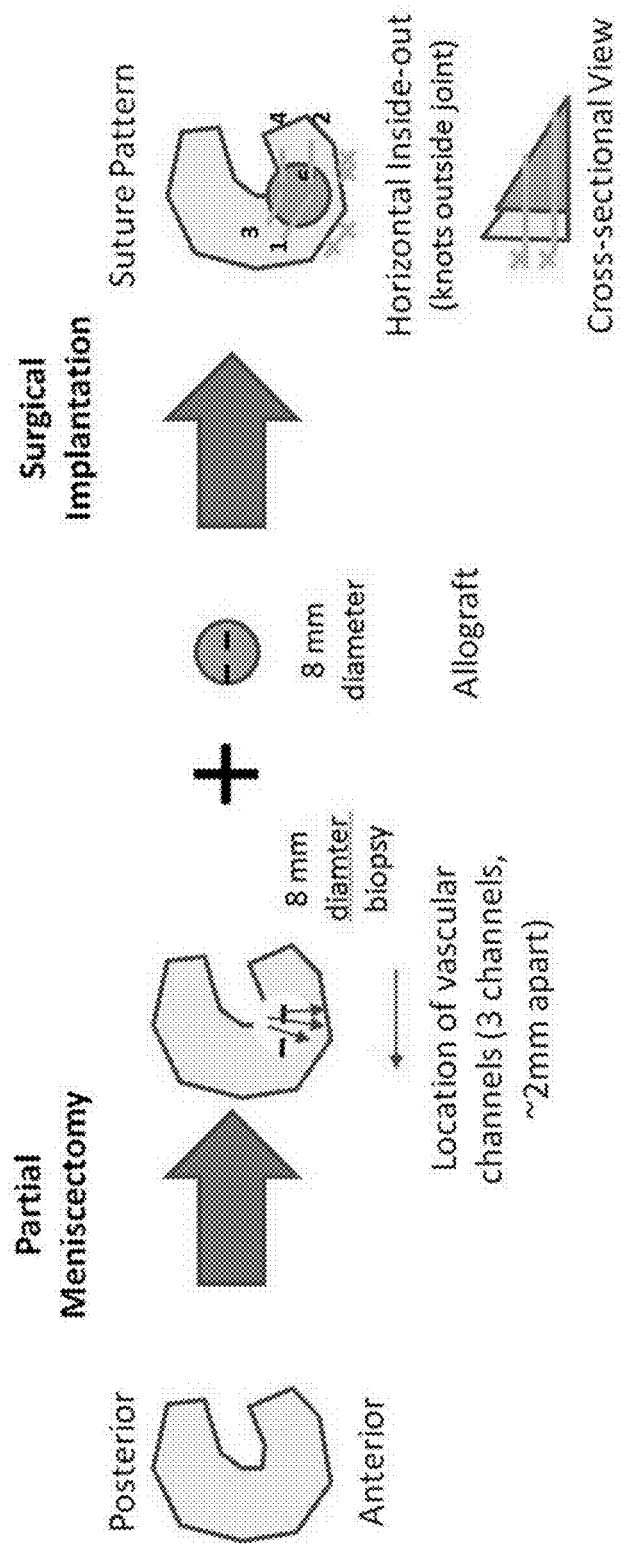
FIG. 23 shows an illustration of partial meniscectomy and meniscal allograft implantation using a biopsy method. Biopsy punch method uses a circular defect rather than trapezoidal defect.

Prior to implantation of the CVMA, the remaining host meniscus tissue can be carefully punctured with spinal needles or other small needles 2-3 times 2-3 mm apart across the surface area of the defect to create vascular channels (a.k.a. trephination), which can promote healing by bringing blood from the vascularized joint capsule to the site of healing (See FIGS. 22 and 23). Additionally, the host meniscus tissue and synovium can be roughened by applying a meniscal rasp or other tool to encourage further healing. After a bleeding bed has been prepared, the CVMA can be implanted and sutured to the host meniscus tissue using braided, non-resorbable 3-0 Ethibond Excel sutures with curved needles (X663H). First, a suture anchor stitch can be made with the help of a clamp outside the joint to keep the implant fixed in place. A total of 3 inside-out, horizontal mattress stitches can be made for optimal implant fixation. A straight or slightly curved metal cannula can be used as a guide for long suture needles to improve accuracy of stitching. Care should be taken not to nick or damage the underlying cartilage during suturing.

After CVMA has been implanted and sutured, the joint will be ranged to confirm the implant does not catch. At this time, a notchplasty of the distal femur superolateral to the ACL near the intercondylar notch may be made with a 2.4 mm Steinmann pin and hand drill for a single 1 cm deep hole inferior to the PCL insertion point on the femur. Notchplasty has been shown to promote earlier meniscus healing in humans and rabbits by introducing bone marrow elements and progenitors cells to the joint space.

After notchplasty, the joint capsule can be closed with 0 or 2-0 PDS sutures and the medial collateral ligament can be reattached with a claw plate and a bicortical bone screw. Soft tissue and fasciae can be closed in two layers using 0 or 2-0 PDS sutures, and the skin can be closed with PDS or vicryl sutures by placing a buried continuous suture in the dermis, followed by staples to close the skin. At this time, a cast/splint can be applied to the operated limb to limit weight bearing and motion. The cast can remain on for 14 days post-operatively, during which time animals are maintained in small paddocks.

iii. Results a. Summary at 3 Months Post-Implantation:

(A) Surgical Fixation

Two of three Devitalized implants were intact and remained sutured in place. 3 of 3 CVMA implants were intact and remained sutured in place (B) Integration of Implants One of three Devitalized implants had poor to good integration along the peripheral edge, but was not integrated with anterior or posterior host tissue.

Two of three CVMA implants had good to excellent integration along >50% of the defect circumference.

The posterior edge has the least integration for all tissues, likely because of high forces and lack of animal compliance (e.g. weigh bearing earlier than in the case of humans).

Clot formation and new tissue growth around implants was evident for 4 out of 6 implants (2 for each group).

(C) Histology

The one Devitalized implant with some integration was limited. Only 10% of the height of the defect showed signs of integration (top 10%) on the section stained.

No cells were evident within the Devitalized implants, but some cells were beginning to attach and grow One CVMA section showed excellent integration for 90% of the defect height, and during section preparation appeared 100% integrated by visual inspection. The interface between the CVMA and the host is not distinguishable for most of the section.

Clusters of cells are evident throughout the inner regions of all of the CVMA and significant numbers of attaching fibroblast-like cells are evident along all surfaces of the CVMA.

(D) Cell Viability of CVMA after Implantation

Zero of three devitalized implants contained any viable cells using live/dead stain of top, bottom, and inner slices of implant tissue. 3 of 3 CVMA contained significant numbers of viable cells on the top, bottom, and inside the implant. Cells were clustering together much like native chondrocytes can do during cartilage remodeling or a healing response.

Living cells were present at 3 months for the CVMA, but none for the Devitalized implants.

The invention claimed is:

1. A composition comprising a meniscal tissue allograft, wherein the meniscal tissue allograft comprises one or more engineered channels, wherein the meniscal tissue allograft comprises viable cells native to the meniscal tissue and comprises devitalized blood vessels, wherein the viable cells native to the meniscal tissue are not exogenous cells, isolated cells, or cells that are not native to the meniscal tissue.

2. The composition of claim 1, wherein the meniscal tissue allograft comprises greater than 30% viable non-immunogenic cells native to the meniscal tissue allograft and less than 5% viable immunogenic cells.

3. The composition of claim 1, wherein the meniscal tissue allograft further comprises an altered red zone.

4. The composition of claim 3, wherein the meniscal tissue allograft further comprises a red-white zone, and white zone.

5. The composition of claim 4, wherein the altered red zone, red-white zone, and white zone are in an orientation as present in native meniscal tissue allograft.

6. The composition of claim 4, wherein the engineered channels are only present in the altered red zone and red-white zone.

7. The composition of claim 3, wherein the meniscal tissue allograft has an inner edge and an opposed outer edge, and wherein the altered red zone has an outer surface that defines the outer edge of the meniscal tissue allograft.

8. The composition of claim 3, wherein the altered red zone comprises blood vessel structures native to the altered red zone.

9. The composition of claim 3, wherein the engineered channels are only present in the altered red zone.

10. The composition of claim 1, wherein each engineered channel has a diameter ranging from about 0.05 mm to about 2 mm.

11. The composition of claim 1, wherein each engineered channel has a diameter, and wherein the diameter of at least one engineered channel is equal to the diameter of at least one other engineered channel.

12. The composition of claim 11, wherein the engineered channels all have substantially the same diameter.

13. The composition of claim 1, wherein each engineered channel has a longitudinal axis, and wherein each engineered channel has a longitudinal length ranging from about 0.1 mm to about 10 mm.

14. The composition of claim 1, wherein each engineered channel has a longitudinal axis and a longitudinal length, and wherein the longitudinal length of at least one engineered channel is substantially equal to the longitudinal length of at least one other engineered channel.

15. The composition of claim 1, wherein the meniscal tissue allograft comprises at least 70% viable cells native to the meniscal tissue.

16. The composition of claim 1, wherein the meniscal tissue allograft comprises all collagen layers of human meniscus.

17. The composition of claim 1 further comprising a cryopreservation solution.

\* \* \* \* \*